US012338442B2

United States Patent
Shannon et al.

(10) Patent No.: US 12,338,442 B2
(45) Date of Patent: *Jun. 24, 2025

(54) APTAMERS AGAINST CLOSTRIDIUM DIFFICILE

(71) Applicant: LIV PROCESS, INC., Ardmore, PA (US)

(72) Inventors: Ronald J. Shannon, Ardmore, PA (US); Michael McIntyre, Ardmore, PA (US); David Bunka, York (GB); Edward Barnes, York (GB)

(73) Assignee: LIV PROCESS, INC., Ardmore, PA (US)

( * ) Notice: Subject to any disclaimer, the term of this patent is extended or adjusted under 35 U.S.C. 154(b) by 392 days.

This patent is subject to a terminal disclaimer.

(21) Appl. No.: 17/228,994

(22) Filed: Apr. 13, 2021

(65) Prior Publication Data

US 2021/0332362 A1  Oct. 28, 2021

Related U.S. Application Data

(62) Division of application No. 16/893,935, filed on Jun. 5, 2020, now Pat. No. 11,001,847.

(60) Provisional application No. 62/983,095, filed on Feb. 28, 2020, provisional application No. 62/857,639, filed on Jun. 5, 2019.

(51) Int. Cl.
*C12N 15/11* (2006.01)
*C12N 15/115* (2010.01)
*C12Q 1/689* (2018.01)

(52) U.S. Cl.
CPC ............ *C12N 15/115* (2013.01); *C12Q 1/689* (2013.01); *C12N 2310/16* (2013.01)

(58) Field of Classification Search
CPC .............. C12N 2310/16; C12N 15/115; C12N 15/1048; C12N 15/113; A61K 31/7088
See application file for complete search history.

(56) References Cited

U.S. PATENT DOCUMENTS

| | | | |
|---|---|---|---|
| 8,592,202 B2 | 11/2013 | Heyduk et al. | |
| 8,697,374 B2 | 4/2014 | Rajagopal et al. | |
| 8,895,241 B2 | 11/2014 | Ochsner et al. | |
| 9,081,010 B2 | 7/2015 | Ochsner et al. | |
| 10,145,844 B2 | 12/2018 | Cameron et al. | |
| 11,001,847 B2 | 5/2021 | Shannon | |
| 11,104,905 B2 | 8/2021 | Shannon | |
| 11,898,146 B2 | 2/2024 | Shannon et al. | |
| 2004/0023266 A1 | 2/2004 | Vivekananda | |
| 2008/0020939 A1 | 1/2008 | Stanton et al. | |
| 2009/0304683 A1 | 12/2009 | Dimitrov et al. | |
| 2010/0291100 A1 | 11/2010 | Macinga | |
| 2011/0287557 A1 | 11/2011 | Zhang et al. | |
| 2012/0231467 A1 | 9/2012 | Ochsner et al. | |
| 2012/0308569 A1 | 12/2012 | Chan et al. | |
| 2014/0230087 A1 | 8/2014 | Hartig et al. | |
| 2015/0056627 A1 | 2/2015 | Karkkainen et al. | |
| 2015/0346199 A1 | 12/2015 | Li et al. | |
| 2016/0003835 A1* | 1/2016 | Halbert .................. C12Q 1/68 506/9 |
| 2016/0143274 A1 | 5/2016 | Bingham et al. | |
| 2016/0330971 A1 | 11/2016 | Joseph | |
| 2017/0362307 A1 | 12/2017 | Ingber et al. | |
| 2018/0003712 A1 | 1/2018 | Haam et al. | |
| 2018/0271423 A1 | 9/2018 | Agarwal et al. | |
| 2019/0069836 A1 | 3/2019 | Hettrick | |
| 2019/0071714 A1 | 3/2019 | Li et al. | |
| 2020/0332296 A1 | 10/2020 | Kang | |
| 2020/0385730 A1 | 12/2020 | Shannon et al. | |
| 2020/0385731 A1 | 12/2020 | Shannon et al. | |
| 2022/0177886 A1 | 6/2022 | Shannon et al. | |
| 2022/0307029 A1 | 9/2022 | Shannon et al. | |
| 2023/0200397 A1 | 6/2023 | Shannon et al. | |
| 2023/0228751 A1 | 7/2023 | Tolley et al. | |

FOREIGN PATENT DOCUMENTS

| | | |
|---|---|---|
| CN | 109517823 A | 3/2019 |
| CN | 110938632 A | 3/2020 |
| CN | 111849994 A | 10/2020 |
| CN | 112557349 A | 3/2021 |
| GB | 2491117 A | 11/2012 |
| WO | 2004058146 A2 | 7/2004 |
| WO | 2010126670 A2 | 11/2010 |
| WO | 2014169344 A1 | 10/2014 |
| WO | 2016073562 A1 | 5/2016 |
| WO | 2018106945 A1 | 6/2018 |
| WO | 2020247755 A1 | 12/2020 |
| WO | 2021202440 A1 | 10/2021 |

(Continued)

OTHER PUBLICATIONS

Wang et al., Screening of DNA aptamers against myoglobin using a positive and negative selection units integrated microfluidic chip and its biosensing application, Analytical Chemistry, vol. 86, pp. 6572-6579. (Year: 2014).*
Ikanovic et al., "Fluorescence Assay Based on Aptamer-Quantum Dot Binding to Bacillus thuringiensis Spores," Journal of Fluorescence, Jan. 31, 2007, vol. 17, pp. 193-199.
International Search Report issued in corresponding International Patent Application No. PCT/US20/36333, mailed Nov. 19, 2020.
Calderon-Romero et al., "Clostridium difficile exosporium cysteine-rich proteins are essential for the morphogenesis of the exosporium layer, spore resistance, and affect C. difficile pathogenesis," PLOS Pathogens, Aug. 8, 2018, vol. 14, No. 8, e1007199, pp. 1-33.
Chan et al., "Antisense Oligonucleotides: From Design to Therapeutic Application," Clinical and Experimental Pharmacology Physiology, 2006, vol. 33, No. 5-6, pp. 533-540.
Diaz-Gonzalez et al., "Protein Composition of the Outermost Exosporium-like Layer of Clostridium difficile 630 Spores," Journal of Proteomics, Jun. 18, 2015, vol. 123, pp. 1-13.

(Continued)

*Primary Examiner* — Dana H Shin
(74) *Attorney, Agent, or Firm* — Greenberg Traurig, LLP; Chinh H. Pham; Natalie Salem

(57) ABSTRACT

Compositions comprising aptamers capable of specifically binding to a surface protein of *Clostridium difficile* spore are provided. A method for detecting, enriching, separating, and/or isolating *Clostridium difficile* spores is provided.

13 Claims, 29 Drawing Sheets

Specification includes a Sequence Listing.

(56) References Cited

FOREIGN PATENT DOCUMENTS

| WO | 2021211921 A2 | 10/2021 |
|---|---|---|
| WO | 2022120004 A1 | 6/2022 |

OTHER PUBLICATIONS

Hong et al., "The Spore Coat Protein CotE Facilitates Host Colonization by Clostridium Difficile," The Journal of Infectious Diseases, Dec. 12, 2017, vol. 216, No. 11, pp. 1452-1459.
Jang, Sung Key, "A '15-minute' quick diagnostic testing for newly emerging viruses introduced." Pohang University of Science and Technology, pp. 1-3, Mar. 23, 2020.
Johansson "Choosing Reporter-Quencher Pairs for Efficient Quenching Through Formation of Intramolecular Dimers," Fluorescent Energy Transfer Nucleic Acid Probes: Designs and Protocols, 2006, No. pp. 17-29.
Marras et al., "Efficiencies of Fluorescence Resonance Energy Transfer and Contact-mediated Quenching in Oligonucleotide Probes," Nucleic Acids Research, Nov. 1, 2002, vol. 30, No. 21, p. e122.
Liu et al., "In Vitro Selection of Circular DNA Aptamers for Biosensing Applications," Angewandte Chemie International Edition, 2019, vol. 58, pp. 8013-8017.
Omidbakhsh, "Evaluation of Sporicidal Activities of Selected Environmental Surface Disinfectants: Carrier Tests with the Sores of Clostridium Difficile and Its Surrogates", American Journal of Infection Control, vol. 38, No. 9, pp. 718-722, Nov. 1, 2010.
Hypothetical protein CD630_16130 [Clostridioides difficile 630], record removed, Old YP 001088114.1, accessed and retrieved from ncbi.nlm.nih.gov on Nov. 6, 2023. (Year: 2023).
CotA family spore coat protein [Clostridioides difficile], NCBI Reference Sequence: WP 003436448.1, accessed and retrieved from ncbi.nlm.nih.gov on Nov. 6, 2023. (Year: 2023).
Katilius et al., "Exploring the Sequence Space of a dna Aptamer Using Microarrays", Nucleic Acids Res., vol. 35, No. 22, pp. 7626-7635, 2007.
Mascini et al., "Nucleic Acid and Peptide Aptamers: Fundamentals and Bioanalytical Aspects", Angew Chem. Int. Ed. Engl., vol. 51, No. 6, pp. 1316-1332, Feb. 6, 2012.
Tkhawkho et al., "Destruction of Clostridium Difficile Spores Colitis Using Acidic Electrolyzed Water", Am. J. Infect. Control, vol. 45, No. 9, pp. 1053, Sep. 1, 2017.

* cited by examiner

Sequence of CdeC protein (SEQ ID NO: 18)

```
         10         20         30         40         50
MQDYKKNKRR MMNQPMSTMN EEEVYTDEIN SEDMRGFKKS HHHNGCNTDN
         60         70         80         90        100
KCECHDDCNP CNPCNPCKPN PCNPCKPNPC DDNCGCHDNC KCDCEPCEMD
        110        120        130        140        150
SDECFENKCG PECCNPISPR NFSVSNAVPF AIEANRIFDT MQFQTFTDAT
        160        170        180        190        200
GPNGEPLTFE TEVVEVFGSV PSAGQASVTI EKICLSNDGI VIDTGMTTLE
        210        220        230        240        250
DFDLDPLGDI VGRNCETTFE FAVCGERNSE CCRQGKGKSV AYKQRGLTVA
        260        270        280        290        300
VRNLVLELRG RCGCTEFVAL AFPAVRAGGG CKRRVDYVEF TFNTLSAPIC
        310        320        330        340        350
LPADGRAVTL RQEYQTNLTV DCIGKSILKL ECNECCEPFY ELIIPNDIDL
        360        370        380        390        400
VLCLQETVST LISEQIVVLA SPNPIQPRLV DTFSKVCDFS QCGPNHGSGK

PSCHR
```

FIG. 1

Sequence of CdeM protein (SEQ ID NO: 19)

```
         10         20         30         40         50
MENKKCYSED WYERGESTAK WFQNDREEYE REAYDEDRER RGSNCGCSDS
         60         70         80         90        100
GENRPRNCER FRREAEIRER EAREAFCESS EKKKEALAYE CEARKLWEEA
        110        120        130        140        150
EKYWDEYSKY NYKGIEYLAE AARLFDEGME CEARRNGNNG GNNNNCCHKC

NCNCCRK
```

FIG. 2

Sequence of CotA protein (SEQ ID NO: 15)

```
         10         20         30         40         50
MENNKCREDF RFTQEYEEDY PNTNERYYEN YQVADRYYNY PNKYKEPKIK
         60         70         80         90        100
QCCCKKSMRE ALELLRYDAL RPFVNFNQFA FISDFFIVGA NLVGIDLSAP
        110        120        130        140        150
PKDNLSGLDG TFERFSACNC DLIDIAGRVS YPIPVPLTLE GLINTIGTIP
        160        170        180        190        200
GVAELIALID AVIPPTIDLG AILDAILAAI IDFILAASTP LANVDLASLC
        210        220        230        240        250
NLKAVAFDIT PADYEDFIAS LGYYLDKKHY KECNCNCDCD DCCCNKGILD
        260        270        280        290        300
NLYMSNINNQ VTVVAGSLVL TGVEVLGKKN DVIVLGNSND SRIYFVCVDS

IDYIA
```

FIG. 3

Sequence of full-length CotE protein (SEQ ID NO: 16)

Sequence of rCoE (N281-F712) C-terminal His-tagged (MW 48,722 Da) (SEQ ID NO: 20)

Sequence of rCoEC (P381-F712) C-terminal His-tagged (MW 36875 Da) (SEQ ID NO: 17)

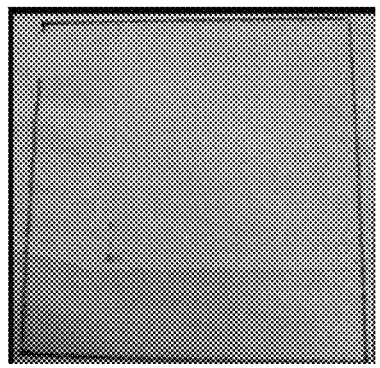
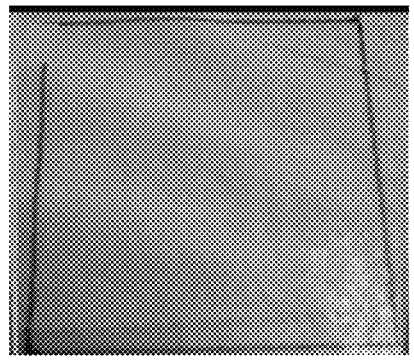
FIG. 35A
FIG. 35B
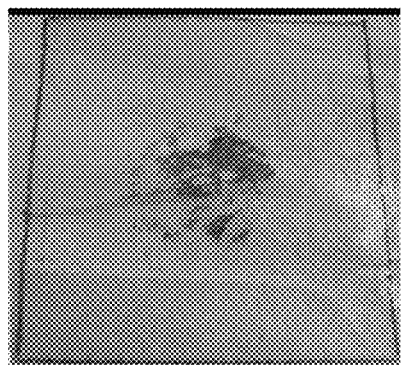
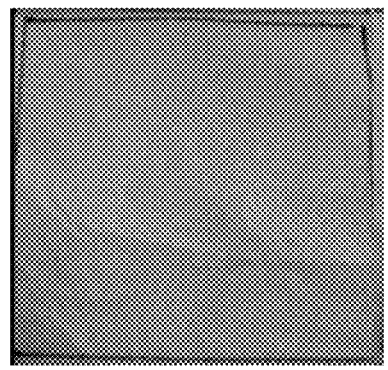
FIG. 35C
FIG. 35D
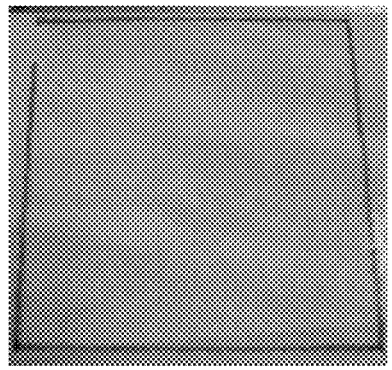
FIG. 35E

SEQUENCE LISTING

<160> NUMBER OF SEQ ID NOS: 26

<210> SEQ ID NO 1
<211> LENGTH: 81
<212> TYPE: DNA
<213> ORGANISM: Artificial Sequence
<220> FEATURE:
<223> OTHER INFORMATION: Synthetic construct

<400> SEQUENCE: 1
ccagtgtaga ctactcaatg ctcttacgat cctcacctgc tagcacaccc atatcccatg      60
cgtactatcc acaggtcaac c                                                81

<210> SEQ ID NO 2
<211> LENGTH: 81
<212> TYPE: DNA
<213> ORGANISM: Artificial Sequence
<220> FEATURE:
<223> OTHER INFORMATION: Synthetic construct

<400> SEQUENCE: 2
ccagtgtaga ctactcaatg cgggttgcga catggtggta agagctcagc ccgttcccat      60
agtactatcc acaggtcaac c                                                81

<210> SEQ ID NO 3
<211> LENGTH: 81
<212> TYPE: DNA
<213> ORGANISM: Artificial Sequence
<220> FEATURE:
<223> OTHER INFORMATION: Synthetic construct

<400> SEQUENCE: 3
ccagtgtaga ctactcaatg cacggcctgt tcgtaagacc cttacagact agtttttccc      60
tgtactatcc acaggtcaac c                                                81

<210> SEQ ID NO 4
<211> LENGTH: 81
<212> TYPE: DNA
<213> ORGANISM: Artificial Sequence
<220> FEATURE:
<223> OTHER INFORMATION: Synthetic construct

<400> SEQUENCE: 4
ccagtgtaga ctactcaatg ccctattagc tgtatcgatc cgtttagtcg ctcctccgat      60
agtactatcc acaggtcaac c                                                81

<210> SEQ ID NO 5
<211> LENGTH: 81
<212> TYPE: DNA
<213> ORGANISM: Artificial Sequence
<220> FEATURE:
<223> OTHER INFORMATION: Synthetic construct

<400> SEQUENCE: 5
ccagtgtaga ctactcaatg cctggtaaat cgatgaccgc tgcctcgcct gagtaatcat      60
cgtactatcc acaggtcaac c                                                81

<210> SEQ ID NO 6
<211> LENGTH: 81
<212> TYPE: DNA
<213> ORGANISM: Artificial Sequence
<220> FEATURE:
<223> OTHER INFORMATION: Synthetic construct -continued

```
<400> SEQUENCE: 6
ccagtgtaga ctactcaatg ccgtggactg gtcgggtttg gattcggcag atgaatcagt    60
agtactatcc acaggtcaac c                                              81

<210> SEQ ID NO 7
<211> LENGTH: 81
<212> TYPE: DNA
<213> ORGANISM: Artificial Sequence
<220> FEATURE:
<223> OTHER INFORMATION: Synthetic construct

<400> SEQUENCE: 7
ccagtgtaga ctactcaatg ccttgtaaga agaacaatcg ccgcttcgcc tgaataggtt    60
cgtactatcc acaggtcaac c                                              81

<210> SEQ ID NO 8
<211> LENGTH: 81
<212> TYPE: DNA
<213> ORGANISM: Artificial Sequence
<220> FEATURE:
<223> OTHER INFORMATION: Synthetic construct

<400> SEQUENCE: 8
ccagtgtaga ctactcaatg cggaccgttg cctcgcccga gtaatccgcc atcgcctttc    60
cgtactatcc acaggtcaac c                                              81

<210> SEQ ID NO 9
<211> LENGTH: 81
<212> TYPE: DNA
<213> ORGANISM: Artificial Sequence
<220> FEATURE:
<223> OTHER INFORMATION: Synthetic construct

<400> SEQUENCE: 9
ccagtgtaga ctactcaatg cttaagttct ggggacacgt gatgaacgca tttaatgggg    60
cgtactatcc acaggtcaac c                                              81

<210> SEQ ID NO 10
<211> LENGTH: 81
<212> TYPE: DNA
<213> ORGANISM: Artificial Sequence
<220> FEATURE:
<223> OTHER INFORMATION: Synthetic construct

<400> SEQUENCE: 10
ccagtgtaga ctactcaatg ccgtggactg gtcgggtttg gattcggcag atgaatcact    60
agtactatcc acaggtcaac c                                              81

<210> SEQ ID NO 11
<211> LENGTH: 81
<212> TYPE: DNA
<213> ORGANISM: Artificial Sequence
<220> FEATURE:
<223> OTHER INFORMATION: Synthetic construct

<400> SEQUENCE: 11
ccagtgtaga ctactcaatg cggctgtgtg acttgacctt tggaatgggt gggagggatg    60
ggtactatcc acaggtcaac c                                              81

<210> SEQ ID NO 12
```

<211> LENGTH: 76
<212> TYPE: DNA
<213> ORGANISM: Artificial Sequence
<220> FEATURE:
<223> OTHER INFORMATION: Synthetic construct

<400> SEQUENCE: 12

```
ccagtgtaga ctactcaatg cggtgtggtg accttgacct atggaacctg gttgtagtac    60
tatccacagg tcaacc                                                    76
```

<210> SEQ ID NO 13
<211> LENGTH: 82
<212> TYPE: DNA
<213> ORGANISM: Artificial Sequence
<220> FEATURE:
<223> OTHER INFORMATION: Synthetic construct

<400> SEQUENCE: 13

```
ccagtgtaga ctactcaatg ctcgacattt ccgccccgac ggccctccta gtgatgggga    60
gagtactatc cacaggtcaa cc                                             82
```

<210> SEQ ID NO 14
<211> LENGTH: 81
<212> TYPE: DNA
<213> ORGANISM: Artificial Sequence
<220> FEATURE:
<223> OTHER INFORMATION: Synthetic construct

<400> SEQUENCE: 14

```
ccagtgtaga ctactcaatg ccttccattc acctaccgag ctaagcgttc gacttaggtc    60
tgtactatcc acaggtcaac c                                              81
```

<210> SEQ ID NO 15
<211> LENGTH: 305
<212> TYPE: PRT
<213> ORGANISM: clostridium difficile

<400> SEQUENCE: 15

```
Met Glu Asn Asn Lys Cys Arg Glu Asp Phe Arg Phe Thr Gln Glu Tyr
1               5                   10                  15

Glu Glu Asp Tyr Pro Asn Thr Asn Glu Arg Tyr Tyr Glu Asn Tyr Gln
            20                  25                  30

Val Ala Asp Arg Tyr Tyr Asn Tyr Pro Asn Lys Tyr Lys Glu Pro Lys
        35                  40                  45

Ile Lys Gln Cys Cys Cys Lys Lys Ser Met Arg Glu Ala Leu Glu Leu
    50                  55                  60

Leu Arg Tyr Asp Ala Leu Arg Pro Phe Val Asn Phe Asn Gln Phe Ala
65                  70                  75                  80

Phe Ile Ser Asp Phe Phe Ile Val Gly Ala Asn Leu Val Gly Ile Asp
                85                  90                  95

Leu Ser Ala Pro Pro Lys Asp Asn Leu Ser Gly Leu Asp Gly Thr Phe
            100                 105                 110

Glu Arg Phe Ser Ala Cys Asn Cys Asp Leu Ile Asp Ile Ala Gly Arg
        115                 120                 125

Val Ser Tyr Pro Ile Pro Val Pro Leu Thr Leu Glu Gly Leu Ile Asn
    130                 135                 140

Thr Ile Gly Thr Ile Pro Gly Val Ala Glu Leu Ile Ala Leu Ile Asp
145                 150                 155                 160

Ala Val Ile Pro Pro Thr Ile Asp Leu Gly Ala Ile Leu Asp Ala Ile
```

```
                165                 170                 175
Leu Ala Ala Ile Ile Asp Phe Ile Leu Ala Ala Ser Thr Pro Leu Ala
            180                 185                 190

Asn Val Asp Leu Ala Ser Leu Cys Asn Leu Lys Ala Val Ala Phe Asp
            195                 200                 205

Ile Thr Pro Ala Asp Tyr Glu Asp Phe Ile Ala Ser Leu Gly Tyr Tyr
            210                 215                 220

Leu Asp Lys Lys His Tyr Lys Glu Cys Asn Cys Asn Cys Asp Cys Asp
225                 230                 235                 240

Asp Cys Cys Cys Asn Lys Gly Ile Leu Asp Asn Leu Tyr Met Ser Asn
                245                 250                 255

Ile Asn Asn Gln Val Thr Val Val Ala Gly Ser Leu Val Leu Thr Gly
            260                 265                 270

Val Glu Val Leu Gly Lys Lys Asn Asp Val Ile Val Leu Gly Asn Ser
            275                 280                 285

Asn Asp Ser Arg Ile Tyr Phe Val Cys Val Asp Ser Ile Asp Tyr Ile
            290                 295                 300

Ala
305

<210> SEQ ID NO 16
<211> LENGTH: 712
<212> TYPE: PRT
<213> ORGANISM: clostridium difficile

<400> SEQUENCE: 16

Met Ile Tyr Met Pro Asn Leu Pro Ser Leu Gly Ser Lys Ala Pro Asp
1               5                   10                  15

Phe Lys Ala Asn Thr Thr Asn Gly Pro Ile Arg Leu Ser Asp Tyr Lys
                20                  25                  30

Gly Asn Trp Ile Val Leu Phe Ser His Pro Gly Asp Phe Thr Pro Val
            35                  40                  45

Cys Thr Thr Glu Phe Leu Cys Phe Ala Lys Tyr Tyr Asp Glu Phe Lys
        50                  55                  60

Lys Arg Asn Thr Glu Leu Ile Gly Leu Ser Val Asp Ser Asn Ser Ser
65                  70                  75                  80

His Leu Ala Trp Met Tyr Asn Ile Ser Leu Leu Thr Gly Val Glu Ile
                85                  90                  95

Pro Phe Pro Ile Ile Glu Asp Arg Asp Met Arg Ile Ala Lys Leu Tyr
            100                 105                 110

Gly Met Ile Ser Lys Pro Met Ser Asp Thr Ser Thr Val Arg Ser Val
        115                 120                 125

Phe Ile Ile Asp Asn Asn Gln Ile Leu Arg Thr Ile Leu Tyr Tyr Pro
    130                 135                 140

Leu Thr Thr Gly Arg Asn Ile Pro Glu Ile Leu Arg Ile Val Asp Ala
145                 150                 155                 160

Leu Gln Thr Ser Asp Arg Asp Asn Ile Val Thr Pro Ala Asn Trp Phe
                165                 170                 175

Pro Gly Met Pro Val Ile Leu Pro Tyr Pro Lys Asn Tyr Lys Glu Leu
            180                 185                 190

Lys Asn Arg Val Asn Ser Cys Asn Lys Lys Tyr Ser Cys Met Asp Trp
        195                 200                 205

Tyr Leu Cys Phe Val Pro Asp Asn Tyr Asn Asp Glu Glu Val Ser Lys
    210                 215                 220
```

-continued

```
Lys Ile Asp Asn Thr Cys Ser Trp Lys Lys Glu His Thr Lys Asn Ile
225                 230                 235                 240

Glu Asn Glu Cys Asn Cys Glu His Glu His His Asp Tyr Leu Asn Lys
            245                 250                 255

Ala Leu Asp Cys Lys Gln Glu His Lys Thr Asp Ile Lys Asp Asp Cys
            260                 265                 270

Asn His Glu Lys Lys His Thr Lys Asn Thr Asn Lys Val His Asn Ser
        275                 280                 285

Lys Gln Asp Lys Phe Lys Asp Lys Ser Cys Asp Glu Met Asn Phe Asn
    290                 295                 300

Tyr Asp Lys Asp Glu Ser Cys Asp Lys Ile Asn Ser Ser Tyr Asn Lys
305                 310                 315                 320

Glu Asp Ser Ser Tyr Glu Asp Phe Tyr Lys His Asn Tyr Lys Asn Tyr
                325                 330                 335

Asp Tyr Thr Ser Glu Lys Asn Thr Lys Lys Ile Ala Met Lys Thr Leu
            340                 345                 350

Lys Asp Ser Lys Lys Leu Val Arg Pro Gln Ile Thr Asp Pro Tyr Asn
        355                 360                 365

Pro Ile Val Glu Asn Ala Asn Cys Pro Asp Ile Asn Pro Ile Val Ala
    370                 375                 380

Glu Tyr Val Leu Gly Asn Pro Thr Asn Val Asp Ala Gln Leu Leu Asp
385                 390                 395                 400

Ala Val Ile Phe Ala Phe Ala Glu Ile Asp Gln Ser Gly Asn Leu Phe
                405                 410                 415

Ile Pro Tyr Pro Arg Phe Leu Asn Gln Leu Leu Ala Leu Lys Gly Glu
            420                 425                 430

Lys Pro Ser Leu Lys Val Ile Val Ala Ile Gly Gly Trp Gly Ala Glu
        435                 440                 445

Gly Phe Ser Asp Ala Ala Leu Thr Pro Thr Ser Arg Tyr Asn Phe Ala
    450                 455                 460

Arg Gln Val Asn Gln Met Ile Asn Glu Tyr Ala Leu Asp Gly Ile Asp
465                 470                 475                 480

Ile Asp Trp Glu Tyr Pro Gly Ser Ser Ala Ser Gly Ile Thr Ser Arg
                485                 490                 495

Pro Gln Asp Arg Glu Asn Phe Thr Leu Leu Leu Thr Ala Ile Arg Asp
            500                 505                 510

Val Ile Gly Asp Asp Lys Trp Leu Ser Val Ala Gly Thr Gly Asp Arg
        515                 520                 525

Gly Tyr Ile Asn Ser Ser Ala Glu Ile Asp Lys Ile Ala Pro Ile Ile
    530                 535                 540

Asp Tyr Phe Asn Leu Met Ser Tyr Asp Phe Thr Ala Gly Glu Thr Gly
545                 550                 555                 560

Pro Asn Gly Arg Lys His Gln Ala Asn Leu Phe Asp Ser Asp Leu Ser
                565                 570                 575

Leu Pro Gly Tyr Ser Val Asp Ala Met Val Arg Asn Leu Glu Asn Ala
            580                 585                 590

Gly Met Pro Ser Glu Lys Ile Leu Leu Gly Ile Pro Phe Tyr Gly Arg
        595                 600                 605

Leu Gly Ala Thr Ile Thr Arg Thr Tyr Asp Glu Leu Arg Arg Asp Tyr
    610                 615                 620

Ile Asn Lys Asn Gly Tyr Glu Tyr Arg Phe Asp Asn Thr Ala Gln Val
625                 630                 635                 640

Pro Tyr Leu Val Lys Asp Gly Asp Phe Ala Met Ser Tyr Asp Asp Ala
```

-continued

```
                    645                 650                 655
Leu Ser Ile Phe Leu Lys Thr Gln Tyr Val Leu Arg Asn Cys Leu Gly
                660                 665                 670

Gly Val Phe Ser Trp Thr Ser Thr Tyr Asp Gln Ala Asn Ile Leu Ala
                675                 680                 685

Arg Thr Met Ser Ile Gly Ile Asn Asp Pro Glu Val Leu Lys Glu Glu
                690                 695                 700

Leu Glu Gly Ile Tyr Gly Gln Phe
705                 710
```

<210> SEQ ID NO 17
<211> LENGTH: 332
<212> TYPE: PRT
<213> ORGANISM: Clostridium difficile

<400> SEQUENCE: 17

```
Pro Ile Val Ala Glu Tyr Val Leu Gly Asn Pro Thr Asn Val Asp Ala
1               5                   10                  15

Gln Leu Leu Asp Ala Val Ile Phe Ala Phe Ala Glu Ile Asp Gln Ser
                20                  25                  30

Gly Asn Leu Phe Ile Pro Tyr Pro Arg Phe Leu Asn Gln Leu Leu Ala
            35                  40                  45

Leu Lys Gly Glu Lys Pro Ser Leu Lys Val Ile Val Ala Ile Gly Gly
        50                  55                  60

Trp Gly Ala Glu Gly Phe Ser Asp Ala Ala Leu Thr Pro Thr Ser Arg
65                  70                  75                  80

Tyr Asn Phe Ala Arg Gln Val Asn Gln Met Ile Asn Glu Tyr Ala Leu
                85                  90                  95

Asp Gly Ile Asp Ile Asp Trp Glu Tyr Pro Gly Ser Ser Ala Ser Gly
            100                 105                 110

Ile Thr Ser Arg Pro Gln Asp Arg Glu Asn Phe Thr Leu Leu Leu Thr
        115                 120                 125

Ala Ile Arg Asp Val Ile Gly Asp Asp Lys Trp Leu Ser Val Ala Gly
    130                 135                 140

Thr Gly Asp Arg Gly Tyr Ile Asn Ser Ser Ala Glu Ile Asp Lys Ile
145                 150                 155                 160

Ala Pro Ile Ile Asp Tyr Phe Asn Leu Met Ser Tyr Asp Phe Thr Ala
                165                 170                 175

Gly Glu Thr Gly Pro Asn Gly Arg Lys His Gln Ala Asn Leu Phe Asp
            180                 185                 190

Ser Asp Leu Ser Leu Pro Gly Tyr Ser Val Asp Ala Met Val Arg Asn
        195                 200                 205

Leu Glu Asn Ala Gly Met Pro Ser Glu Lys Ile Leu Leu Gly Ile Pro
    210                 215                 220

Phe Tyr Gly Arg Leu Gly Ala Thr Ile Thr Arg Thr Tyr Asp Glu Leu
225                 230                 235                 240

Arg Arg Asp Tyr Ile Asn Lys Asn Gly Tyr Glu Tyr Arg Phe Asp Asn
                245                 250                 255

Thr Ala Gln Val Pro Tyr Leu Val Lys Asp Gly Asp Phe Ala Met Ser
            260                 265                 270

Tyr Asp Asp Ala Leu Ser Ile Phe Leu Lys Thr Gln Tyr Val Leu Arg
        275                 280                 285

Asn Cys Leu Gly Gly Val Phe Ser Trp Thr Ser Thr Tyr Asp Gln Ala
    290                 295                 300
```

-continued

```
Asn Ile Leu Ala Arg Thr Met Ser Ile Gly Ile Asn Asp Pro Glu Val
305                 310                 315                 320

Leu Lys Glu Glu Leu Glu Gly Ile Tyr Gly Gln Phe
            325                 330

<210> SEQ ID NO 18
<211> LENGTH: 405
<212> TYPE: PRT
<213> ORGANISM: Clostridium difficile

<400> SEQUENCE: 18

Met Gln Asp Tyr Lys Lys Asn Lys Arg Met Met Asn Gln Pro Met
1               5                   10                  15

Ser Thr Met Asn Glu Glu Val Tyr Thr Asp Glu Ile Asn Ser Glu
                20                  25                  30

Asp Met Arg Gly Phe Lys Lys Ser His His Asn Gly Cys Asn Thr
            35                  40                  45

Asp Asn Lys Cys Glu Cys His Asp Asp Cys Asn Pro Cys Asn Pro Cys
50                  55                  60

Asn Pro Cys Lys Pro Asn Pro Cys Asn Pro Cys Lys Pro Asn Pro Cys
65                  70                  75                  80

Asp Asp Asn Cys Gly Cys His Asp Asn Cys Lys Cys Asp Cys Glu Pro
                85                  90                  95

Cys Glu Met Asp Ser Asp Glu Cys Phe Glu Lys Cys Gly Pro Glu
                100                 105                 110

Cys Cys Asn Pro Ile Ser Pro Arg Asn Phe Ser Val Ser Asn Ala Val
            115                 120                 125

Pro Phe Ala Ile Glu Ala Asn Arg Ile Phe Asp Thr Met Gln Phe Gln
130                 135                 140

Thr Phe Thr Asp Ala Thr Gly Pro Asn Gly Glu Pro Leu Thr Phe Glu
145                 150                 155                 160

Thr Glu Val Val Glu Val Phe Gly Ser Val Pro Ser Ala Gly Gln Ala
                165                 170                 175

Ser Val Thr Ile Glu Lys Ile Cys Leu Ser Asn Asp Gly Ile Val Ile
            180                 185                 190

Asp Thr Gly Met Thr Thr Leu Glu Asp Phe Asp Leu Asp Pro Leu Gly
        195                 200                 205

Asp Ile Val Gly Arg Asn Cys Glu Thr Thr Phe Glu Phe Ala Val Cys
210                 215                 220

Gly Glu Arg Asn Ser Glu Cys Cys Arg Gln Gly Lys Gly Lys Ser Val
225                 230                 235                 240

Ala Tyr Lys Gln Arg Gly Leu Thr Val Ala Val Arg Asn Leu Val Leu
                245                 250                 255

Glu Leu Arg Gly Arg Cys Gly Cys Thr Glu Phe Val Ala Leu Ala Phe
            260                 265                 270

Pro Ala Val Arg Ala Gly Gly Cys Lys Arg Arg Val Asp Tyr Val
        275                 280                 285

Glu Phe Thr Phe Asn Thr Leu Ser Ala Pro Ile Cys Leu Pro Ala Asp
290                 295                 300

Gly Arg Ala Val Thr Leu Arg Gln Glu Tyr Gln Thr Asn Leu Thr Val
305                 310                 315                 320

Asp Cys Ile Gly Lys Ser Ile Leu Lys Leu Glu Cys Asn Glu Cys Cys
                325                 330                 335

Glu Pro Phe Tyr Glu Leu Ile Ile Pro Asn Asp Ile Asp Leu Val Leu
            340                 345                 350
```

```
Cys Leu Gln Glu Thr Val Ser Thr Leu Ile Ser Glu Gln Ile Val Val
        355                 360                 365

Leu Ala Ser Pro Asn Pro Ile Gln Pro Arg Leu Val Asp Thr Phe Ser
    370                 375                 380

Lys Val Cys Asp Phe Ser Gln Cys Gly Pro Asn His Gly Ser Gly Lys
385                 390                 395                 400

Pro Ser Cys His Arg
                405

<210> SEQ ID NO 19
<211> LENGTH: 157
<212> TYPE: PRT
<213> ORGANISM: Clostridium difficile

<400> SEQUENCE: 19

Met Glu Asn Lys Lys Cys Tyr Ser Glu Asp Trp Tyr Glu Arg Gly Glu
1               5                   10                  15

Ser Thr Ala Lys Trp Phe Gln Asn Asp Arg Glu Glu Tyr Glu Arg Glu
            20                  25                  30

Ala Tyr Asp Glu Asp Arg Glu Arg Arg Gly Ser Asn Cys Gly Cys Ser
        35                  40                  45

Asp Ser Gly Glu Asn Arg Pro Arg Asn Cys Glu Arg Phe Arg Arg Glu
    50                  55                  60

Ala Glu Ile Arg Glu Arg Glu Ala Arg Glu Ala Phe Cys Glu Ser Ser
65                  70                  75                  80

Glu Lys Lys Lys Glu Ala Leu Ala Tyr Glu Cys Glu Ala Arg Lys Leu
                85                  90                  95

Trp Glu Glu Ala Glu Lys Tyr Trp Asp Glu Tyr Ser Lys Tyr Asn Tyr
            100                 105                 110

Lys Gly Ile Glu Tyr Leu Ala Glu Ala Ala Arg Leu Phe Asp Glu Gly
        115                 120                 125

Met Glu Cys Glu Ala Arg Arg Asn Gly Asn Asn Gly Gly Asn Asn Asn
    130                 135                 140

Asn Cys Cys His Lys Cys Asn Cys Asn Cys Cys Arg Lys
145                 150                 155

<210> SEQ ID NO 20
<211> LENGTH: 432
<212> TYPE: PRT
<213> ORGANISM: clostridium difficile

<400> SEQUENCE: 20

Asn Thr Asn Lys Val His Asn Ser Lys Gln Asp Lys Phe Lys Asp Lys
1               5                   10                  15

Ser Cys Asp Glu Met Asn Phe Asn Tyr Asp Lys Asp Glu Ser Cys Asp
            20                  25                  30

Lys Ile Asn Ser Ser Tyr Asn Lys Glu Asp Ser Ser Tyr Glu Asp Phe
        35                  40                  45

Tyr Lys His Asn Tyr Lys Asn Tyr Asp Tyr Thr Ser Glu Lys Asn Thr
    50                  55                  60

Lys Lys Ile Ala Met Lys Thr Leu Lys Asp Ser Lys Lys Leu Val Arg
65                  70                  75                  80

Pro Gln Ile Thr Asp Pro Tyr Asn Pro Ile Val Glu Asn Ala Asn Cys
                85                  90                  95

Pro Asp Ile Asn Pro Ile Val Ala Glu Tyr Val Leu Gly Asn Pro Thr
            100                 105                 110
```

Asn Val Asp Ala Gln Leu Leu Asp Ala Val Ile Phe Ala Phe Ala Glu
            115                 120                 125

Ile Asp Gln Ser Gly Asn Leu Phe Ile Pro Tyr Pro Arg Phe Leu Asn
    130                 135                 140

Gln Leu Leu Ala Leu Lys Gly Glu Lys Pro Ser Leu Lys Val Ile Val
145                 150                 155                 160

Ala Ile Gly Gly Trp Gly Ala Glu Gly Phe Ser Asp Ala Ala Leu Thr
                165                 170                 175

Pro Thr Ser Arg Tyr Asn Phe Ala Arg Gln Val Asn Gln Met Ile Asn
            180                 185                 190

Glu Tyr Ala Leu Asp Gly Ile Asp Ile Asp Trp Glu Tyr Pro Gly Ser
        195                 200                 205

Ser Ala Ser Gly Ile Thr Ser Arg Pro Gln Asp Arg Glu Asn Phe Thr
    210                 215                 220

Leu Leu Leu Thr Ala Ile Arg Asp Val Ile Gly Asp Lys Trp Leu
225                 230                 235                 240

Ser Val Ala Gly Thr Gly Asp Arg Gly Tyr Ile Asn Ser Ser Ala Glu
                245                 250                 255

Ile Asp Lys Ile Ala Pro Ile Ile Asp Tyr Phe Asn Leu Met Ser Tyr
            260                 265                 270

Asp Phe Thr Ala Gly Glu Thr Gly Pro Asn Gly Arg Lys His Gln Ala
        275                 280                 285

Asn Leu Phe Asp Ser Asp Leu Ser Leu Pro Gly Tyr Ser Val Asp Ala
    290                 295                 300

Met Val Arg Asn Leu Glu Asn Ala Gly Met Pro Ser Glu Lys Ile Leu
305                 310                 315                 320

Leu Gly Ile Pro Phe Tyr Gly Arg Leu Gly Ala Thr Ile Thr Arg Thr
                325                 330                 335

Tyr Asp Glu Leu Arg Arg Asp Tyr Ile Asn Lys Asn Gly Tyr Glu Tyr
            340                 345                 350

Arg Phe Asp Asn Thr Ala Gln Val Pro Tyr Leu Val Lys Asp Gly Asp
        355                 360                 365

Phe Ala Met Ser Tyr Asp Asp Ala Leu Ser Ile Phe Leu Lys Thr Gln
    370                 375                 380

Tyr Val Leu Arg Asn Cys Leu Gly Gly Val Phe Ser Trp Thr Ser Thr
385                 390                 395                 400

Tyr Asp Gln Ala Asn Ile Leu Ala Arg Thr Met Ser Ile Gly Ile Asn
                405                 410                 415

Asp Pro Glu Val Leu Lys Glu Glu Leu Glu Gly Ile Tyr Gly Gln Phe
            420                 425                 430

<210> SEQ ID NO 21
<211> LENGTH: 21
<212> TYPE: DNA
<213> ORGANISM: Artificial Sequence
<220> FEATURE:
<223> OTHER INFORMATION: Synthetic construct

<400> SEQUENCE: 21
ccagtgtaga ctactcaatg c                                         21

<210> SEQ ID NO 22
<211> LENGTH: 20
<212> TYPE: DNA
<213> ORGANISM: Artificial Sequence
<220> FEATURE:

```
<223> OTHER INFORMATION: Synthetic construct

<400> SEQUENCE: 22
gtactatcca caggtcaacc                                                    20

<210> SEQ ID NO 23
<211> LENGTH: 36
<212> TYPE: DNA
<213> ORGANISM: Artificial Sequence
<220> FEATURE:
<223> OTHER INFORMATION: Synthetic construct

<400> SEQUENCE: 23
atcgatgacc gctgcctcgc ctgagtaatc atcgta                                  36

<210> SEQ ID NO 24
<211> LENGTH: 33
<212> TYPE: DNA
<213> ORGANISM: Artificial Sequence
<220> FEATURE:
<223> OTHER INFORMATION: Synthetic Construct

<400> SEQUENCE: 24
ccatactcaa tgctcttacg atcctcatca acc                                     33

<210> SEQ ID NO 25
<211> LENGTH: 41
<212> TYPE: DNA
<213> ORGANISM: Artificial Sequence
<220> FEATURE:
<223> OTHER INFORMATION: Synthetic construct

<400> SEQUENCE: 25
ccagtgtaga ctactcaatg ctcttacgat cctcatcaac c                            41

<210> SEQ ID NO 26
<211> LENGTH: 38
<212> TYPE: DNA
<213> ORGANISM: Artificial Sequence
<220> FEATURE:
<223> OTHER INFORMATION: Synthetic construct

<400> SEQUENCE: 26
agtgtagact actcaatgcg gctggccaca ggtcaacc                                38
```

APTAMERS AGAINST CLOSTRIDIUM DIFFICILE

RELATED APPLICATIONS

This application is a divisional application of U.S. application Ser. No. 16/893,935, filed Jun. 5, 2020, which claims the benefit of and the priority to U.S. Provisional application Ser. No. 62/857,639, filed Jun. 5, 2019 and Provisional application Ser. No. 62/983,095, filed Feb. 28, 2020, the entire disclosure of each of which is herein incorporated by reference in their entireties.

SEQUENCE LISTING

The instant application contains a Sequence Listing, submitted herewith which includes the file 193519-010109_ST25.txt having the following size 25,642 bytes, which was created on Apr. 13, 2021, the contents of which are hereby incorporated by reference herein.

FIELD OF THE INVENTION

Embodiments of the present invention relate to aptamers that specifically bind to a *Clostridium difficile* spore and methods of using the same. For example, embodiments of the invention relate to methods of detecting the presence, absence or amount of *C. difficile* bacteria e.g. spores in a sample using the aptamers described herein.

BACKGROUND TO THE INVENTION

*Clostridium difficile* (also referred to as *C. difficile*) is a Gram-positive, anaerobic spore former and is an important nosocomial and community-acquired pathogenic bacterium. *C. difficile* infections (CDI) are a leading cause of infections worldwide with elevated rates of morbidity and mortality. Given the rise in antibiotic resistance and the potential mortality associated with *C. difficile* infection, control measures are of the highest importance.

SUMMARY

Some aspects of the disclosure relate to an aptamer having a specific binding affinity for a surface protein of *Clostridium difficile* spore, wherein the surface protein is a spore coat surface protein or an exosporium layer protein.

In some embodiments, the surface protein is CdeC, CdeM, CotA, CotE or CotE Chitinase. In some embodiments, the surface protein is CdeC having an amino acid sequence as set forth in SEQ ID NO 18. In some embodiments, the surface protein is CdeM having an amino acid sequence as set forth in SEQ ID NO: 19. In some embodiments, the surface protein is CotA having an amino acid sequence as set forth in SEQ ID NO: 15. In some embodiments, the surface protein is CotE having an amino acid sequence as set forth in SEQ ID NO: 16. In some embodiments, the surface protein is CotE Chitinase protein having an amino acid sequence as set forth in SEQ ID NO: 17.

In some embodiments, the aptamer comprises a nucleic acid sequence having at least 90% identity with any one of SEQ ID NOs: 1 to 14 or SEQ ID NOs: 23-26. In some embodiments, the aptamer comprises a nucleic acid sequence having at least about 30 consecutive nucleotides of a sequence having at least 90% identity with any one of SEQ ID NOs: 1 to 14 or SEQ ID NOs: 23-26.

In some embodiments, the aptamer is a single stranded DNA aptamer.

In some embodiments, the aptamer comprises a detectable label. In some embodiments, the detectable label comprises a fluorophore, a nanoparticle, a quantum dot, an enzyme, a radioactive isotope, a pre-defined sequence portion, a biotin, a desthiobiotin, a thiol group, an amine group, an azide, an aminoallyl group, a digoxigenin, an antibody, a catalyst, a colloidal metallic particle, a colloidal non-metallic particle, an organic polymer, a latex particle, a nanofiber, a nanotube, a dendrimer, a protein, a liposome, or combination thereof.

In some embodiments, a composition comprising at least one aptamer is provided. In some embodiments, the composition comprises at least one of water, salt, buffer, detergent, and bovine serum albumin (BSA).

Some aspects of the disclosure relate to a complex comprising (a) an aptamer having a specific binding affinity for a surface protein of a *Clostridium difficile* spore, wherein the surface protein is a spore coat surface protein or an exosporium layer protein, and (b) a detectable molecule. In some embodiments, the surface protein is CdeC, CdeM, CotA, CotE or CotE Chitinase.

Some aspects of the disclosure relate to a biosensor or test strip comprising an aptamer having a specific binding affinity for a surface protein of *Clostridium difficile* spore, wherein the surface protein is a spore coat surface protein or an exosporium layer protein. In some embodiments, the surface protein is CdeC, CdeM, CotA, CotE or CotE Chitinase. In some embodiments, the aptamer comprises a nucleic acid sequence having at least 90% identity with any one of the nucleic acid sequences as set forth in any of SEQ ID NOs: 1 to 14 or SEQ ID NOs: 23-26. In some embodiments, the aptamer comprises a nucleic acid sequence having at least about 30 consecutive nucleotides of a sequence having at least 90% identity with any one of SEQ ID NOs: 1 to 14 or SEQ ID NOs: 23-26.

Other aspects of the disclosure relate to an apparatus for detecting the presence, absence or level of *Clostridium difficile* spores in a sample, the apparatus comprising a support, and an aptamer having a specific binding affinity for a surface protein of *Clostridium difficile* spore, wherein the surface protein is a spore coat surface protein or an exosporium layer protein. In some embodiments, the surface protein is CdeC, CdeM, CotA, CotE or CotE Chitinase. In some embodiments, the aptamer comprises a nucleic acid sequence having at least 90% identity with any one of the nucleic acid sequences as set forth in any of SEQ ID NOs: 1 to 14 or SEQ ID NOs: 23-26. In some embodiments, the aptamer comprises a nucleic acid sequence having at least about 30 consecutive nucleotides of a sequence having at least 90% identity with any one of SEQ ID NOs: 1 to 14 or SEQ ID NOs: 23-26. In some embodiments, the sample is a sample obtained from a subject suspected of having or diagnosed with a *Clostridium difficile* infection or an object located in a hospital environment. In some embodiments, the apparatus is suitable for surface plasmon resonance (SPR), biolayer interferometry (BLI), lateral flow assay and/or enzyme-linked oligonucleotide assay (ELONA).

In some aspects of the disclosure, there is provided a use of an aptamer, a complex, a composition, a biosensor or test strip, or an apparatus as described herein for detecting, enriching, separating and/or isolating *Clostridium difficile* spores.

In some aspects of the disclosure, there is provided a method of detecting the presence, absence or amount of *Clostridium difficile* in a sample, the method comprising interacting the sample with an aptamer, a complex, a composition as described herein, and detecting the presence, absence or amount of *Clostridium difficile*.

Some aspects of the disclosure relate to a method of visualizing *Clostridium difficile* spores on a surface, comprising contacting a surface with an aptamer having a specific binding affinity for a surface protein of *Clostridium difficile* spore, wherein the surface protein is a spore coat surface protein or an exosporium layer protein, and visualizing the presence or absence of *C. difficile* spores on the surface. In some embodiments, the surface protein is CdeC, CdeM, CotA, CotE or CotE Chitinase. In some embodiments, the contacting comprises contacting the surface for a predetermined period of time sufficient to enable the aptamer to bind to a *Clostridium difficile* spore.

In some embodiments, the method further comprises washing of the surface after the contacting to remove unbound aptamer.

In some embodiments, the method further comprises visualizing the aptamer bound to a *Clostridium difficile* spore, thereby detecting the *Clostridium difficile* spore.

In some embodiments, the aptamer comprises a nucleic acid sequence having at least 90% identity with any one of the nucleic acid sequences as set forth in any of SEQ ID NOs: 1 to 14 or SEQ ID NOs: 23-26. In some embodiments, the aptamer comprises a nucleic acid sequence having at least about 30 consecutive nucleotides of a sequence having at least 90% identity with any one of SEQ ID NOs: 1 to 14 or SEQ ID NOs: 23-26.

In some embodiments, the aptamer is conjugated to a detectable moiety thereby forming an aptamer conjugate. In some embodiments, the detectable moiety is a fluorophore. In some embodiments, the fluorophore emits at a wavelength of between about 500 nm and 510 nm.

In some embodiments, the method further comprises illuminating the surface with a light source. In some embodiments, light from the light source has a predetermined wavelength, and the predetermined wavelength corresponds to a wavelength of light emitted by the detectable moiety of the aptamer conjugate. In some embodiments, the light source is configured to produce light at a wavelength of between about 485 nm and 515 nm. In some embodiments, the method further comprises filtering the light produced by the light source. In some embodiments, the method comprises passing the light produced from the light source through a bandpass filter.

In some embodiments, the method further comprises photographing a location on the surface and detecting the presence or absence of the conjugated aptamer bound to *Clostridium difficile* spores.

Other aspects of the disclosure relate to a kit for visualizing *Clostridium difficile* spores, the kit comprising (a) an aptamer comprising a detectable moiety, the aptamer having a specific binding affinity for a surface protein of *Clostridium difficile* spore, wherein the surface protein is a spore coat surface protein or an exosporium layer protein, (b) a light source, and (c) viewing goggles.

In some embodiments, the surface protein is CdeC, CdeM, CotA, CotE or CotE Chitinase.

In some embodiments, the kit further comprises a bandpass filter.

In some embodiments, the detectable moiety is a fluorophore that emits a wavelength of between about 485 nm to 515 nm, the light source is configured to produce a light having a wavelength of between about 485 nm to 515 nm, and the viewing goggles are orange viewing goggles.

In some embodiments, the light source produces light having a wavelength of about 505 nm.

In some embodiments, the bandpass filter is a 590 nm bandpass filter.

In some embodiments, the kit further comprises a wash solution to remove unbound aptamers.

In some embodiments, the aptamer is comprised in a buffer solution.

BRIEF DESCRIPTION OF THE DRAWINGS

Embodiments of the present invention will be better understood when read in conjunction with the appended drawings. For the purposes of illustrating the invention, there are shown in the drawings embodiments which may be preferred. It is understood, however, that the invention is not limited to the precise arrangements and instrumentalities shown.

FIG. 1 shows the amino acid sequence (SEQ ID NO: 18) of *Clostridium difficile* CdeC protein.

FIG. 2 shows the amino acid sequence (SEQ ID NO: 19) of *Clostridium difficile* CdeM protein.

FIG. 3 shows the amino acid sequence (SEQ ID NO: 15) of *Clostridium difficile* CotA protein.

FIG. 4 shows the amino acid sequence (SEQ ID NO: 16) of *Clostridium difficile* CotE protein.

FIG. 5A shows the amino acid sequence (SEQ ID NO: 20) of *Clostridium difficile* rCotE protein (N281-F712) C-terminal His-tagged (MW 48,722 Da).

FIG. 5B shows the amino acid sequence (SEQ ID NO: 17) of *Clostridium difficile* rCotEC chitinase protein (P381-F712) C-terminal His-tagged (MW 36,875 Da).

FIG. 25A illustrates the results of the fluorescently labelled aptamer population after 3 rounds of cell selection. FIG. 25B illustrates the results of the fluorescently labelled aptamer population after 4 rounds of cell selection. The black box signifies dust on the lens.

FIG. 31A illustrates the untreated stainless-steel surface (negative control 1); FIG. 31B illustrates *Clostridium difficile* SH11 spores (negative control 2); FIG. 31C illustrates horse blood (negative control 3); FIG. 31D illustrates 10 µM CotE H2 aptamer in buffer (positive control 4); and FIG. 31E illustrates the 10 µM CotE H2 aptamer-*Clostridium difficile* SH11 spore suspension.

FIG. 32A illustrates the untreated stainless-steel surface (negative control 1); FIG. 32B illustrates *Clostridium difficile* SH11 spores (negative control 2); FIG. 32C illustrates horse blood (negative control 3); FIG. 32D illustrates 10 µM CotE H2 aptamer in buffer (positive control 4); and FIG. 32E illustrates the 10 µM CotE H2 aptamer-*Clostridium difficile* SH11 spore suspension.

FIG. 33A illustrates the untreated stainless-steel surface (negative control 1); FIG. 33B illustrates *Clostridium difficile* SH11 spores (negative control 2); FIG. 33C illustrates horse blood (negative control 3); FIG. 33D illustrates 10 µM CotE H2 aptamer in buffer (positive control 4; and FIG. 33E illustrates the 10 µM CotE H2 aptamer-*Clostridium difficile* SH11 spore suspension.

FIG. 34A illustrates the untreated stainless-steel surface (negative control 1); FIG. 34B illustrates *Clostridium difficile* SH11 spores (negative control 2); FIG. 34C illustrates horse blood (negative control 3); FIG. 34D illustrates 10 µM CotE H2 aptamer in buffer (positive control 4); and FIG. 34E illustrates the 10 µM CotE H2 aptamer-*Clostridium difficile* SH11 spore suspension.

FIG. 35A-FIG. 35E show photographs of test samples on a gown surface under ambient light conditions without Polilight Flare+2 forensic light (505 nm) and without 590 nm bandpass filter according to some embodiments of the present disclosure. For comparison, FIG. 35A illustrates the untreated stainless-steel surface (negative control 1); FIG. 35B illustrates *Clostridium difficile* SH11 spores (negative control 2); FIG. 35C illustrates horse blood (negative control 3); FIG. 35D illustrates 10 µM CotE H2 aptamer in buffer (positive control 4); and FIG. 35E illustrates the 10 µM CotE H2 aptamer-*Clostridium difficile* SH11 spore suspension.

FIG. 36A illustrates the untreated stainless-steel surface (negative control 1); FIG. 36B illustrates *Clostridium difficile* SH11 spores (negative control 2); FIG. 36C illustrates horse blood (negative control 3); FIG. 36D illustrates 10 µM CotE H2 aptamer in buffer (positive control 4); and FIG. 36E illustrates the 10 µM CotE H2 aptamer-*Clostridium difficile* SH11 spore suspension.

FIG. 37A illustrates the untreated stainless-steel surface (negative control 1); FIG. 37B illustrates *Clostridium difficile* SH11 spores (negative control 2); FIG. 37C illustrates horse blood (negative control 3); FIG. 37D illustrates 10 µM CotE H2 aptamer in buffer (positive control 4); and FIG. 37E illustrates the 10 µm CotE H2 aptamer-*Clostridium difficile* SH11 spore suspension.

FIG. 38A illustrates the untreated stainless-steel surface (negative control 1); FIG. 38B illustrates *Clostridium difficile* SH11 spores (negative control 2); FIG. 38C illustrates horse blood (negative control 3); FIG. 38D illustrates 10 µm CotE H2 aptamer in buffer (positive control 4); and FIG. 38E illustrates the 10 µm CotE H2 aptamer-*Clostridium difficile* SH11 spore suspension.

DETAILED DESCRIPTION

*Clostridium difficile*

Figure 6:
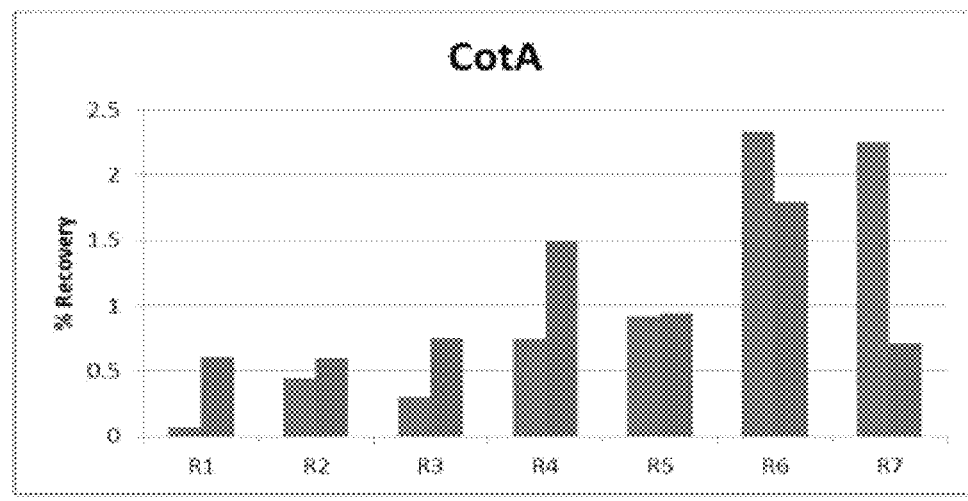
FIG. 6 shows aptamer recovery following sequential selection rounds in an assay comparing aptamer recovery from CotA loaded beads (left side of each data set) with aptamer recovery from blank beads (right side of each data set) according to some embodiments of the present disclosure.
Figure 7:
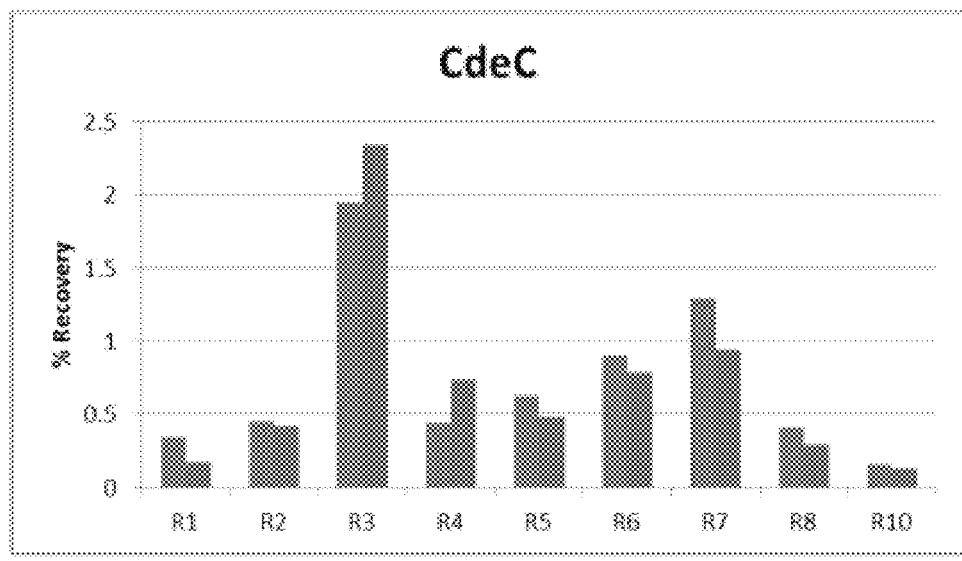
FIG. 7 shows aptamer recovery following sequential selection rounds in an assay comparing aptamer recovery from CdeC loaded beads (left side of each data set) with aptamer recovery from blank beads (right side of each data set) according to some embodiments of the present disclosure.
Figure 8:
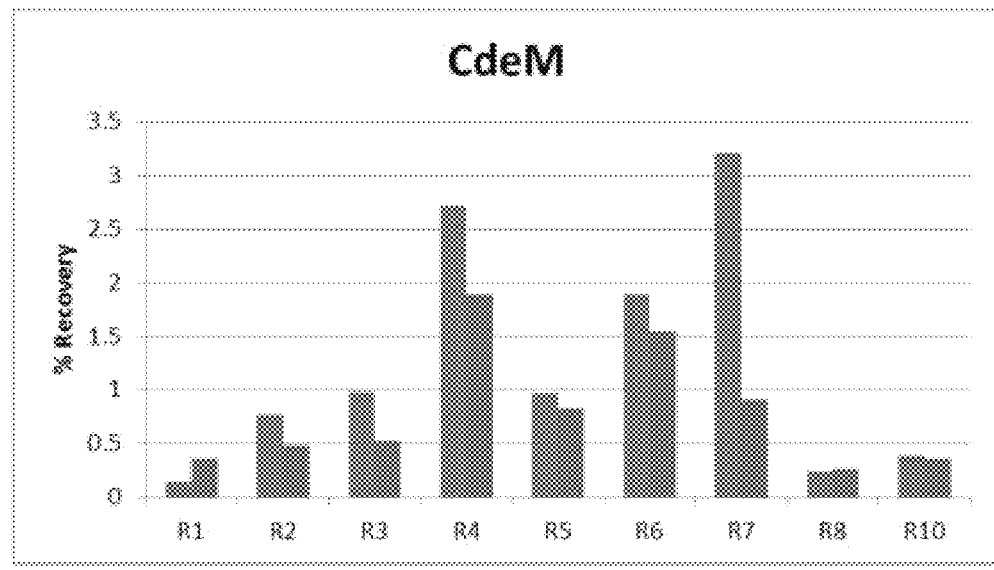
FIG. 8 shows aptamer recovery following sequential selection rounds in an assay comparing aptamer recovery from CdeM loaded beads (left side of each data set) with aptamer recovery from blank beads (right side of each data set) according to some embodiments of the present disclosure.
Figure 9:
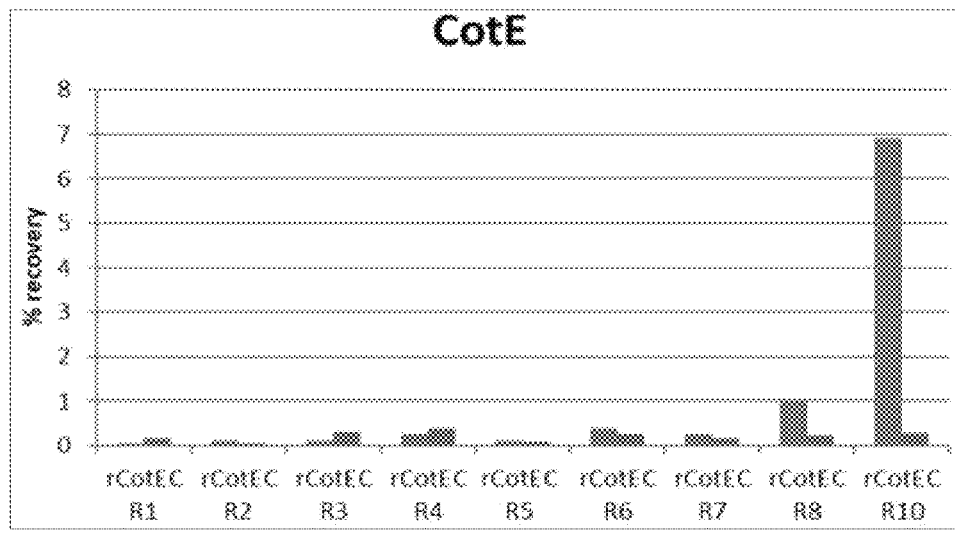
FIG. 9 shows aptamer recovery following sequential selection rounds in an assay comparing aptamer recovery from CotE loaded beads (left side of each data set) with aptamer recovery from blank beads (right side of each data set according to some embodiments of the present disclosure.
Figure 10:
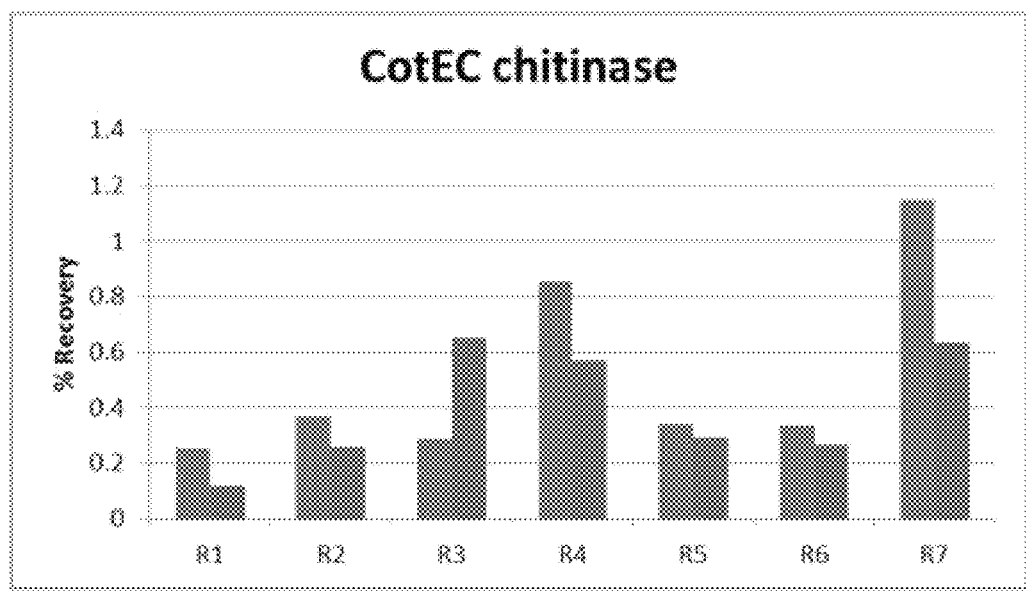
FIG. 10 shows aptamer recovery following sequential selection rounds in an assay comparing aptamer recovery from CotEC Chitinase loaded beads (left side of each data set) with aptamer recovery from blank beads (right side of each data set) according to some embodiments of the present disclosure.
Figure 11:
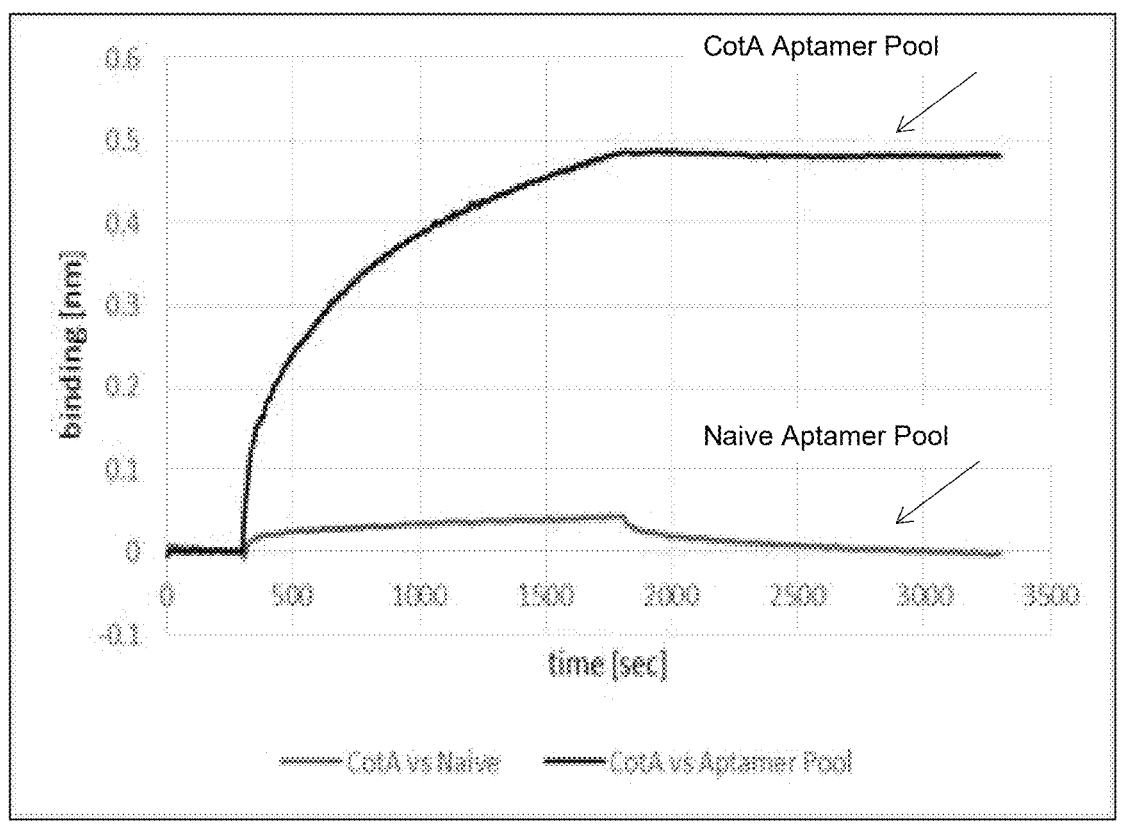
FIG. 11 shows Biolayer Interferometry (BLI) data comparing interactions between immobilized CotA and the naïve library (Naive Aptamer Pool) or immobilized CotA and the refined aptamer population (CotA Aptamer Pool) according to some embodiments of the present disclosure.
Figure 12:
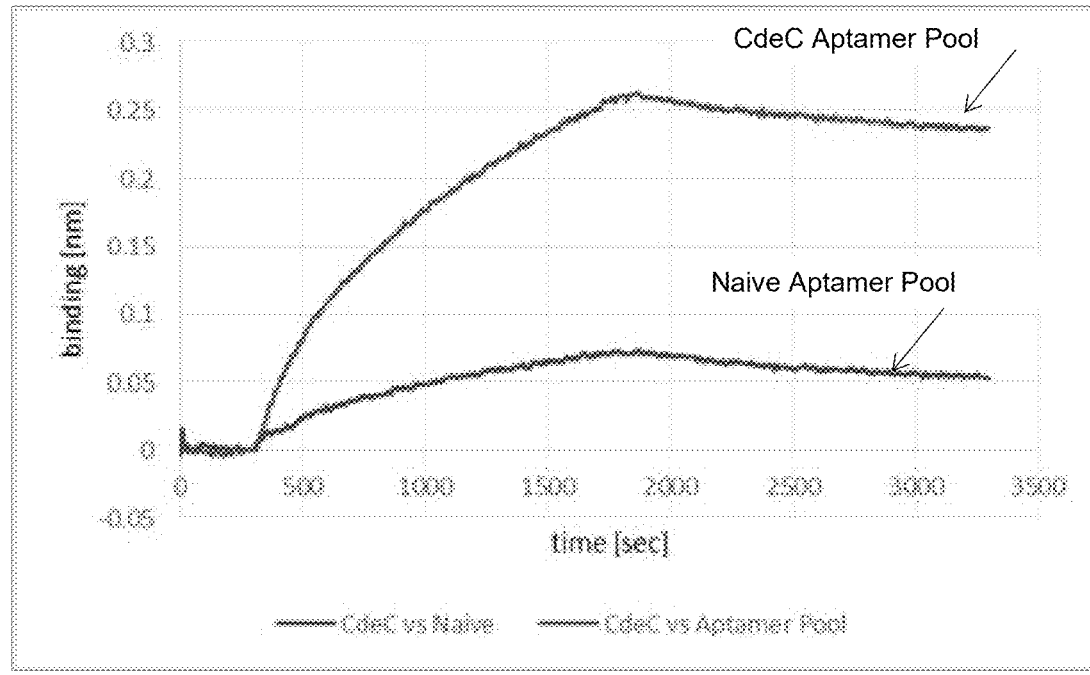
FIG. 12 shows Biolayer Interferometry (BLI) data comparing interactions between immobilized CdeC and the naïve library (Naive Aptamer Pool) or immobilized CdeC and the refined aptamer population (CdeC Aptamer Pool) according to some embodiments of the present disclosure.
Figure 13:
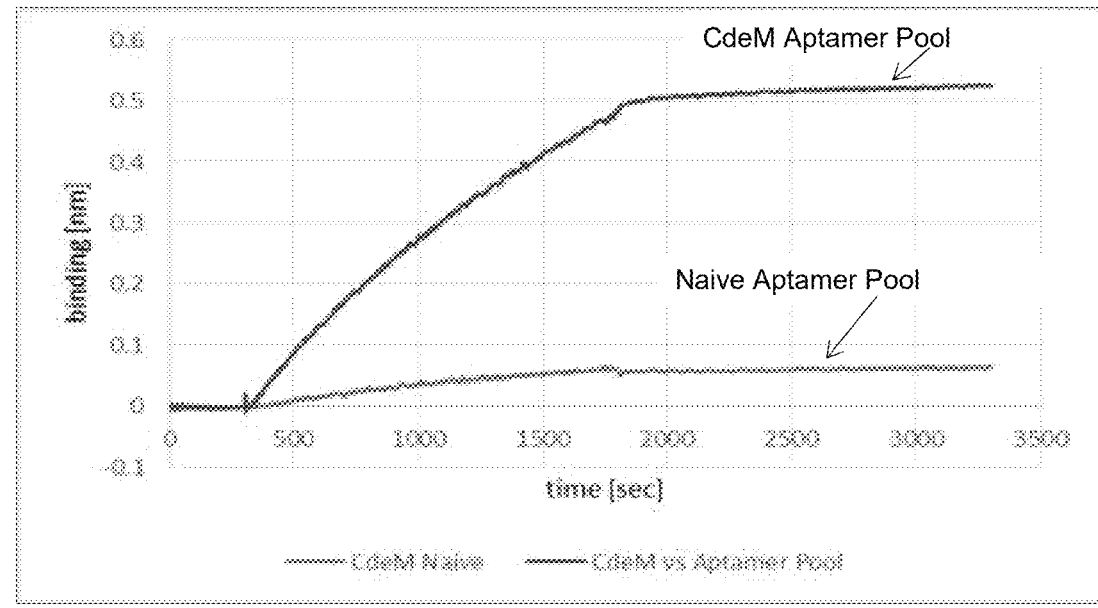
FIG. 13 shows Biolayer Interferometry (BLI) data comparing interactions between immobilized CdeM and the naïve library (Naive Aptamer Pool) or immobilized CdeM and the refined aptamer population (CdeM Aptamer Pool) according to some embodiments of the present disclosure.
Figure 14:
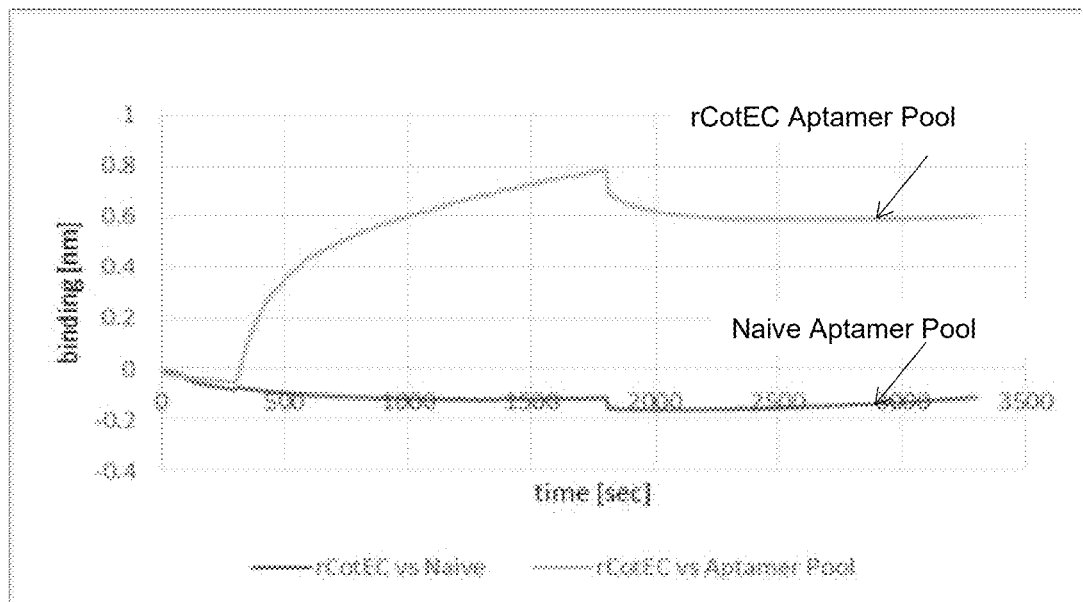
FIG. 14 shows Biolayer Interferometry (BLI) data comparing interactions between immobilized CotE and the naïve library (Naive Aptamer Pool) or immobilized CotE and the refined aptamer population (rCotEC Aptamer Pool) according to some embodiments of the present disclosure.
Figure 15:
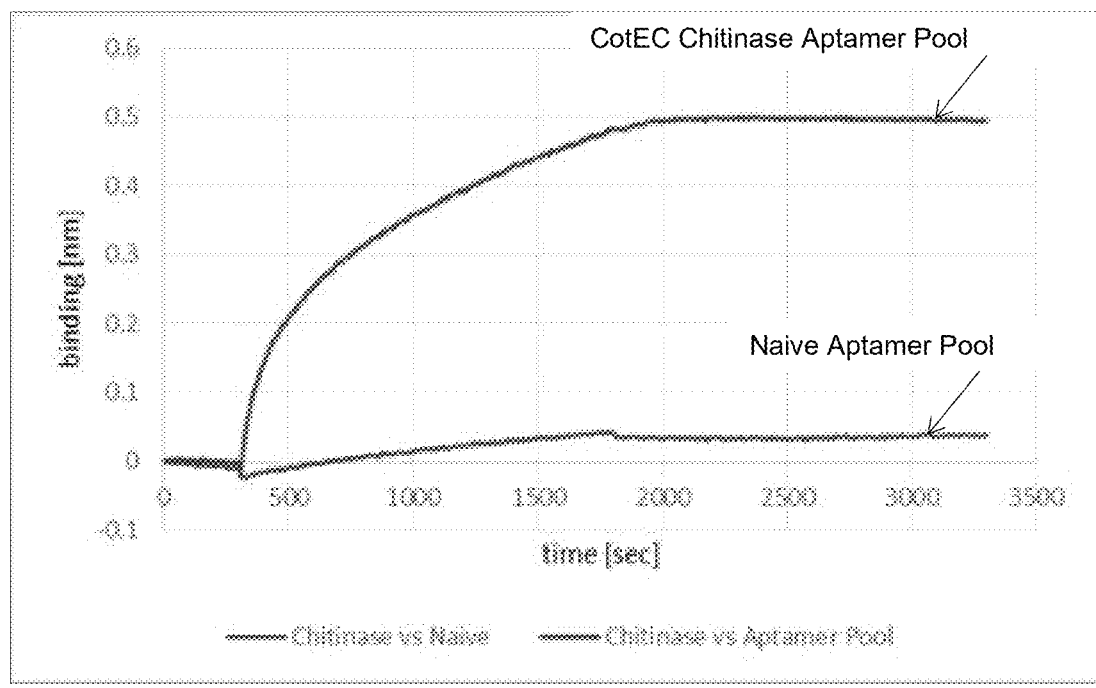
FIG. 15 shows Biolayer Interferometry (BLI) data comparing interactions between immobilized CotEC Chitinase and the naïve library (Naive Aptamer Pool) or immobilized CotEC Chitinase and the refined aptamer population (CotEC Aptamer Pool) according to some embodiments of the present disclosure.
Figure 16:
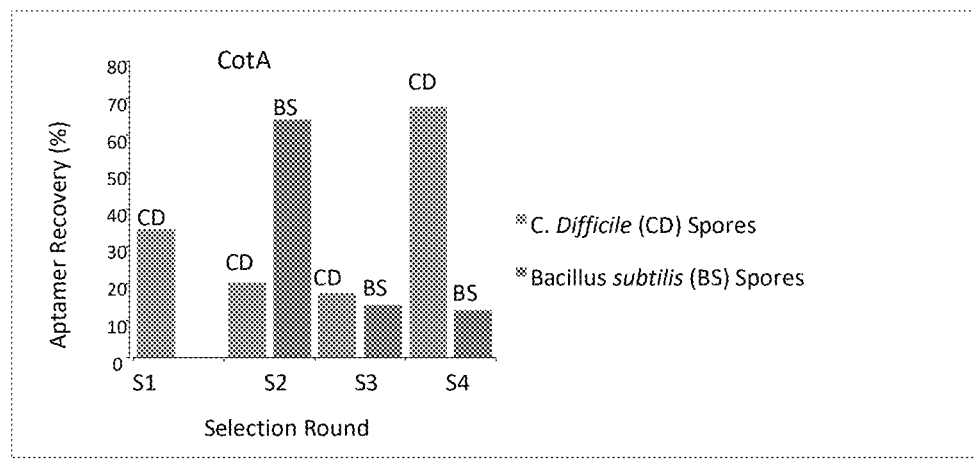
FIG. 16 shows the % aptamer recovery from sequential rounds of spore-based selection; comparing aptamer recovery from *Clostridium difficile* spores (CD) with recovery from *Bacillus subtilis* spores (BS) for each of the aptamer populations (named for their protein target—CotA) according to some embodiments of the present disclosure.
Figure 17:
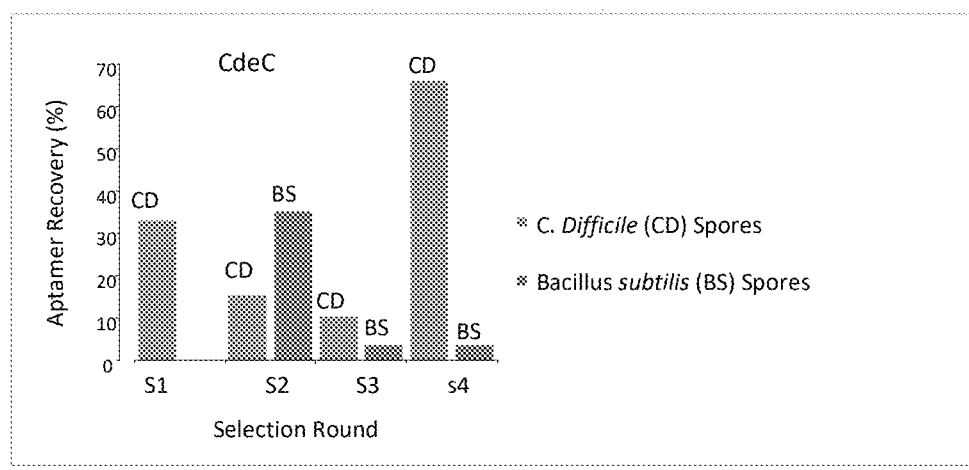
FIG. 17 shows the % aptamer recovery from sequential rounds of spore-based selection; comparing aptamer recovery from *Clostridium difficile* spores (CD) with recovery from *Bacillus subtilis* spores (BS) for each of the aptamer populations (named for their protein target—CdeC) according to some embodiments of the present disclosure.
Figure 18:
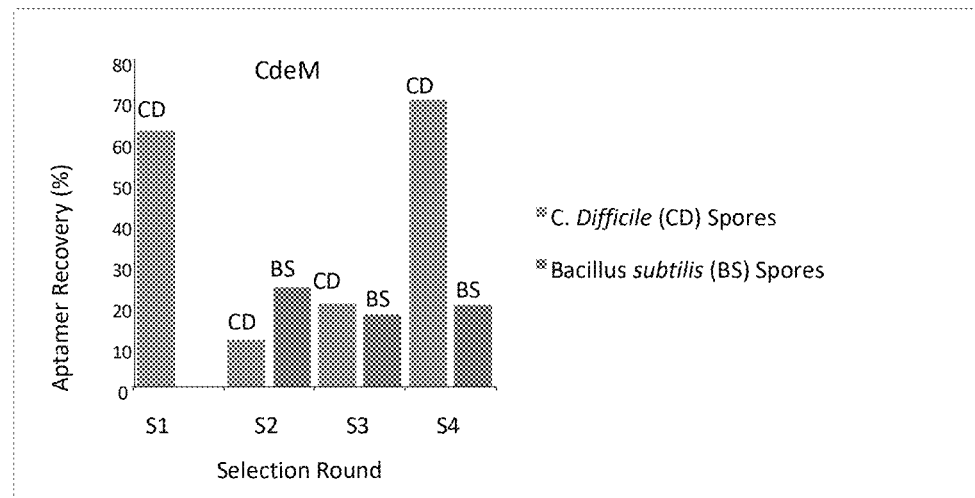
FIG. 18 shows the % aptamer recovery from sequential rounds of spore-based selection; comparing aptamer recovery from *Clostridium difficile* spores (CD) with recovery from *Bacillus subtilis* spores (BS) for each of the aptamer populations (named for their protein target—CdeM) according to some embodiments of the present disclosure.
Figure 19:
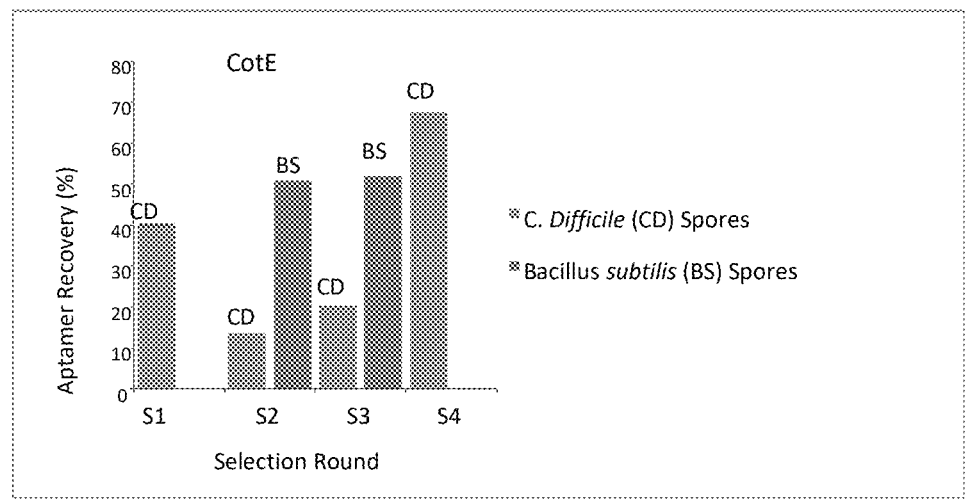
FIG. 19 shows the % aptamer recovery from sequential rounds of spore-based selection; comparing aptamer recovery from *Clostridium difficile* spores (CD) with recovery from *Bacillus subtilis* spores (BS) for each of the aptamer populations (named for their protein target—CotE) according to some embodiments of the present disclosure.
Figure 20:
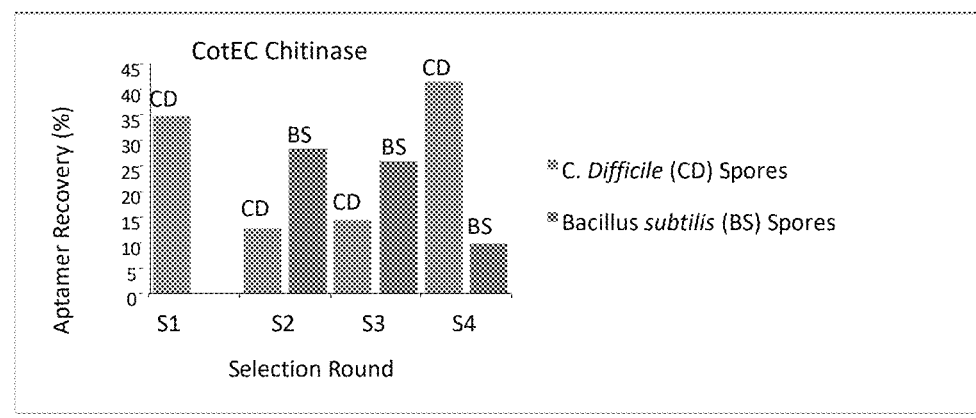
FIG. 20 shows the % aptamer recovery from sequential rounds of spore-based selection; comparing aptamer recovery from *Clostridium difficile* spores (CD) with recovery from *Bacillus subtilis* spores (BS) for each of the aptamer populations (named for their protein target—CotEC chitinase) according to some embodiments of the present disclosure.
Figure 21:
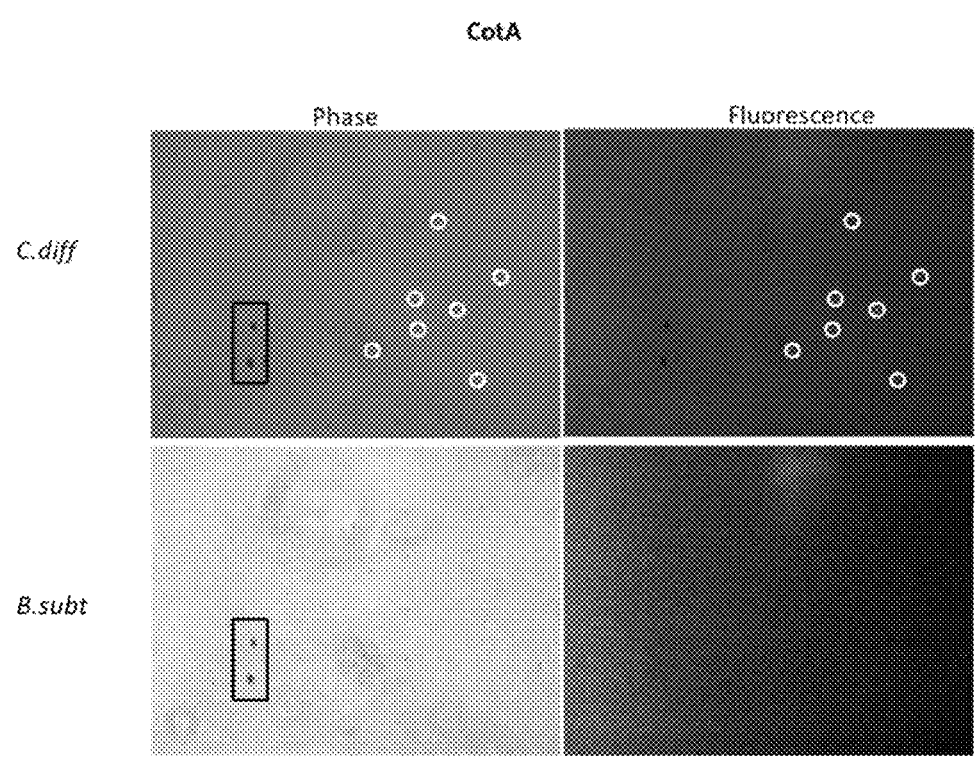
FIG. 21 shows brightfield images (left) and epifluoresence images (right) according to some embodiments of the present disclosure. *C. difficile* spores are localised to the upper images and *B. subtilis* spores are localised to the lower images. Epifluorescence images of localised *C. difficile* spores (upper right) show spots of fluorescence which colocalise with *C. difficile* spores, which is indicative of binding of the fluorescently labeled aptamer population selected against CotA to the *C. difficile* spores. Spores showing fluorescent signals are highlighted with circles for clarity. For comparison, epifluorescence images of localised *Bacillus subtilis* spores (lower right) are shown. The black box signifies dust on the lens.
Figure 22:
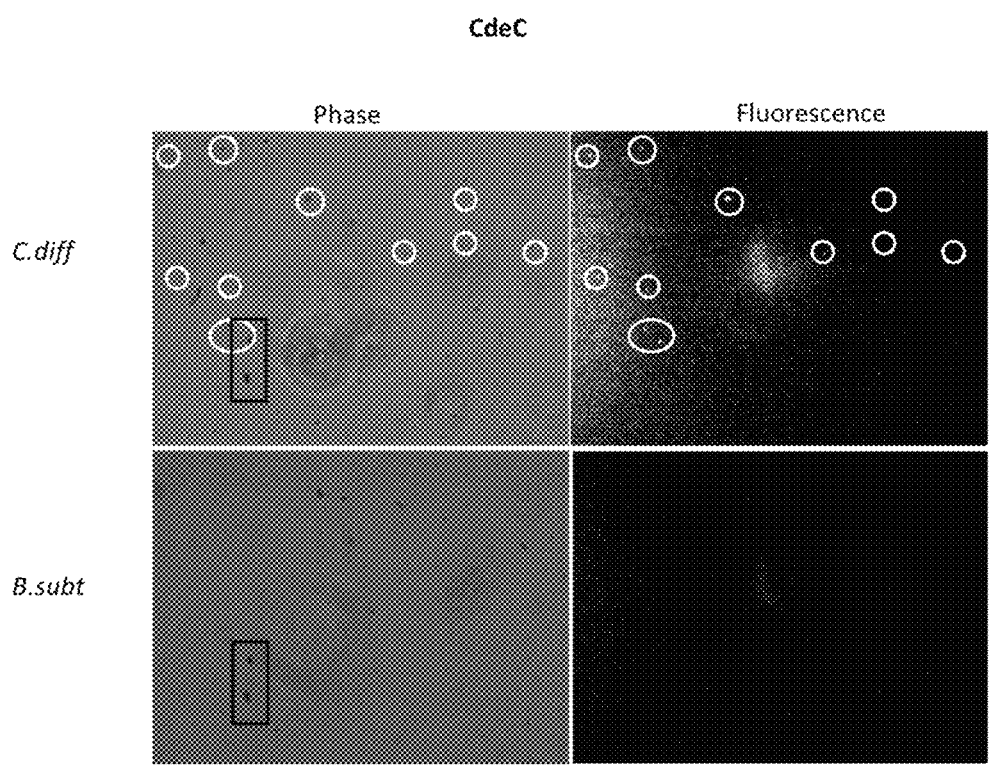
FIG. 22 shows brightfield images (left) and epifluorescence images (right) according to some embodiments of the present disclosure. *C. difficile* spores are localised to the upper images and *B. subtilis* spores are localised to the lower images. Epifluorescence images of localised *C. difficile* spores (upper right) show spots of fluorescence which colocalise with *C. difficile* spores, which is indicative of binding of the fluorescently labelled aptamer population selected against CdeC to the *C. difficile* spores. Spores showing fluorescent signals are highlighted with circles for clarity. For comparison, epifluorescence images of localised *Bacillus subtilis* spores (lower right) are shown. The black box signifies dust on the lens.
Figure 23:
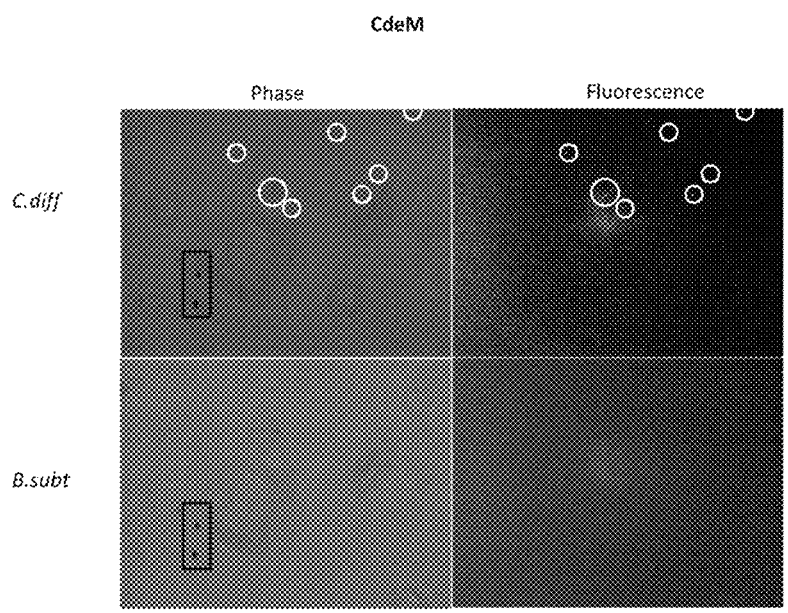
FIG. 23 shows brightfield images (left) and epifluorescence images (right) according to some embodiments of the present disclosure. *C. difficile* spores are localised to the upper images and *B. subtilis* spores are localised to the lower images. Epifluorescence images of localised *C. difficile* spores (upper right) show spots of fluorescence which colocalise with *C. difficile* spores, which is indicative of binding of the fluorescently labelled aptamer population selected against CdeM to the *C. difficile* spores. Spores showing fluorescent signals are highlighted with circles for clarity. For comparison, epifluorescence images of localised *Bacillus subtilis* spores (lower right) are shown. The black box signifies dust on the lens.
Figure 24:
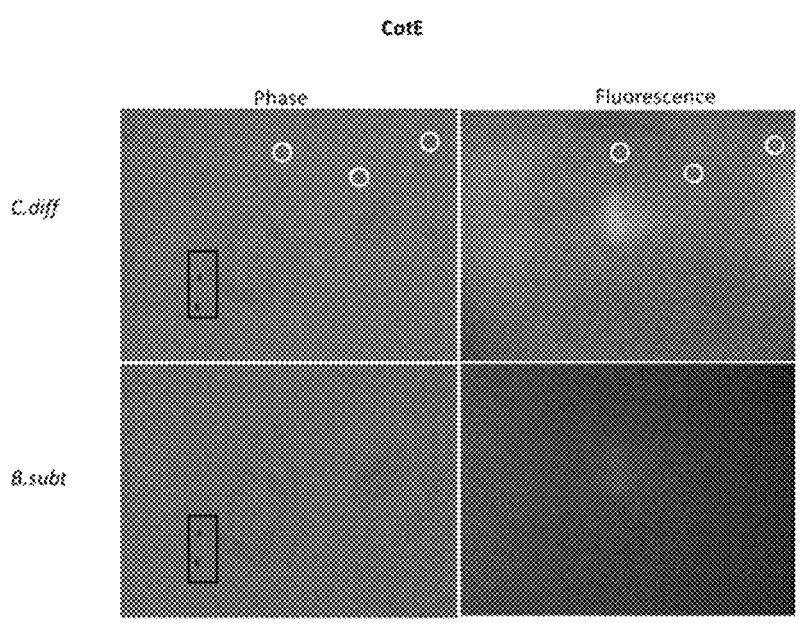
FIG. 24 shows brightfield images (left) and epifluorescence images (right) according to some embodiments of the present disclosure. *C. difficile* spores are localised to the upper images and *B. subtilis* spores are localised to the lower images. Epifluorescence images of localised *C. difficile* spores (upper right) shows spots of fluorescence which colocalise with *C. difficile* spores, which is indicative of binding of the fluorescently labelled aptamer population selected against CotE to the *C. difficile* spores. Spores showing fluorescent signals are highlighted with circles for clarity. For comparison, epifluorescence images of localised *Bacillus subtilis* spores (lower right) are shown. The black box signifies dust on the lens.
Figures 25A, 25B:
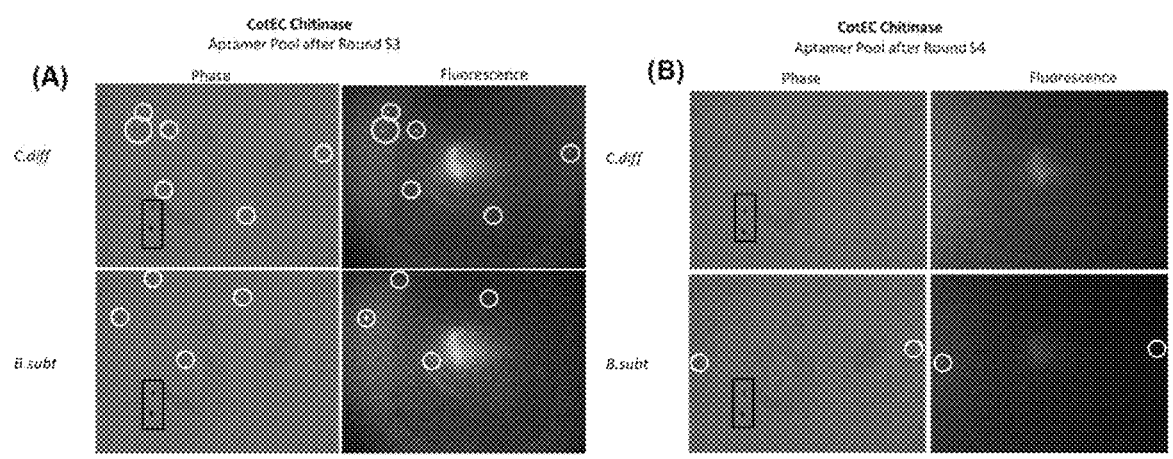
FIGS. 25A and 25B show brightfield images (left) and epifluorescence images (right) according to some embodiments of the present disclosure. *C. difficile* spores are localised to the upper images and *B. subtilis* spores are localised to the lower images. Epifluorescence images of localised *C. difficile* spores (upper right) show spots of fluorescence which colocalise with *C. difficile* spores which is indicative of binding of the fluorescently labelled aptamer population selected against CotEC Chitinase to the *C. difficile* spores. Spores showing fluorescent signals are highlighted with circles for clarity. For comparison, epifluorescence images of localised *Bacillus subtilis* spores (lower right) are shown.
Figure 26:
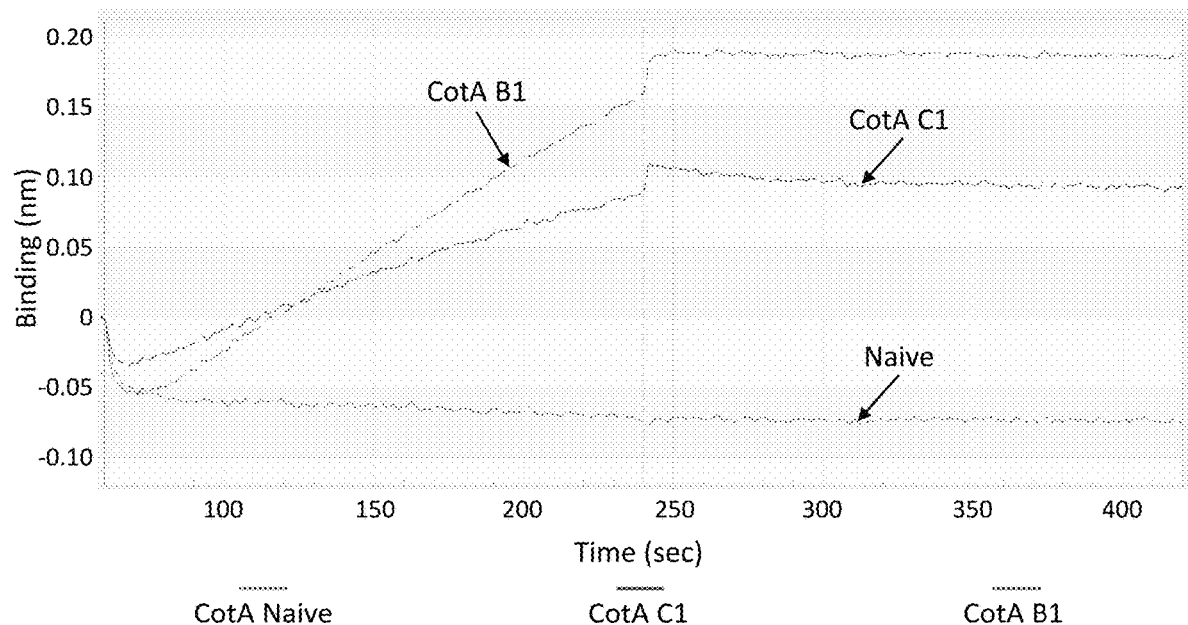
FIG. 26 shows Biolayer Interferometry (BLI) data comparing interactions between immobilized CotA and the naïve library (Naive) or immobilized CotA and the monoclonal aptamers: CotA C1 (CotA C1) and CotA B1 (CotA B1) according to some embodiments of the present disclosure.
Figure 27:
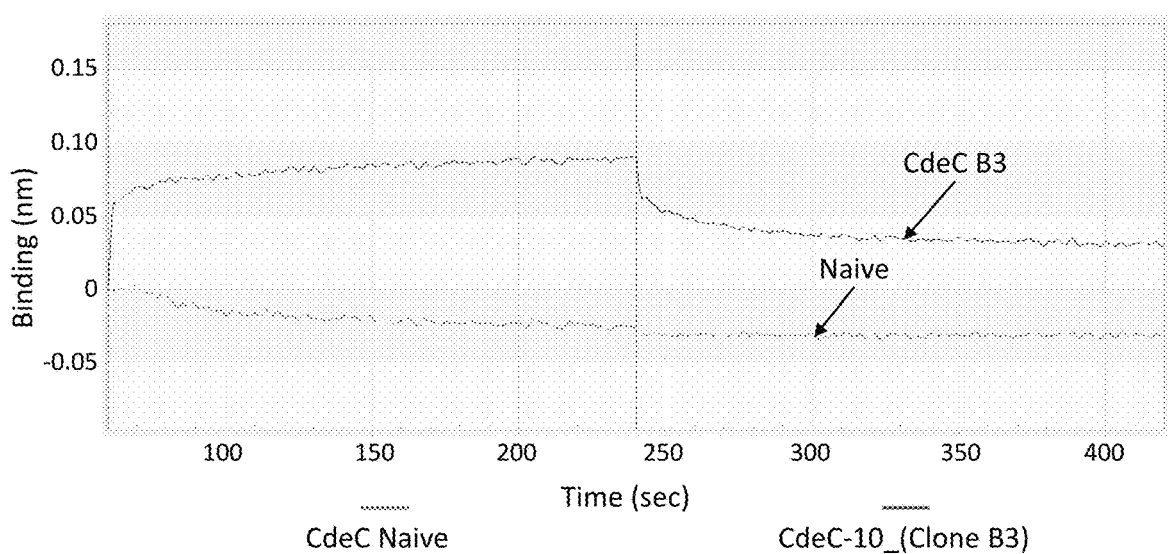
FIG. 27 shows Biolayer Interferometry (BLI) data comparing interactions between immobilized CdeC and the naïve library (Naive) or immobilized CdeC and the monoclonal aptamer CdeC B3 (CdeC B3) according to some embodiments of the present disclosure.
Figure 28:
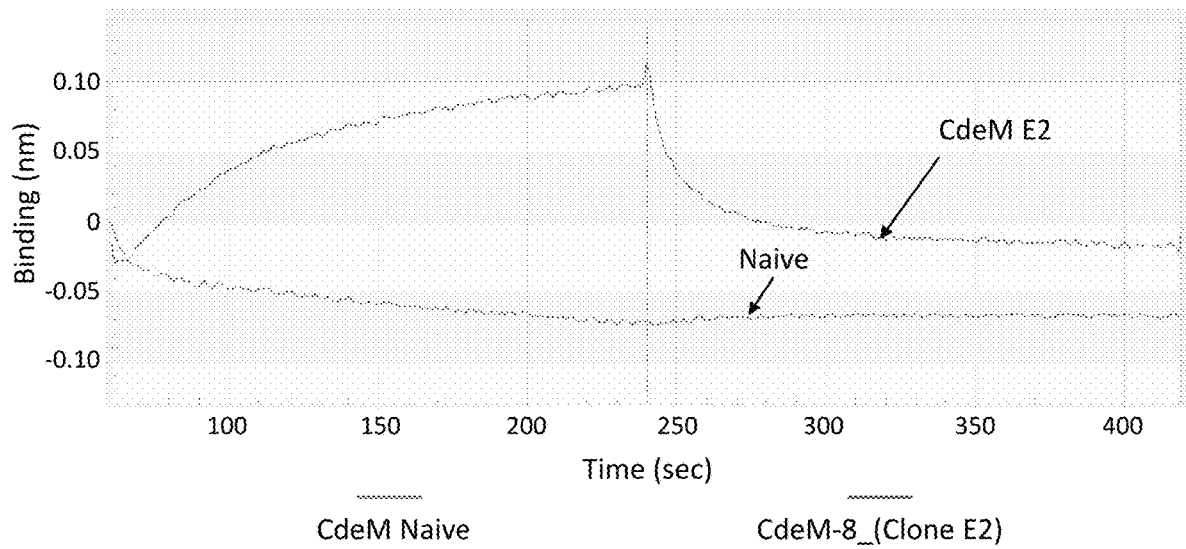
FIG. 28 shows Biolayer Interferometry (BLI) data comparing interactions between immobilized CdeM and the naïve library (Naive) or immobilized CdeM and the monoclonal aptamer CdeM E2 (CdeM E2) according to some embodiments of the present disclosure.
Figure 29:
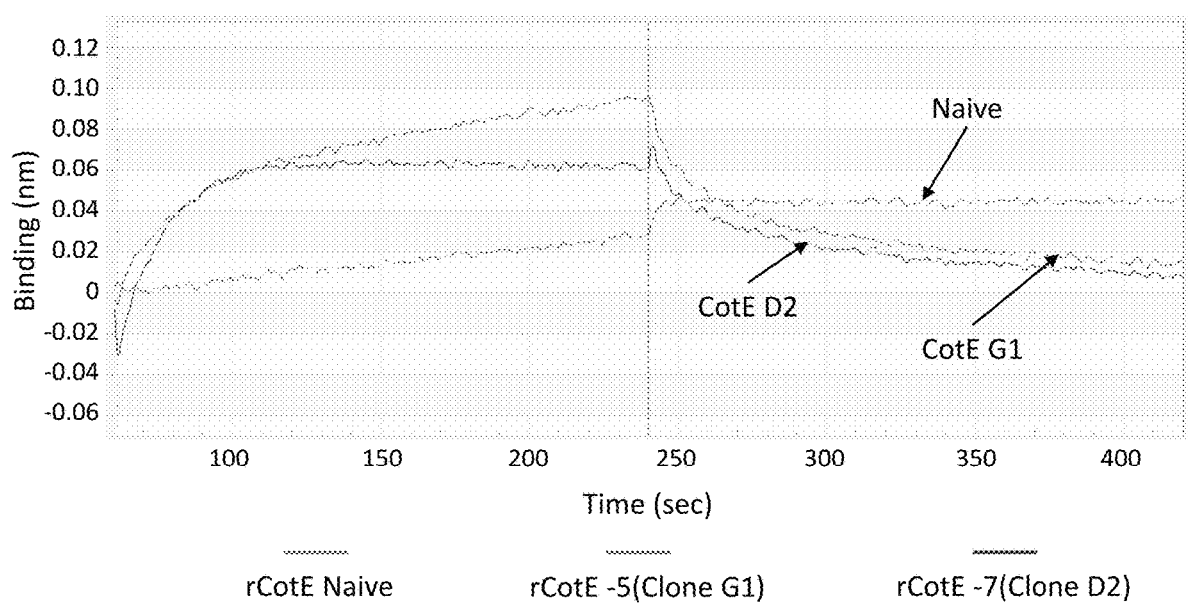
FIG. 29 shows Biolayer Interferometry (BLI) data comparing interactions between immobilized CotE and the naïve library (Naive) or immobilized CotE and the monoclonal aptamers: CotE D2 (CotE D2) and CotE G1 (CotE G1) according to some embodiments of the present disclosure.
Figure 30:
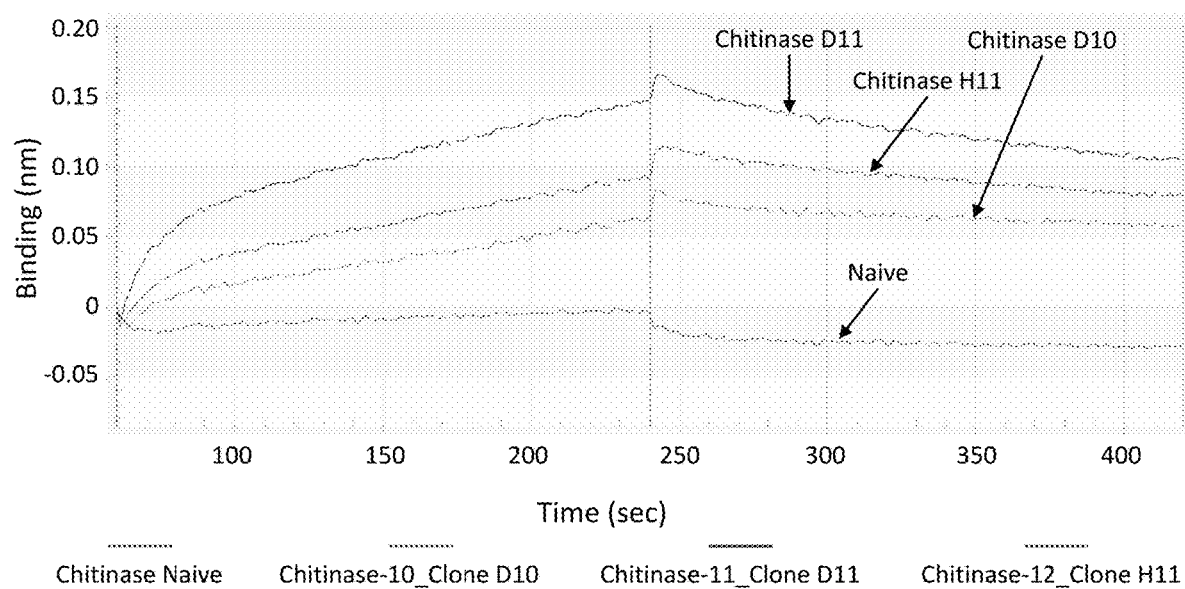
FIG. 30 shows Biolayer Interferometry (BLI) data comparing interactions between immobilized CotEC Chitinase and the naïve library (Naive) or immobilized CotEC Chitinase and the monoclonal aptamers: Chitinase D11 (Chitinase D11), Chitinase D10 (Chitinase D10), and Chitinase H11 (Chitinase H11) according to some embodiments of the present disclosure.
Figure 31A:
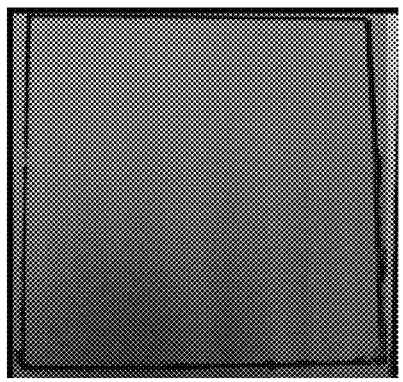
FIG. 31A-FIG. 31E show photographs of test samples on a stainless-steel surface under ambient light conditions without Polilight Flare+2 forensic light (505 nm) and without a 590 nm bandpass filter according to some embodiments of the present disclosure. For comparison.
Figure 31B:
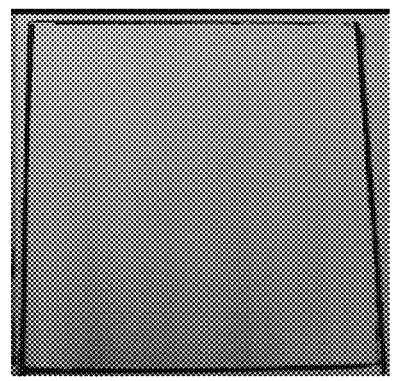
Figure 31C:
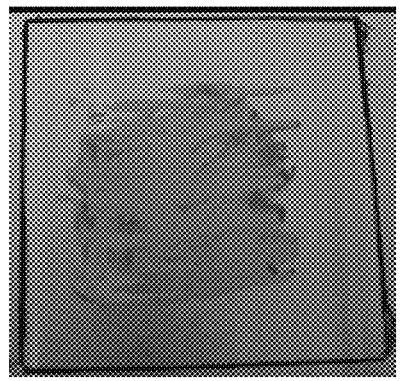
Figure 31D:
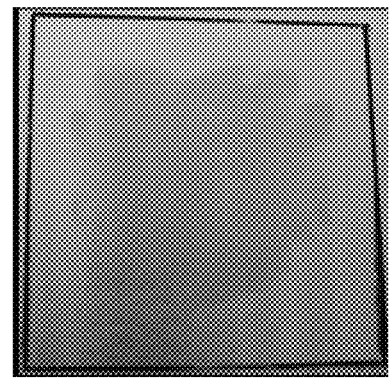
Figure 31E:
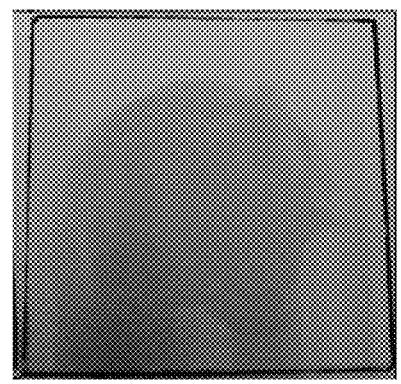

*Clostridium difficile* (also referred to as *C. difficile*) is a Gram-positive, anaerobic spore former and is an important nosocomial and community-acquired pathogenic bacterium. *C. difficile* infections (CDI) are a leading cause of infections worldwide with elevated rates of morbidity and mortality. Despite the fact that two major virulence factors, the enterotoxin TcdA and the cytotoxin TcdB, are essential in the development of CDI, *C. difficile* spores are the main vehicle of infection, and persistence and transmission of CDI, and are thought to play an essential role in episodes of CDI recurrence and horizontal transmission.

*Clostridium difficile* bacteria are found throughout the environment e.g. in soil, air, water, food products and human and animal faeces. A small number of people carry *C. difficile* in their intestinal tract without showing any symptoms. However, in other subjects, infection from *C. difficile* can cause symptoms ranging from diarrhea to life-threatening inflammation of the colon. Complications of *C. difficile* infection can include dehydration, kidney failure, toxic megacolon, perforation of the bowel and even death if the infection is not controlled quickly.

*Clostridium difficile* bacteria commonly affect older adults in hospitals or long-term care facilities. Subjects at greater risk of contracting *C. difficile* include but are not limited to those who have taken antibiotics, those with a compromised immune system, and those who have undergone abdominal or gastrointestinal surgery. For example, the mortality rate of *C. difficile* infection can be up to 25% in frail, elderly people in hospitals, and it has been postulated that antibiotic therapy disrupts normal gut microbiota, allowing *C. difficile* colonization and growth because it is naturally resistant to many drugs used to treat other infections, thereby enabling its toxin production.

An increase of *C. difficile* infections in subjects previously considered to be low-risk, for example, younger and otherwise healthy individuals without exposure to health care facilities, has also been seen in recent years. A new strain of *C. difficile*, Type 027, has recently been identified, which has been shown to produce more toxins than most other types of *C. difficile* causing a greater proportion of severe disease and apparent higher mortality.

First-line therapy for treating adults with CDI in the U.S. is vancomycin (125 mg, 4 times a day for 10 days) or fidaxomicin (200 mg, twice daily for 10 days) for both severe and non-severe CDI. In the UK, metronidazole (400 mg or 500 mg, 3 times daily for 10-14 days) is considered to be the first-line for treating first episodes of mild to moderate *C. difficile* infection; and, vancomycin (125 mg 4 times daily for 10-14 days) is considered for second episodes or if the infection is severe. An infection is defined as severe when there is a raised temperature or white cell count, rising creatinine, or signs or symptoms of severe colitis. Vancomycin may also be used in infections caused by the type 027 strain. If infection recurs, vancomycin or fidaxomicin (200 mg twice daily for 10 days) may be used. In some severe cases, a person might have to have surgery to remove the infected part of the intestines.

Spores from *C. difficile* are passed in faeces and can be transmitted to food, surfaces and objects via unwashed hands. The spores can persist for weeks or months on surfaces and transmitted via contact with such surfaces.

Given the rise in antibiotic resistance and the potential mortality associated with *C. difficile* infection, control measures are of the highest importance. Current measures include healthcare providers such as nurses and doctors following protocols including:

Cleaning hands with soap and water or an alcohol-based hand rub before and after caring for every patient to prevent *C. difficile* and other germs from being passed from one patient to another on their hands.

Carefully cleaning hospital rooms and medical equipment that have been used for patients with CDI.

Giving patients antibiotics only when necessary.

Using Contact Precautions to prevent *C. difficile* from spreading to other patients. Contact Precautions mean:

Whenever possible, keeping patients with *C. difficile* in a single room or in a room with another patient who has *C. difficile*.

Wearing of gloves and a gown over clothing by healthcare providers while taking care of patients with *C. difficile*.

Wearing of gloves and a gown by visitors.

Removing of gloves and gown, and cleaning hands when leaving the room of a patient with *C. difficile*.

Patients on Contact Precautions are asked to stay in their hospital rooms as much as possible. They can go to other areas of the hospital for treatments and tests.

Despite these preventative measures, *C. difficile* remains a significant healthcare issue and therefore there is a need for rapid identification of the presence of *C. difficile* in an environment in order to minimize its spread.

Embodiments disclosed herein may at least partially mitigate some of the problems identified in the prior art.

Embodiments disclosed herein may provide methods and products which have utility in the detection of *C. difficile*.

Further features of embodiments of the present invention are described below. The practice of embodiments of the present invention will employ, unless otherwise indicated, conventional techniques of molecular biology, microbiology, recombinant DNA technology and immunology, known to one of ordinary skill in the art.

Most general molecular biology, microbiology recombinant DNA technology and immunological techniques can be found in Sambrook et al, Molecular Cloning, A Laboratory Manual (2001) Cold Harbor-Laboratory Press, Cold Spring Harbor, N.Y. or Ausubel et al., Current protocols in molecular biology (1990) John Wiley and Sons, N.Y. Unless defined otherwise, all technical and scientific terms used herein have the same meaning as commonly understood by one of ordinary skill in the art to which this disclosure belongs. For example, the Concise Dictionary of Biomedicine and Molecular Biology, Juo, Pei-Show, 2nd ed., 2002, CRC Press; The Dictionary of Cell and Molecular Biology, 3rd ed., Academic Press; and the Oxford University Press, provide a person skilled in the art with a general dictionary of many of the terms used in this disclosure.

Units, prefixes and symbols are denoted in their Système International d' Unités (SI) accepted form. Numeric ranges are inclusive of the numbers defining the range. Unless otherwise indicated, amino acid sequences are written left to right in amino to carboxy orientation and nucleic acid sequences are written left to right in 5' to 3' orientation.

In the following, embodiments are explained in more detail by means of non-limiting examples. In the non-limiting, exemplary experiments, standard reagents and buffers free from contamination were used unless stated otherwise.

Embodiments comprise aptamers capable of specifically binding to *C. difficile*.

In certain embodiments, the *C. difficile* is a strain selected from SH11 (ribotype RT078), Type 027 and ATCC® 43598. In certain embodiments, the aptamer is capable of binding to a *C. difficile* spore of strain SH11. In certain embodiments, the aptamer is capable of binding to a *C. difficile* spore of strain Type 027. In certain embodiments, the aptamer is capable of binding to a *C. difficile* spore of strain ATCC® 43598.

Embodiments relate to aptamers which bind to a *C. difficile* spore. Embodiments comprise an aptamer that binds to a *C. difficile* spore coat protein.

*C. difficile* produces metabolically dormant spores. The spores comprise an outermost exosporium layer which may comprise a number of surface proteins. The exosporium layer may comprise one or more proteins selected from BclA1, BclA2, BclA3, CdeA, CdeB, CdeC and CdeM. Five coat proteins, cotA, cotB, cotCB, cotD, and cotE, were shown to be expressed on the outer coat layers of the spore.

One or more of these proteins may be a target of one or more aptamer herein, and binding to one or more of them by one or more aptamer herein may be a basis for a method of detecting *C. difficile* herein.

In some embodiments, the aptamer specifically binds to a *C. difficile* spore coat protein as listed in Table 1 below:

TABLE 1

| | |
|---|---|
| CotA | SEQ ID NO: 15 |
| Cot E | SEQ ID NO: 16 |
| CotEC | SEQ ID NO: 17 |

TABLE 1-continued

| | |
|---|---|
| CdeC | SEQ ID NO: 18 |
| CdeM | SEQ ID NO: 19 |

Target Proteins

In an embodiment, the aptamer specifically binds to a target as defined herein. The term "target" as used herein is used to relate to a molecule selected from at least one of a *C. difficile* CotA protein, *C. difficile* CotE protein, *C. difficile* CdeC protein, *C. difficile* CdeM protein, *C. difficile* CotEC chitinase protein, and a *C. difficile* spore. As used herein, the terms "target protein" and "target peptide" are used interchangeably.

In some embodiments, the aptamer is selected against a whole *C. difficile* spore. Thus, in some embodiments, the aptamer selectively binds to a *C. difficile* spore.

In some embodiments, the aptamer specifically binds to a surface protein of the exosporium layer of the *C. difficile* spore (e.g. CdeC, CdeM). In some embodiments, the aptamer specifically binds to a coat protein of the *C. difficile* spore (e.g. CotA, CotE, CotEC).

In some embodiments, the target proteins can be naturally occurring target proteins or recombinant target proteins listed at Table 2 and may be a target of one or more aptamers described herein:

TABLE 2

| Target Protein | SEQ ID NO: |
|---|---|
| CotA | 15 |
| Cot E | 16 |
| rCotEC | 17 |
| CdeC | 18 |
| CdeM | 19 |
| rCotE (LS25) | 20 |

CdeC

In some embodiments, the aptamer specifically binds to a *C. difficile* CdeC protein. The amino acid sequence of CdeC is published under UniProtKB—Q18AS2 (Q18AS2_PEPD6) version 1 and is as set forth in FIG. 1 (SEQ ID NO: 18).

In some embodiments, the aptamer binds to an epitope of the CdeC protein which is conserved between *C. difficile* strains. Thus, in some embodiments, the aptamer is used to detect a plurality of *C. difficile* strains in a sample.

CdeM

In some embodiments, the aptamer selectively binds to an amino acid sequence of a *C. difficile* surface-bound CdeM protein. CdeM is a cysteine rich protein which is understood to be required for the morphogenesis of the coat and exosporium layer of spores. An amino acid sequence of a *C. difficile* protein is published under UniProtKB—A0A3T1GTU1 (A0A3T1GTU1_CLODI) (version 1) and shown in FIG. 2 (SEQ ID NO: 19).

In some embodiments, the aptamer binds to an epitope of the CdeM protein which is conserved between *C. difficile* strains. Thus, in some embodiments, the aptamer is used to detect a plurality of *C. difficile* strains in a sample.

In some embodiments, the spores comprise a spore coat. The spore coat may comprise a plurality of proteins including, but not limited to CotA and CotB for example.

CotA

In some embodiments, the aptamer specifically binds to a protein encoded by a *C. difficile* CotA gene. The protein may be referred to herein as either CotA or "spore coat assembly protein".

An amino acid sequence of CotA is published under UniProtKB Accession No. Q186G8 (Q186G8_PEPD6) version 1 and shown in FIG. 3 (SEQ ID NO: 15).

CotE and CotEC Chitinase

Figure 4:
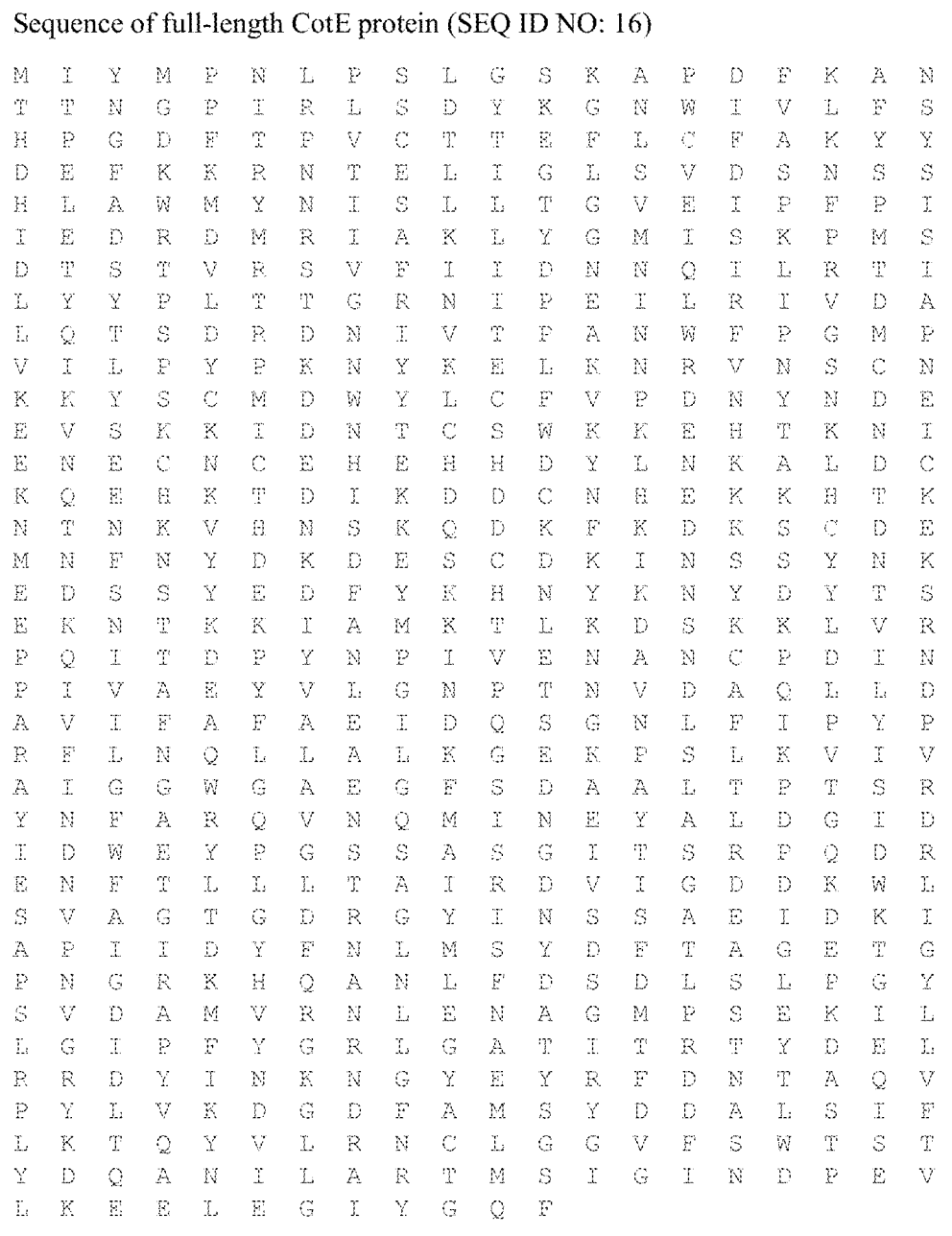

In some embodiments, the aptamer specifically binds to a *C. difficile* protein encoded by a CotE gene. An amino acid sequence of a CotE protein (also referred to as peroxiredoxin) is published under accession number UniProtKB—Q18BV5 (Q18BV5_PEPD6) and is shown in FIG. 4 (SEQ ID NO: 16).

Figure 5A:
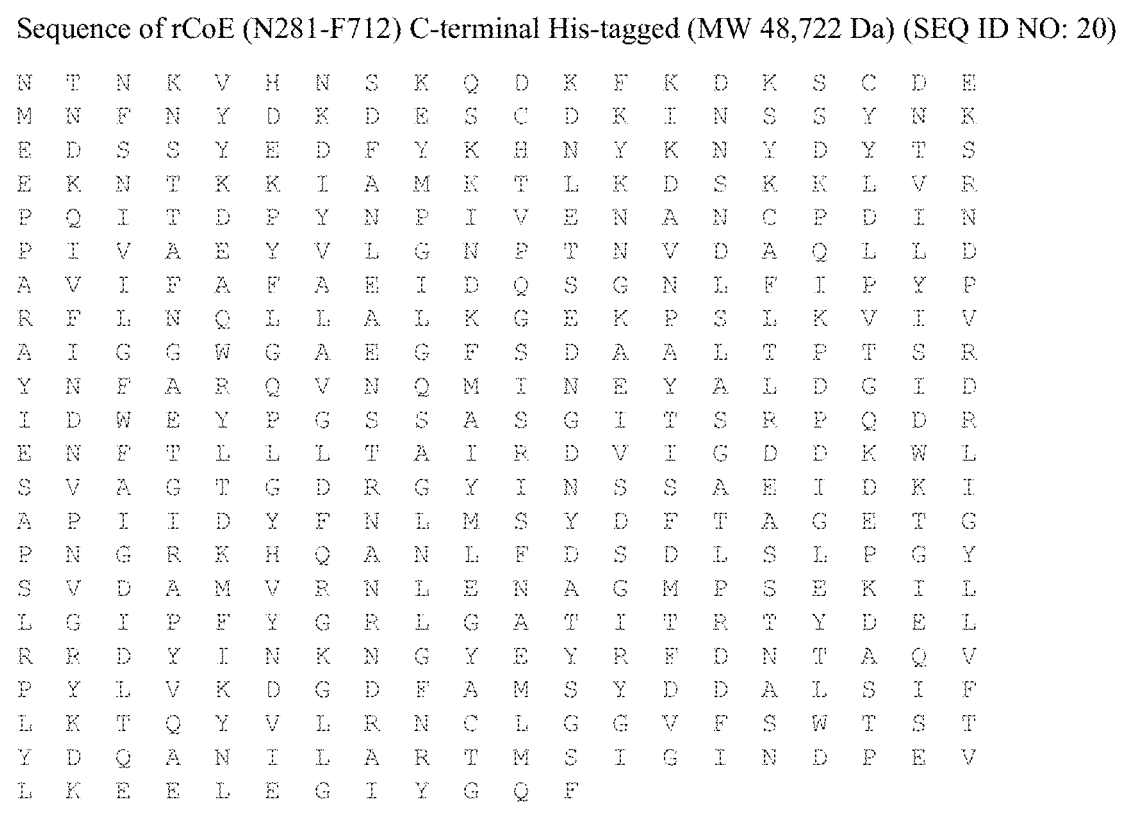

In some embodiments, aptamers were raised to a recombinant form of CotE referred to as "rCotE" (also referred to as LS25). The amino acid sequence of rCotE is shown in FIG. 5A and consists of amino acid residues N281-F712 (SEQ ID NO: 20). The recombinant protein comprises a chitinase domain and a sequence unique to CotE, as shown in FIG. 5A.

Figure 5B:
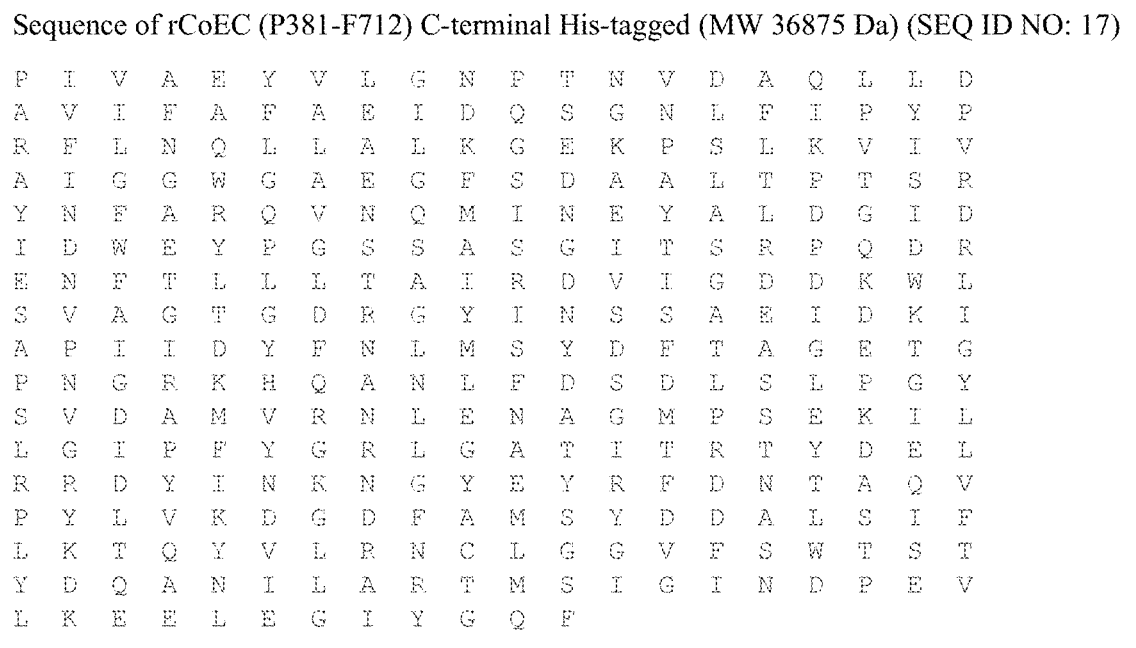

In some embodiments, the aptamer specifically binds to a recombinant *C. difficile* protein referred to as "rCotEC" (also referred to as AB45). The amino acid sequence of rCotEC is shown in FIG. 5B and consists of amino acid residues N381-F712 (SEQ ID NO: 17).

In some embodiments, the aptamers are selected against a tagged rCotEC protein, including but not limited to His-tagged rCotEC protein.

In some embodiments, the aptamers are selected against a tagged recombinant *C. difficile* protein including but not limited to His-tagged *C. difficile* protein. Other protein tags commonly used in the art to assist with protein purification may be used as well.

In some embodiments, the aptamer is selected against a whole *C. difficile* spore. Thus, in some embodiments, the aptamer selectively binds to a *C. difficile* spore.

In an embodiment, the aptamer specifically binds to an epitope in a *C. difficile* CotA protein.

In an embodiment, the aptamer specifically binds to an epitope in a *C. difficile* CotE protein.

In an embodiment, the aptamer specifically binds to an epitope in a *C. difficile* CdeC protein.

In an embodiment, the aptamer specifically binds to an epitope in a *C. difficile* CdeM protein.

In an embodiment, the aptamer specifically binds to an epitope in a *C. difficile* CotEC chitinase protein.

An aptamer binds "specifically" to a target as defined herein if the aptamer binds with preferential or high affinity to the target protein but does not bind or binds with only low affinity to other structurally related molecules (e.g. *Bacillus subtilis* spores.) In some embodiments, the dissociation constant for the target protein is in the micro-molar range. In some embodiments, the dissociation constant for the target protein is in the nano-molar range. In some embodiments, the dissociation constant for the target protein is in the pico-molar range. In some embodiments, the dissociation constant is about 0.1 nM or less. In some embodiments, the dissociation constant is about 0.1 nM to about 1 nM. In some embodiments, the dissociation constant is about 1 nM to about 10 nM. In some embodiments, the dissociation constant is about 10 nM to about 100 nM. In some embodiments, the dissociation constant is about 100 nM to about 1000 nM. Lower affinity binding may refer to binding that occurs at less affinity than to a target protein. The lower affinity binding may be selected from the range of less than 1 fold to 2 fold, less than 2 fold to 5 fold, less than 5 fold to 10 fold, less than 10 fold to 50 fold, less than 50 fold to 100 fold, less than 100 fold to 1000 fold, less than 1000 fold to 10000 fold, or less than 10000 fold to 100000 fold of binding to the target protein.

Aptamers

The aptamers described herein are small artificial ligands, compromising DNA, RNA or modifications thereof, capable of specifically binding to a target as defined herein with high affinity and specificity.

As used herein, "aptamer," "nucleic acid molecule," or "oligonucleotide" are used interchangeably to refer to a non-naturally occurring nucleic acid molecule that has a desirable action on a target as defined herein.

In some embodiments, the aptamers may be DNA aptamers. For example, the aptamers may be formed from single-stranded DNA (ssDNA). In some embodiments, the aptamers may be RNA aptamers. For example, the aptamers can be formed from single-stranded RNA (ssRNA).

In some embodiments, there is provided an aptamer comprising a nucleic acid sequence selected from a nucleic acid sequence as set forth in Table 3.

TABLE 3

Aptamer Sequences

| Sequence |
|---|
| *CCAGTGTAGACTACTCAATGC*TCTTACGATCCTCACCTGCTAGCACACCCATATCCCATGC*GTACTATCCACAGGTCAACC* (SEQ ID NO: 1) |
| *CCAGTGTAGACTACTCAATGC*GGGTTGCGACATGGTGGTAAGAGCTCAGCCCGTTCCCATA*GTACTATCCACAGGTCAACC* (SEQ ID NO: 2) |
| *CCAGTGTAGACTACTCAATGC*ACGGCCTGTTCGTAAGACCCTTACAGACTAGTTTTTCCCT*GTACTATCCACAGGTCAACC* (SEQ ID NO: 3) |
| *CCAGTGTAGACTACTCAATGC*CCTATTAGCTGTATCGATCCGTTTAGTCGCTCCTCCGATA*GTACTATCCACAGGTCAACC* (SEQ ID NO: 4) |
| *CCAGTGTAGACTACTCAATGC*CTGGTAAATCGATGACCGCTGCCTCGCCTGAGTAATCATC*GTACTATCCACAGGTCAACC* (SEQ ID NO: 5) |
| *CCAGTGTAGACTACTCAATGC*CGTGGACTGGTCGGGTTTGGATTCGGCAGATGAATCAGTA*GTACTATCCACAGGTCAACC* (SEQ ID NO: 6) |

TABLE 3-continued

Aptamer Sequences

| Sequence |
|---|
| *CCAGTGTAGACTACTCAATGC*CTTGTAAGAAGAACAATCGCCGCTTCGCCTGAATAGGTTC*GTACTATCCACAGGTCAACC* (SEQ ID NO: 7) |
| *CCAGTGTAGACTACTCAATGC*GGACCGTTGCCTCGCCCGAGTAATCCGCCATCGCCTTTCC*GTACTATCCACAGGTCAACC* (SEQ ID NO: 8) |
| *CCAGTGTAGACTACTCAATGC*TTAAGTTCTGGGGACACGTGATGAACGCATTTAATGGGGC*GTACTATCCACAGGTCAACC* (SEQ ID NO: 9) |
| *CCAGTGTAGACTACTCAATGC*CGTGGACTGGTCGGGTTTGGATTCGGCAGATGAATCACTA*GTACTATCCACAGGTCAACC* (SEQ ID NO: 10) |
| *CCAGTGTAGACTACTCAATGC*GGCTGTGTGACTTGACCTTTGGAATGGGTGGGAGGGATGG*GTACTATCCACAGGTCAACC* (SEQ ID NO: 11) |
| *CCAGTGTAGACTACTCAATGC*GGTGTGGTGACCTTGACCTATGGAACCTGGTTGTA*GTACTATCCACAGGTCAACC* (SEQ ID NO: 12) |
| *CCAGTGTAGACTACTCAATGC*TCGACATTTCCGCCCCGACGGCCCTCCTAGTGATGGGAGA*GTACTATCCACAGGTCAACC* (SEQ ID NO: 13) |
| *CCAGTGTAGACTACTCAATGC*CTTCCATTCACCTACCGAGCTAAGCGTTCGACTTAGGTCT*GTACTATCCACAGGTCAACC* (SEQ ID NO: 14) |
| ATCGATGACCGCTGCCTCGCCTGAGTAATCATC*GTA* (SEQ ID NO: 23) |
| CCATACTCAATGCTCTTACGATCCTCATCAACC (SEQ ID NO: 24) |
| CCAGTGTAGACTACTCAATGCTCTTACGATCCTCATCAACC (SEQ ID NO: 25) |
| AGTGTAGACTACTCAATGCGGCTGGCCACAGGTCAACC (SEQ ID NO: 26) |

Primer regions are indicated in bold and italic:

TABLE 4

| ID | Sequence | Target |
|---|---|---|
| C. diff_F1 | *CCAGTGTAGACTACTCAATGC*TCTTACGATCCTCACCTGCTAGCACACCCATATCCCATGC*GTACTATCCACAGGTCAACC* (SEQ ID NO: 1) | C. diff spores |
| C. diff_G1 | *CCAGTGTAGACTACTCAATGC*GGGTTGCGACATGGTGGTAAGAGCTCAGCCCGTTCCCATA*GTACTATCCACAGGTCAACC* (SEQ ID NO: 2) | C. diff spores |
| C. diff_E2 | *CCAGTGTAGACTACTCAATGC*ACGGCCTGTTCGTAAGACCCTTACAGACTAGTTTTTCCCT*GTACTATCCACAGGTCAACC* (SEQ ID NO: 3) | C. diff spores |
| Chitinase_D10 | *CCAGTGTAGACTACTCAATGC*CCTATTAGCTGTATCGATCCGTTTAGTCGCTCCTCCGATA*GTACTATCCACAGGTCAACC* (SEQ ID NO: 4) | CotEC Chitinase |
| Chitinase_D11 | *CCAGTGTAGACTACTCAATGC*CTGGTAAATCGATGACCGCTGCCTCGCCTGAGTAATCATC*GTACTATCCACAGGTCAACC* (SEQ ID NO: 5) | CotEC Chitinase |
| CdeC_D1 | *CCAGTGTAGACTACTCAATGC*CGTGGACTGGTCGGGTTTGGATTCGGCAGATGAATCAGTA*GTACTATCCACAGGTCAACC* (SEQ ID NO: 6) | CdeC |
| Chitinase_H11 | *CCAGTGTAGACTACTCAATGC*CTTGTAAGAAGAACAATCGCCGCTTCGCCTGAATAGGTTC*GTACTATCCACAGGTCAACC* (SEQ ID NO: 7) | CotEC Chitinase |

TABLE 4-continued

| ID | Sequence | Target |
|---|---|---|
| Chitinase_D7 | *CCAGTGTAGACTACTCAATGC*GGACCGTTGCCT CGCCCGAGTAATCCGCCATCGCCTTTCC*GTACT ATCCACAGGTCAACC* (SEQ ID NO: 8) | CotEC Chitinase |
| CotA_B1 | *CCAGTGTAGACTACTCAATGC*TTAAGTTCTGGG GACACGTGATGAACGCATTTAATGGGGC*GTACT ATCCACAGGTCAACC* (SEQ ID NO: 9) | CotA |
| CotA_C1 | *CCAGTGTAGACTACTCAATGC*CGTGGACTGGT CGGGTTTGGATTCGGCAGATGAATCACTA*GTAC TATCCACAGGTCAACC* (SEQ ID NO: 10) | CotA |
| CotE_H2 | *CCAGTGTAGACTACTCAATGC*GGCTGTGTGACT TGACCTTTGGAATGGGTGGGAGGGATGG*GTACT ATCCACAGGTCAACC* (SEQ ID NO: 11) | CotE |
| CotE_E2 | *CCAGTGTAGACTACTCAATGC*GGTGTGGTGAC CTTGACCTATGGAACCTGGTTGTA*GTACTATCC ACAGGTCAACC* (SEQ ID NO: 12) | CotE |
| CotE_D2 | *CCAGTGTAGACTACTCAATGC*TCGACATTTCCG CCCCGACGGCCCTCCTAGTGATGGGGAGA*GTAC TATCCACAGGTCAACC* (SEQ ID NO: 13) | CotE |
| CdeM_E2 | *CCAGTGTAGACTACTCAATGC*CTTCCATTCACC TACCGAGCTAAGCGTTCGACTTAGGTCT*GTACT ATCCACAGGTCAACC* (SEQ ID NO: 14) | CdeM |
| Chitinase_D11 | ATCGATGACCGCTGCCTCGCCTGAGTAATCATC*G TA* (SEQ ID NO: 23) | CotEC Chitinase |
| C. diff_F1 | CCATACTCAATGCTCTTACGATCCTCATCAACC (SEQ ID NO: 24) | C. diff spores |
| C. diff_G1 | CCAGTGTAGACTACTCAATGCTCTTACGATCCTC ATCAACC (SEQ ID NO: 25) | C. diff spores |
| CotE_H2 | AGTGTAGACTACTCAATGCGGCTGGCCACAGGT CAACC (SEQ ID NO: 26) | CotE |

In some embodiments, the aptamers are RNA aptamers and comprise a sequence in which one or some or all of the deoxyribonucleotides in any of the sequences set forth in SEQ ID NO. 1 to 14 and SEQ ID NO: 23 to 26 are substituted for their equivalent ribonucleotide residues AMP, GMP, UMP or CMP.

The aptamers of embodiments of the invention may comprise modified nucleic acids as described herein.

In some embodiments, the aptamers of the invention are prepared using principles of in vitro selection known in the art, that include iterative cycles of target binding, partitioning and preferential amplification of target binding sequences. Selection may be performed using immobilized target proteins. Immobilization may include, but is not limited to, immobilization to a solid surface. In a non-limiting example, the solid surface may be beads. In a non-limiting example, the solid surface may be magnetic beads.

Non-limiting examples of amplification methods include polymerase chain reaction (PCR), ligation amplification (or ligase chain reaction, LCR), strand displacement amplification, nucleic acid sequence-based amplification, and amplification methods based on the use of Q-beta replicase. In a non-limiting embodiment, at least one type of aptamer may be immobilized on a solid surface during amplification. Each of these exemplary methods is well known in the art.

In some embodiments, the aptamers are selected from a nucleic acid molecule library such as a single-stranded DNA or RNA nucleic acid molecule library. The aptamers may be selected from a "universal aptamer selection library" that is designed such that any selected aptamers need little to no adaptation to convert into any of the listed assay formats.

Once selected, the aptamer may be further modified before being used e.g. to remove one or both primer sequences and/or parts of the randomised sequence not required for target binding.

Typically, aptamers of the embodiments of the invention comprise a first primer region (e.g. at the 5' end), a second primer region (e.g. at the 3' end), or both. The primer regions may serve as primer binding sites for PCR amplification of the library and selected aptamers.

The skilled person would understand different primer sequences can be selected depending, for example, on the starting library and/or aptamer selection protocol. In some embodiments, the primer comprises or consists of a nucleic acid sequence of SEQ ID NO: 21 and/or 22. In an embodiment, aptamers may comprise SEQ ID NO: 21 and/or 22. In other embodiments, any one of one to all of the nucleotides disclosed by SEQ ID NO: 21 or 22 may be modified. The primer region length may also be varied.

In some embodiments, the primers are shown in Table 5

TABLE 5

CCAGTGTAGACTACTCAATGC (primer) SEQ ID NO: 21

GTACTATCCACAGGTCAACC (primer) SEQ ID NO: 22

The first primer region and/or second region may comprise a detectable label as described herein. As used herein the terms "detectable label" and "detectable moiety" are used interchangeably. In an embodiment, the first and/or second primer region may be fluorescently labelled. Non-limiting examples of fluorescent labels include but are not limited to fluorescein, green fluorescent protein (GFP), yellow fluorescent protein, cyan fluorescent protein, and others. In an embodiment, a fluorescein label is used. In some embodiments, other forms of detecting the primer may be used, including but not limited to phosphate ($PO_4$) labelling, isotope labelling, electrochemical sensors, colorimetric biosensors, and others.

In some embodiments, the aptamers of the invention comprise or consist of a nucleic acid sequence selected from any one of SEQ ID NOs: 1 to 14.

In some embodiments, aptamers of the invention comprise or consist of a nucleic acid sequence having at least 85%, at least 90%, at least 95%, at least 96%, at least 97%, at least 98%, at least 99% or more sequence identity to the nucleotide sequence of any one of SEQ ID NOs: 1 to 14 or SEQ ID NOs: 23 to 26.

As used herein, "sequence identity" refers to the percentage of nucleotides in a candidate sequence that are identical with the nucleotides in said sequences after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, CLUSTALW or Megalign (DNASTAR) software. For example, % nucleic acid sequence identity values can be generated using sequence comparison computer programs found on the European Bioinformatics Institute website (www.ebi.ac.uk).

As used herein, when describing the percent identity of a nucleic acid, such as an aptamer, the sequence of which is at least, for example, about 90% identical to a reference nucleotide sequence, it is intended that the nucleic acid sequence is identical to the reference sequence except that the nucleic acid sequence may include up to ten point mutations (e.g. substitution, deletion, insertion) per each 100 nucleotides of the reference nucleic acid sequence. These mutations may occur at the 5' or 3' terminal positions of the reference nucleotide sequence or anywhere between those 5' or 3' terminal positions, interspersed either individually among nucleotides in the reference sequence or in one or more contiguous groups within the reference sequence.

In some embodiments, aptamers comprise, consist essentially of, or consist of a minimal effective fragment of SEQ ID NOs: 1 to 14 or SEQ ID NOs: 23-26. Herein, a "minimal effective fragment" is understood to mean a fragment (e.g. portion) of the full-length aptamer capable of binding to a target as defined herewith with the same or improved affinity as compared to the full-length aptamer. A minimal effective fragment may compete for binding to a target as defined herein with the full-length aptamer.

In some embodiments, the aptamers comprise, consist essentially of, or consist of at least 20 contiguous nucleic acid residues of any of the sequences as set forth in any one of SEQ ID NOs: 1 to 14 or SEQ ID NOs: 23-26 and show equivalent or improved binding to the target molecule. In some embodiments, the aptamers of the invention comprise, consist essentially of, or consist of at least 20 contiguous nucleic acid residues of any of the sequences as set forth in any one of SEQ ID NOs: 1 to 14 or SEQ ID NOs: 23-26 and show adequate binding to the target molecule. Adequate binding includes binding to target molecule that occurs with affinity and specificity as described herein, or an affinity and/or specificity of binding less than that of the full-length aptamer sequence above but still capable of delivering a report of the presence of its respective target.

In some embodiments, an aptamer of the invention comprises, consists essentially of, or consists of at least 25 contiguous nucleotides of any of the sequences as set forth in any one of SEQ ID NOs: 1 to 14 or SEQ ID NOs: 23-26.

In some embodiments, an aptamer comprises, consists essentially of, or consists of 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 contiguous nucleotides in the nucleic acid sequence of SEQ ID NO: 1. The aptamer may comprise, consist essentially of, or consist of any span of contiguous nucleotides from SEQ ID NO: 1, where the span has a length chosen in one nucleotide increments from 25 nucleotides to full length.

In some embodiments, the aptamer comprises, consists essentially of, or consists of 25, 26, 27, 28, 29, 30, 31, 32, 33, 34, 35, 36, 37, 38, 39, 40 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 contiguous nucleotides in the nucleic acid sequence of SEQ ID NO: 2. The aptamer may comprise, consist essentially of, or consist of any span of contiguous nucleotides from SEQ ID NO: 2, where the span has a length chosen in one nucleotide increments from 25 nucleotides to full length.

In some embodiments, the aptamer comprises, consists essentially of, or consists of 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 contiguous nucleotides in the nucleic acid sequence of SEQ ID NO: 3. The aptamer may comprise, consist essentially of, or consist of any span of contiguous nucleotides from SEQ ID NO: 3, where the span has a length chosen in one nucleotide increments from 25 nucleotides to full length.

In some embodiments, the aptamer comprises, consists essentially of, or consists of 25, 26, 27, 28, 29 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 contiguous nucleotides in the nucleic acid sequence of SEQ ID NO: 4. The aptamer may comprise, consist essentially of, or consist of any span of contiguous nucleotides from SEQ ID NO: 4, where the span has a length chosen in one nucleotide increments from 25 nucleotides to full length.

In some embodiments, the aptamer comprises, consists essentially of, or consists of 25, 26, 27, 28, 29 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 contiguous nucleotides in the nucleic acid sequence of SEQ ID NO: 5. The aptamer may comprise, consist essentially of, or consist of any span of contiguous nucleotides from SEQ ID NO: 5, where the span has a length chosen in one nucleotide increments from 25 nucleotides to full length.

In some embodiments, the aptamer comprises, consists essentially of, or consists of 25, 26, 27, 28, 29 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 contiguous nucleotides in the nucleic acid sequence of SEQ ID NO: 6. The aptamer may comprise, consist essentially of, or consist of any span of contiguous nucleotides from SEQ ID NO: 6, where the span has a length chosen in one nucleotide increments from 25 nucleotides to full length.

In some embodiments, the aptamer comprises, consists essentially of, or consists of 25, 26, 27, 28, 29 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 contiguous nucleotides in the nucleic acid sequence of SEQ ID NO: 7. The aptamer may comprise, consist essentially of, or consist of any span of contiguous nucleotides from SEQ ID NO: 7, where the span has a length chosen in one nucleotide increments from 25 nucleotides to full length.

In some embodiments, the aptamer comprises, consists essentially of, or consists of 25, 26, 27, 28, 29 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 contiguous nucleotides in the nucleic acid sequence of SEQ ID NO: 8. The aptamer may comprise, consist essentially of, or consist of any span of contiguous nucleotides from SEQ ID NO: 8, where the span has a length chosen in one nucleotide increments from 25 nucleotides to full length.

In some embodiments, the aptamer comprises, consists essentially of, or consists of 25, 26, 27, 28, 29 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 contiguous nucleotides in the nucleic acid sequence of SEQ ID NO: 9. The aptamer may comprise, consist essentially of, or consist of any span of contiguous nucleotides from SEQ ID NO: 9, where the span has a length chosen in one nucleotide increments from 25 nucleotides to full length.

In some embodiments, the aptamer comprises, consists essentially of, or consists of 25, 26, 27, 28, 29 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 contiguous nucleotides in the nucleic acid sequence of SEQ ID NO: 10. The aptamer may comprise, consist essentially of, or consist of any span of contiguous nucleotides from SEQ ID NO: 10, where the span has a length chosen in one nucleotide increments from 25 nucleotides to full length.

In some embodiments, the aptamer comprises, consists essentially of, or consists of 25, 26, 27, 28, 29 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 contiguous nucleotides in the nucleic acid sequence of SEQ ID NO: 11. The aptamer may comprise, consist essentially of, or consist of any span of contiguous nucleotides from SEQ ID NO: 11, where the span has a length chosen in one nucleotide increments from 25 nucleotides to full length.

In some embodiments, the aptamer comprises, consists essentially of, or consists of 25, 26, 27, 28, 29 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 contiguous nucleotides in the nucleic acid sequence of SEQ ID NO: 12. The aptamer may comprise, consist essentially of, or consist of any span of contiguous nucleotides from SEQ ID NO: 12, where the span has a length chosen in one nucleotide increments from 25 nucleotides to full length.

In some embodiments, the aptamer comprises, consists essentially of, or consists of 25, 26, 27, 28, 29 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 nucleotides in the nucleic acid sequence of SEQ ID NO: 13. The aptamer may comprise, consist essentially of, or consist of any span of contiguous nucleotides from SEQ ID NO: 13, where the span has a length chosen in one nucleotide increments from 25 nucleotides to full length.

In some embodiments, the aptamer comprises, consists essentially of, or consists of 25, 26, 27, 28, 29 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 contiguous nucleotides in the nucleic acid sequence of SEQ ID NO: 14. The aptamer may comprise, consist essentially of, or consist of any span of contiguous nucleotides from SEQ ID NO: 14, where the span has a length chosen in one nucleotide increments from 25 nucleotides to full length.

In some embodiments, the aptamer comprises, consists essentially of, or consists of 25, 26, 27, 28, 29, 30, 31, 32, 33, 34, 35, or 36 contiguous nucleotides in the nucleic acid sequence of SEQ ID NO: 23. The aptamer may comprise, consist essentially of, or consist of any span of contiguous nucleotides from SEQ ID NO: 23, where the span has a length chosen in one nucleotide increments from 25 nucleotides to full length.

In some embodiments, the aptamer comprises, consists essentially of, or consists of 25, 26, 27, 28, 29, 30, 31, 32 or 33 contiguous nucleotides in the nucleic acid sequence of SEQ ID NO: 24. The aptamer may comprise, consist essentially of, or consist of any span of contiguous nucleotides from SEQ ID NO: 24, where the span has a length chosen in one nucleotide increments from 25 nucleotides to full length.

In some embodiments, the aptamer comprises, consists essentially of, or consists of 25, 26, 27, 28, 29, 30, 31, 32, 33, 34, 35, 36, 37, 38, 39, 40, or 41 contiguous nucleotides in the nucleic acid sequence of SEQ ID NO: 25. The aptamer may comprise, consist essentially of, or consist of any span of contiguous nucleotides from SEQ ID NO: 25, where the span has a length chosen in one nucleotide increments from 25 nucleotides to full length.

In some embodiments, the aptamer comprises, consists essentially of, or consists of 25, 26, 27, 28, 29, 30, 31, 32, 33, 34, 35, 36, 37, or 38 contiguous nucleotides in the nucleic acid sequence of SEQ ID NO: 26. The aptamer may comprise, consist essentially of, or consist of any span of contiguous nucleotides from SEQ ID NO: 26, where the span has a length chosen in one nucleotide increments from 25 nucleotides to full length.

In some embodiments, these sequences relate to aptamer fragments with equivalent, suitable, or improved binding to a target protein as described herein as compared to full-length aptamer.

In some embodiments, aptamers comprise, consist essentially of, or consist of a nucleic acid sequence comprising at least about 30, 35, 40, 45, 50, 51, 52, 53, 54, 55, 60 or more consecutive nucleotides of a sequence having at least 85%, at least 90%, at least 95%, at least 96%, at least 97%, at least 98%, at least 99% or more identity with any of SEQ ID NOs: 1 to 14 or SEQ ID NOs: 23-26. In this context the term "about" typically means the referenced nucleotide sequence length plus or minus 10% of that referenced length.

In some embodiments, aptamers comprise, consist essentially of, or consist of a nucleic acid sequence comprising at least about 30, 35, 40, 45, 50, 55, 60, 65, 70, 75, 80 or more consecutive nucleotides of a sequence having at least 85% or more identity with any of SEQ ID NOs: 1 to 14. In some embodiments, aptamers comprise, consist essentially of, or consist of a nucleic acid sequence comprising at least about 25, 30, 35, or more consecutive nucleotides of a sequence having at least 85% or more identity with SEQ ID NO: 23. In some embodiments, aptamers comprise, consist essentially of, or consist of a nucleic acid sequence comprising at least about 25, 30, or more consecutive nucleotides of a sequence having at least 85% or more identity with SEQ ID NO: 24. In some embodiments, aptamers comprise, consist essentially of, or consist of a nucleic acid sequence comprising at least about 25, 30, 35, 40, or more consecutive nucleotides of a sequence having at least 85% or more identity with SEQ ID NO: 25. In some embodiments, aptamers comprise, consist essentially of, or consist of a nucleic acid sequence comprising at least about 25, 30, 35, or more consecutive nucleotides of a sequence having at least 85% or more identity with SEQ ID NO: 26.

In some embodiments, aptamers comprise, consist essentially of, or consist of a nucleic acid sequence comprising at least about 30, 35, 40, 45, 50, 55, 60, 65, 70, 75, 80 or more consecutive nucleotides of a sequence having at least 90% or more identity with any of SEQ ID NOs: 1 to 14. In some embodiments, aptamers comprise, consist essentially of, or consist of a nucleic acid sequence comprising at least about 25, 30, 35, or more consecutive nucleotides of a sequence having at least 90% or more identity with SEQ ID NO: 23. In some embodiments, aptamers comprise, consist essentially of, or consist of a nucleic acid sequence comprising at least about 25, 30, or more consecutive nucleotides of a sequence having at least 90% or more identity with SEQ ID NO: 24. In some embodiments, aptamers comprise, consist essentially of, or consist of a nucleic acid sequence comprising at least about 25, 30, 35, 40, or more consecutive nucleotides of a sequence having at least 90% or more identity with SEQ ID NO: 25. In some embodiments, aptamers comprise, consist essentially of, or consist of a nucleic acid sequence comprising at least about 25, 30, 35, or more consecutive nucleotides of a sequence having at least 90% or more identity with SEQ ID NO: 26.

In some embodiments, aptamers comprise, consist essentially of, or consist of a nucleic acid sequence comprising at least about 30, 35, 40, 45, 50, 55, 60, 65, 70, 75, 80 or more consecutive nucleotides of a sequence having at least 95% or more identity with any of SEQ ID NOs: 1 to 14. In some embodiments, aptamers comprise, consist essentially of, or consist of a nucleic acid sequence comprising at least about 25, 30, 35, or more consecutive nucleotides of a sequence having at least 95% or more identity with SEQ ID NO: 23. In some embodiments, aptamers comprise, consist essentially of, or consist of a nucleic acid sequence comprising at least about 25, 30, or more consecutive nucleotides of a sequence having at least 95% or more identity with SEQ ID NO: 24. In some embodiments, aptamers comprise, consist essentially of, or consist of a nucleic acid sequence comprising at least about 25, 30, 35, 40, or more consecutive nucleotides of a sequence having at least 95% or more identity with SEQ ID NO: 25. In some embodiments, aptamers comprise, consist essentially of, or consist of a nucleic acid sequence comprising at least about 25, 30, 35, or more consecutive nucleotides of a sequence having at least 95% or more identity with SEQ ID NO: 26.

In some embodiments, aptamers comprise, consist essentially of, or consist of a nucleic acid sequence comprising at least about 30, 35, 40, 45, 50, 55, 60, 65, 70, 75, 80 or more consecutive nucleotides of a sequence having at least 96% or more identity with any of SEQ ID NOs: 1 to 14. In some embodiments, aptamers comprise, consist essentially of, or consist of a nucleic acid sequence comprising at least about 25, 30, 35, or more consecutive nucleotides of a sequence having at least 96% or more identity with SEQ ID NO: 23. In some embodiments, aptamers comprise, consist essentially of, or consist of a nucleic acid sequence comprising at least about 25, 30, or more consecutive nucleotides of a sequence having at least 96% or more identity with SEQ ID NO: 24. In some embodiments, aptamers comprise, consist essentially of, or consist of a nucleic acid sequence comprising at least about 25, 30, 35, 40, or more consecutive nucleotides of a sequence having at least 96% or more identity with SEQ ID NO: 25. In some embodiments, aptamers comprise, consist essentially of, or consist of a nucleic acid sequence comprising at least about 25, 30, 35, or more consecutive nucleotides of a sequence having at least 96% or more identity with SEQ ID NO: 26.

In some embodiments, aptamers comprise, consist essentially of, or consist of a nucleic acid sequence comprising at least about 30, 35, 40, 45, 50, 55, 60, 65, 70, 75, 80, 85 or more consecutive nucleotides of a sequence having at least 97% or more identity with any of SEQ ID NOs: 1 to 14. In some embodiments, aptamers comprise, consist essentially of, or consist of a nucleic acid sequence comprising at least about 25, 30, 35, or more consecutive nucleotides of a sequence having at least 97% or more identity with SEQ ID NO: 23. In some embodiments, aptamers comprise, consist essentially of, or consist of a nucleic acid sequence comprising at least about 25, 30, or more consecutive nucleotides of a sequence having at least 97% or more identity with SEQ ID NO: 24. In some embodiments, aptamers comprise, consist essentially of, or consist of a nucleic acid sequence comprising at least about 25, 30, 35, 40, or more consecutive nucleotides of a sequence having at least 97% or more identity with SEQ ID NO: 25. In some embodiments, aptamers comprise, consist essentially of, or consist of a nucleic acid sequence comprising at least about 25, 30, 35, or more consecutive nucleotides of a sequence having at least 97% or more identity with SEQ ID NO: 26.

In some embodiments, aptamers comprise, consist essentially of, or consist of a nucleic acid sequence comprising at least about 30, 35, 40, 45, 50, 55, 60, 65, 70, 75, 80 or more consecutive nucleotides of a sequence having at least 98% or more identity with any of SEQ ID NOs: 1 to 14. In some embodiments, aptamers comprise, consist essentially of, or consist of a nucleic acid sequence comprising at least about 25, 30, 35, or more consecutive nucleotides of a sequence having at least 98% or more identity with SEQ ID NO: 23. In some embodiments, aptamers comprise, consist essentially of, or consist of a nucleic acid sequence comprising at least about 25, 30, or more consecutive nucleotides of a sequence having at least 98% or more identity with SEQ ID NO: 24. In some embodiments, aptamers comprise, consist essentially of, or consist of a nucleic acid sequence comprising at least about 25, 30, 35, 40, or more consecutive nucleotides of a sequence having at least 98% or more identity with SEQ ID NO: 25. In some embodiments, aptamers comprise, consist essentially of, or consist of a nucleic acid sequence comprising at least about 25, 30, 35, or more consecutive nucleotides of a sequence having at least 98% or more identity with SEQ ID NO: 26.

In some embodiments, aptamers comprise, consist essentially of, or consist of a nucleic acid sequence comprising at least about 30, 35, 40, 45, 50, 55, 60, 65, 70, 75, 80 or more consecutive nucleotides of a sequence having at least 99% or more identity with any of SEQ ID NOs: 1 to 14. In some embodiments, aptamers comprise, consist essentially of, or consist of a nucleic acid sequence comprising at least about 25, 30, 35, or more consecutive nucleotides of a sequence having at least 99% or more identity with SEQ ID NO: 23.

In some embodiments, aptamers comprise, consist essentially of, or consist of a nucleic acid sequence comprising at least about 25, 30, or more consecutive nucleotides of a sequence having at least 99% or more identity with SEQ ID NO: 24. In some embodiments, aptamers comprise, consist essentially of, or consist of a nucleic acid sequence comprising at least about 25, 30, 35, 40, or more consecutive nucleotides of a sequence having at least 99% or more identity with SEQ ID NO: 25. In some embodiments, aptamers comprise, consist essentially of, or consist of a nucleic acid sequence comprising at least about 25, 30, 35, or more consecutive nucleotides of a sequence having at least 99% or more identity with SEQ ID NO: 26.

In some embodiments, aptamers comprise, consist essentially of, or consist of a nucleic acid sequence comprising at least about 30, 35, 40, 45, 50, 55, 60, 65, 70, 75, 80 or more consecutive nucleotides of a sequence comprising any one of SEQ ID NOs: 1 to 14.

In some embodiments, aptamers comprise, consist essentially of, or consist of a nucleic acid sequence comprising at least about 30 or more consecutive nucleotides of a sequence comprising SEQ ID NO: 23. In some embodiments, aptamers comprise, consist essentially of, or consist of a nucleic acid sequence comprising at least about 30 or more consecutive nucleotides of a sequence comprising SEQ ID NO: 24. In some embodiments, aptamers comprise, consist essentially of, or consist of a nucleic acid sequence comprising at least about 30 or more consecutive nucleotides of a sequence comprising SEQ ID NO: 25. In some embodiments, aptamers comprise, consist essentially of, or consist of a nucleic acid sequence comprising at least about 30 or more consecutive nucleotides of a sequence comprising SEQ ID NO: 26.

The aptamers may comprise natural or non-natural nucleotides and/or base derivatives (or combinations thereof). In some embodiments, the aptamers comprise one or more modifications such that they comprise a chemical structure other than deoxyribose, ribose, phosphate, adenine (A), guanine (G), cytosine (C), thymine (T), or uracil (U). The aptamers may be modified at the nucleobase, at the sugar or at the phosphate backbone.

In some embodiments, the aptamers comprise one or more modified nucleotides. Exemplary modifications include for example nucleotides comprising an alkylation, arylation or acetylation, alkoxylation, halogenation, amino group, or another functional group. Examples of modified nucleotides include, but are not limited to, 2'-fluoro ribonucleotides, 2'-NH$_2$—, 2'-OCH$_3$— and 2'-O-methoxyethyl ribonucleotides, which are used for RNA aptamers.

The aptamers may be wholly or partly phosphorothioate or DNA, phosphorodithioate or DNA, phosphoroselenoate or DNA, phosphorodiselenoate or DNA, locked nucleic acid (LNA), peptide nucleic acid (PNA), N3'-P5 'phosphoramidate RNA/DNA, cyclohexene nucleic acid (CeNA), tricyclo DNA (tcDNA) or spiegelmer, or the phosphoramidate morpholine (PMO) components or any other modification known to those skilled in the art (see also Chan et al., Clinical and Experimental Pharmacology and Physiology (2006) 33, 533-540).

Some of the modifications may allow the aptamers to be stabilized against nucleic acid-cleaving enzymes. In the stabilization of the aptamers, a distinction can generally be made between the subsequent modification of the aptamers and the selection with already modified RNA/DNA. The stabilization may not affect the affinity of the modified RNA/DNA aptamers but may prevent the rapid decomposition of the aptamers in an organism, biological solutions, or solutions, by RNases/DNases. An aptamer is referred to as stabilized if the half-life of the aptamer in the sample (e.g. biological medium, organism, solution) is greater than one minute, greater than one hour, or greater than one day. The aptamers may be modified with reporter molecules, which may enable detection of the labelled aptamers. Reporter molecules may also contribute to increased stability of the aptamers.

Aptamers form a three-dimensional structure that depends on their nucleic acid sequence. The three-dimensional structure of an aptamer may arise due to Watson and Crick intramolecular base pairing, Hoogsteen base pairing (quadruplex), wobble-pair formation, or other non-canonical base interactions. In some embodiments, the three-dimensional structure enables aptamers, analogous to antigen-antibody binding, to bind target structures accurately. A nucleic acid sequence of an aptamer may, under defined conditions, have a three-dimensional structure that is specific to a defined target structure.

Embodiments comprise competitive aptamers that compete for binding to a target protein as defined herein with aptamers as described herein. Embodiments comprise competitive aptamers that compete for binding to a target protein as defined herein with the aptamers set forth in any one of SEQ ID NOs: 1 to 14 or SEQ ID NOs: 23-26, or with aptamers having a nucleic acid sequence having at least 85%, at least 90%, at least 95%, at least 96%, at least 97%, at least 98%, at least 99% sequence identity to the nucleotide sequence of any one of SEQ ID NOs: 1 to 14 or SEQ ID NOs: 23-26. Embodiments comprise competitive one or more aptamers that compete for binding to a target protein as defined herein with one or more of the aptamers described above. In some embodiments, competition assays may be used identify a competitive aptamer that competes for binding to a target protein as defined herein. In an exemplary, non-limiting, competition assay, an immobilized target protein as defined herein is incubated in a solution comprising a first labelled aptamer that binds to a target protein as defined herein and a second unlabelled aptamer that is being tested for its ability to compete with the first aptamer for binding to a target protein as defined herein. As a control, an immobilized target protein as defined herein may be incubated in a solution comprising the first labelled aptamer but not the second unlabelled aptamer. After incubation under conditions permissive for binding of the first aptamer to a target protein as defined herein excess unbound aptamer may be removed, and the amount of label associated with immobilized target protein as defined herein measured. If the amount of label associated with immobilized target as defined herein is substantially reduced in the test sample relative to the control sample, then that indicates that the second aptamer is competing with the first aptamer for binding to a target protein as defined herein.

Support

In some embodiments, the target peptide or protein is attached to a support. In a non-limiting example, the support may be a solid support. Non-limiting examples of a solid support include a membrane or a bead. In some embodiments, the support may be a two-dimensional support. A non-limiting example of a two-dimensional support is a microplate. In some embodiments, the support may be a three-dimensional support. A non-limiting example of a three-dimensional support is a bead. In some embodiments, the support may comprise at least one magnetic bead.

In some embodiments, the protein comprises a polyhistidine tag (His tag) tag (e.g. hexa-histidine tag) at its N- or C-termini. For example, the protein can be a recombinant protein having Histidine residues at its C-terminus or its N-terminus. In some embodiments, the His-tagged protein can be immobilized onto a support carrying a histidine binding agent. For example, the His-tagged protein can be immobilized to a support having nickel nitrilotriacetic acid (Ni-NTA).

In some embodiments, the support may comprise at least one nanoparticle. A non-limiting example of a nanoparticle is a gold nanoparticle or the like. In yet further embodiments, the support may comprise a microtiter or other assay plate, a strip, a membrane, a film, a gel, a chip, a microparticle, a nanofiber, a nanotube, a micelle, a micropore, a nanopore, or a biosensor surface. In some embodiments, the biosensor surface may be a probe tip surface, a biosensor flow-channel, or similar.

In some embodiments, the support comprises a membrane. Non-limiting examples of a membrane include a nitrocellulose, a polyethylene (PE), a polytetrafluoroethylene (PTFE), a polypropylene (PP), a cellulose acetate (CA), a polyacrylonitrile (PAN), a polyimide (PI), a polysulfone (PS), a polyethersulfone (PES) membrane or an inorganic membrane comprising aluminum oxide ($Al_2O_3$), silicon oxide ($SiO_2$), and/or zirconium oxide ($ZrO_2$). Non-limiting examples of materials from which a support may be made include inorganic polymers, organic polymers, glasses, organic and inorganic crystals, minerals, oxides, ceramics, metals, especially precious metals, carbon, and semiconductors. In an embodiment, the organic polymer is a polymer based on polystyrene. Biopolymers, including but not limited to cellulose, dextran, agar, agarose and Sephadex, which may be functionalized in particular as nitrocellulose or cyanogen bromide Sephadex, may be polymers in a support.

Detectable Labels

In some embodiments, the aptamers of the invention are used to detect and/or quantify the amount of a target as defined herein in a sample. Typically, the aptamers comprise a detectable label. Any label capable of facilitating detection and/or quantification of the aptamers may be used herein. Non-limiting examples of detectable labels are described below.

In some embodiments, the detectable label is a fluorescent moiety, e.g. a fluorescent compound. In some embodiments, the aptamer comprises a fluorescent and a quencher compound. Fluorescent and quencher compounds are known in the art. See, for example, Mary Katherine Johansson, Methods in Molecular Biol. 335: Fluorescent Energy Transfer Nucleic Acid Probes: Designs and Protocols, 2006, Didenko, ed., Humana Press, Totowa, NJ, and Marras et al., 2002, Nucl. Acids Res. 30, e122 (incorporated by reference herein).

In some embodiments, the detectable label is FAM. In some embodiments, the FAM-label is conjugated to the 5' end or the 3' end of the aptamer. One of ordinary skill in the art would understand that the label may be located at any suitable position within the aptamer.

In some embodiments, the aptamer comprises a FAM fluorophore at its 5' end. In some embodiments, the aptamer is synthesized by incorporating phosphoramidite one at a time into the nucleic acid chain and the FAM-labeled phosphoramidite is incorporated through the synthesis process. In some embodiments, the FAM fluorophore is attached at the 5' end of the aptamer via a linker. In some embodiments, the detectable label is attached to an aptamer described herein via a moiety selected from a thiol group, an amine group, an azide, six-carbon linker, and an aminoallyl group and combinations thereof. In some embodiments, the FAM label can be incorporated into the aptamer using a forward primer with a FAM on the 5' end. In some embodiments, the aptamer can be prepared by solid phase synthesis with the FAM label already in place, attached to the 5' end as in the primer.

Moieties that result in an increase in detectable signal when in proximity of each other may also be used herein, for example, as a result of fluorescence resonance energy transfer ("FRET"); suitable pairs include but are not limited to fluorescein and tetramethylrhodamine; rhodamine 6G and malachite green, and FITC and thiosemicarbazole, to name a few.

In some embodiments, the detectable label is and/or comprises a moiety selected from at least one of the following non-limiting examples: a fluorophore, a nanoparticle, a quantum dot, an enzyme, a radioactive isotope, a pre-defined sequence portion, a biotin, a desthiobiotin, a thiol group, an amine group, an azide, an aminoallyl group, a digoxigenin, an antibody, a catalyst, a colloidal metallic particle, a colloidal non-metallic particle, an organic polymer, a latex particle, a nanofiber, a nanotube, a dendrimer, a protein, and a liposome.

In some embodiments, the detectable label is a fluorescent protein such as Green Fluorescent Protein (GFP) or any other fluorescent protein known to those skilled in the art.

In some embodiments, the detectable label is an enzyme. For example, the enzyme may be selected from horseradish peroxidase, alkaline phosphatase, urease, β-galactosidase or any other enzyme known to those skilled in the art.

In some embodiments, the nature of the detection will be dependent on the detectable label used. For example, the label may be detectable by virtue of its colour e.g. gold nanoparticles. A colour can be detected quantitatively by an optical reader or camera e.g. a camera with imaging software.

In some embodiments, the detectable label is a fluorescent label e.g. a quantum dot. In such embodiments, the detection means may comprise a fluorescent plate reader, strip reader or similar, which is configured to record fluorescence intensity.

In some embodiments in which the detectable label is an enzyme label, non-limiting detection means may, for example, be colorimetric, chemiluminescence and/or electrochemical (including, but not limited to using an electrochemical detector). Electrochemical sensing may be through conjugation of a redox reporter (including, but not limited to methylene blue or ferrocene) to one end of the aptamer and a sensor surface to the other end. A change in aptamer conformation upon target binding may change the distance between the reporter and sensor to provide a readout.

In some embodiments, the detectable label may further comprise enzymes, including but not limited to, horseradish peroxidase (HRP), Alkaline phosphatase (APP) or similar, to catalytically turnover a substrate to give an amplified signal.

Embodiments comprise a complex (e.g. conjugate) comprising aptamers of the invention and a detectable molecule. Typically, the aptamers of the invention are covalently or physically conjugated to a detectable molecule.

In some embodiments, the detectable molecule is a visual, optical, photonic, electronic, acoustic, opto-acoustic, mass, electrochemical, electro-optical, spectrometric, enzymatic, or otherwise physically, chemically or biochemically detectable label.

In some embodiments, the detectable molecule is detected by luminescence, UV/VIS spectroscopy, enzymatically, electrochemically or radioactively. Luminescence refers to the emission of light. For example, photoluminescence, chemiluminescence and bioluminescence are used for detection of the label. In photoluminescence or fluorescence, excitation occurs by absorption of photons. Exemplary fluorophores include, but are not limited to, bisbenzimidazole, fluorescein, acridine orange, Cy5, Cy3 or propidium iodide, which can be covalently coupled to aptamers, tetramethyl-6-carboxyhodamine (TAMRA), Texas Red (TR), rhodamine, Alexa Fluor dyes (et al. Fluorescent dyes of different wavelengths from different companies).

In some embodiments, the detectable molecule is a colloidal metallic particle, including but not limited to a gold nanoparticle, colloidal non-metallic particle, quantum dot, organic polymer, latex particle, nanofiber (carbon nanofiber, as a non-limiting example), nanotube (carbon nanotube, as a non-limiting example), dendrimer, protein or liposome with signal-generating substances. Colloidal particles may be detected colorimetrically.

In some embodiments, the detectable molecule is an enzyme. In some embodiments, the enzyme may convert substrates to coloured products. Examples of the enzyme include but are not limited toperoxidase, luciferase, β-galactosidase or alkaline phosphatase. For example, the colourless substrate X-gal is converted by the activity of β-galactosidase to a blue product whose colour is visually detected.

In some embodiments, the detection molecule is a radioactive isotope. The detection may also be carried out by means of radioactive isotopes with which the aptamer is labelled, including but not limited to $^{3}H$, $^{14}C$, $^{32}P$, $^{33}P$, $^{35}S$ or $^{125}I$. In an embodiment, scintillation counting may be conducted, and thereby the radioactive radiation emitted by the radioactively labelled aptamer target complex is measured indirectly. A scintillator substance is excited by the isotope's radioactive emissions. During the transition of the scintillation material, back to the ground state, the excitation energy is released again as flashes of light, which are amplified and counted by a photomultiplier.

In some embodiments, the detectable molecule is selected from digoxigenin and biotin. Thus, the aptamers may also be labelled with digoxigenin or biotin, which are bound for example by antibodies or streptavidin, which may in turn carry a label, such as an enzyme conjugate. The prior covalent linkage (conjugation) of an aptamer with an enzyme can be accomplished in several known ways. Detection of aptamer binding may also be achieved through labelling of the aptamer with a radioisotope in an RIA (radioactive immunoassay), preferably with $^{125}I$, or by fluorescence in a FIA (fluoroimmunoassay) with fluorophores, preferably with fluorescein or fluorescein isothiocyanate (FITC).

Embodiments comprise methods for detecting the presence, absence or amount of a target as defined herein in a sample. In the methods, the sample may be interacted (i.e. contacted) with an aptamer as described herein. For example, the sample and aptamers as described herein may be incubated under conditions sufficient for at least a portion of the aptamer to bind to a target as defined herein in the sample.

A person skilled in the art will understand that the conditions required for binding to occur between the aptamers described herein and a target as defined herein. In some embodiments, the sample and aptamer may be incubated at temperatures between about 4° C. and about 40° C. In some embodiments, the sample and aptamer may be incubated at temperatures between about 20° C. and about 37° C. In some embodiments, the sample and aptamer may be incubated at or about 22° C. The incubation temperature may be selected from the range of 4° C. to less than 20° C., 20° C. to less than 22° C., 22° C. to less than 24° C., 24° C. to less than 26° C., 26° C. to less than 28° C., 28° C. to less than 30° C., 30° C. to less than 32° C., 32° C. to less than 34° C., 34° C. to less than 36° C., 36° C. to 37° C., and 37° C. to 40° C. In some embodiments, the sample and aptamer may be diluted to different concentrations (e.g. at least about 1%, 5%, 10%, 20%, 25%, 30%, 40%, 50%, 60%, 70% 80% v/v or more) with a buffer (exemplary buffers include but are not limited to PBS). The diluted concentrations may be selected from the range of 1% to less than 5%, 5% to less than 10%, 10% to less than 20%, 20% to less than 30%, 30% to less than 40%, 40% to less than 50%, 50% to less than 60%, 60% to less than 70%, 70% to less than 80%, or 80% to less than 90%. In some embodiments, the aptamer concentration before dilution may be from 100 nM to 50 μM. In some embodiments, the aptamer concentration before dilution may be selected from the range of 100 nM to 500 nM, 500 nM to 1 μM, 1 μM to 2 μM, 2 μM to 5 μM, 5 μM to 10 μM, 10 μM to 15 μM, 15 μM to 20 μM, 20 μM to 30 μM, 30 μM to 40 μM, 40 μM to 50 μM, 50 μM to 60 μM, 60 μM to 70 μM, 70 μM to 80 μM, 80 μM to 90 μM, 90 μM to 100 μM. In some embodiments, the aptamer concentration before dilution may be a concentration selected from the ranges described herein in. The selected value may be selected from 0.1 μM increment concentrations in a range herein. In some embodiments, the aptamer concentration before dilution may be 2 μM. In some embodiments, the sample and aptamer may be incubated whilst shaking and/or mixing. In some embodiments, the sample and aptamer are incubated for at least 1 minute, at least 5 minutes, at least 15 minutes, at least 1 hour, or more. The sample and aptamer may be incubated for 1 minute to less than 5 minutes, 5 minutes to less than 15 minutes, 15 minutes to less than one hour, one hour to less than 24 hours, 24 hours to less than 48 hours.

In some embodiments, binding of the aptamer and a target as defined leads to formation of an aptamer-target complex. The binding or binding event may be detected, for example, visually, optically, photonically, electronically, acoustically, opto-acoustically, by mass, electrochemically, electro-optically, spectrometrically, enzymatically or otherwise chemically, biochemically or physically as described herein.

The binding of aptamer and the target may be detected using any suitable technique. As discussed above, for example, binding of the aptamer and the target may be detected using a biosensor. In some embodiments, binding of the aptamer and the target is detected using the non-limiting examples of SPR, RIfS, BLI, LFD or ELONA as described herein.

In some embodiments, the aptamer can be attached to the surface of the biosensor using a biotin group. In some embodiments, the biotin group is attached at the 5' end or the 3' end of the aptamer. In some embodiments, the surface of the biosensor has an avidin/streptavidin attached thereto and the immobilization of the aptamer to the surface of the biosensor is via biotin-avidin interaction. In some embodiments, the surface of the biosensor is coated with avidin/streptavithn.

Kits

Embodiments also provide a kit for detecting and/or quantifying *C. difficile*, wherein the kit comprises one or more aptamers as described herein. Typically, the kit also comprises a detectable molecule as described herein.

Embodiments provide a kit that further comprises a light source as described herein. In an embodiment, the kit may further comprise a bandpass filter as described herein. In an embodiment, the kit may comprise viewing goggles or glasses or the like as described herein. In some embodiments, the kit comprises:
a) A solution comprising aptamers having a detection molecule conjugated thereto e.g. a fluorophore capable of emitting at a wavelength of between about 485-515 nm. In some embodiments, the fluorophore is capable of emitting at a wavelength of between about 490-505 nm. In an embodiment the fluorophore is capable of emitting at a wavelength of about 505 nm;
b) A light source. In some embodiments, the light source produces light having a wavelength of between about 485-515 nm. In an embodiment, the light source produces light having a wavelength of between about 490-505 nm;
c) A bandpass filter. In an embodiment, the bandpass filter is a 590 nm bandpass filter; and
d) Viewing goggles. In an embodiment, the viewing goggles are orange viewing goggles.

In some embodiments, the kit further comprises instructions for use in accordance with any of the methods described herein.

The kit may comprise further components for the reaction intended by the kit or the method to be carried out, for example components for an intended detection of enrichment, separation and/or isolation procedures. Non-limiting examples include buffer solutions, substrates for a colour reaction, dyes or enzymatic substrates. In the kit, the aptamer may be provided in a variety of forms, including but not limited to being pre-immobilized onto a support (e.g. solid support), freeze-dried, or in a liquid medium.

A kit herein may be used for carrying out any method described herein. It will be appreciated that the parts of the kit may be packaged individually in vials or in combination in containers or multi-container units. Typically, manufacture of the kit follows standard procedures which are known to the person skilled in the art.

Uses

In some embodiments, method of detecting *C. difficile*, e.g. *C. difficile* spores, using the aptamers described herein, is provided. The method may comprise interacting the sample with an aptamer described herein and detecting the presence, absence, and/or amount of *Clostridium difficile*. The method may be for detecting the presence, absence, and/or amount of *Clostridium difficile* spores in a sample using a detection method including, but not limited to, photonic detection, electronic detection, acoustic detection, electrochemical detection, electro-optic detection, enzymatic detection, chemical detection, biochemical detection, or physical detection.

In some embodiments, the method is for detecting the presence, absence, or amount of *C. difficile*, e.g. *C. difficile* spores, on a surface. In some embodiments, the aptamers and method provided may have utility in detecting *C. difficile* on surfaces in hospital and healthcare facilities. Non-limiting examples of surfaces may include bed linen, medical equipment, clothing, floors, walls, and the like. In a non-limiting example, the aptamers of the present invention may be used to detect the presence, absence, and/or amount of *C. difficile*, e.g. *C. difficile* spores, on a patient's body.

In some embodiments, the aptamers may be for use in detecting *C. difficile*, e.g. *C. difficile* spores, in a sample previously obtained from a surface as described herein.

In some embodiments, the aptamers of the invention may be used to detect whole *C. difficile* spores. In some embodiments, the aptamers may be used to detect *C. difficile* proteins as described herein.

In some embodiments, the aptamers may be used to detect *C. difficile* spores or proteins in real-time. Following detection and/or quantification of *C. difficile*, action may be taken to kill and/or remove the spores. Non-limiting examples of such action may include washing or destruction of bed linen, and/or cleaning of surfaces including but not limited to medical equipment, beds, walls, floors, and the like. Measures such as isolation of patients and enforcement of stringent hygiene protocols may also be taken.

In some embodiments, the aptamers of the invention are for use in a method of detecting the presence or absence of *C. difficile* spores using a light source. In certain embodiments, there is provided a method of detecting the presence or absence of *C. difficile* spores comprising:
a) Providing an aptamer conjugate comprising an aptamer described herein, wherein the aptamer is conjugated to a detectable moiety. In an embodiment, the detectable moiety is a fluorescent moiety;
b) Contacting the aptamer conjugate with a location of interest, wherein the location of interest may comprise *C. difficile* spores;
c) Incubating the aptamer conjugate at the location of interest for a predetermined period of time to allow the aptamer conjugate to bind to a *C. difficile* spore if present;
d) Optionally washing the location of interest to remove any unbound aptamer conjugates; and
e) Visualizing the aptamer conjugate bound to a *C. difficile* spore.

In some embodiments, the location comprises a surface. In some embodiments, the location comprises a human, e.g. a patient's body, or a sample obtained from a subject suspected of having or diagnosed with a *Clostridium difficile* infection. In some embodiments, the location comprises an object located in a hospital environment In some embodiments, visualizing the aptamer conjugate comprises illuminating the location with a light source. In some embodiments, the light source produces light at a predetermined wavelength, wherein the predetermined wavelength corresponds to a wavelength of light emitted by the detectable moiety of the aptamer conjugate.

In some embodiments, the step of visualizing the location may be performed in ambient light or in dark conditions.

In some embodiments, the method further comprises filtering the light produced by the light source.

In some embodiments, the method further comprises imaging (e.g. photographing) the location and detecting the presence or absence of *C. difficile* spores.

In some embodiments, the method of detecting *C. difficile* may comprise applying one or more of the aptamers of the invention to a location suspected of comprising *C. difficile* spores. Following a predetermined period of time sufficient to permit the aptamer binding to *C. difficile* spores, the location may be washed one or more times to remove any unbound aptamer. The method may then comprise a set of conditions for illuminating the location using a light source. In an embodiment, the light source may be in the form of a forensic light source. In an embodiment, the light source may be in the form of a Polilight® Flare.

In some embodiments, the light source may be capable of switching between different wavelengths, each wavelength being suited to a specific interchangeable filter. The forensic light source may be in the form of a LED, laser, Polilight® or the like. In some embodiments, the light source is a handheld light source. In an embodiment, the handheld light source may be a Polilight Flare+2, which is a battery operated, handheld LED light source, available from e.g. Rofin Forensic.

Aptly, each Polilight Flare "torch" may produce light within a specified wavelength range. For example, in some embodiments, the light source may produce light at a wavelength of between about 360 nm-385 nm (UV light). In some embodiments, the light source may produce light at a wavelength of between about 405 nm-420 nm. In some embodiments, the light source may produce light at a wavelength of between about 435 nm-4.65 nm. In some embodiments, the light source may produce light at a wavelength of between about 485 nm-515 nm. In some embodiments, the light source may produce light at a wavelength of between about 490 nm-505 nm. In some embodiments, the light source may produce light at a wavelength of between about 510 nm-545 nm. In some embodiments, the light, source may produce light at a wavelength of between about 530 nm-560 nm. In some embodiments, the light source may produce light at a wavelength of between about 585 nm-605 nm. In some embodiments, the light source may produce light at a wavelength of between about 615 nm-635 nm. In some embodiments, the light source may produce light at a wavelength of between about 400 nm-700 nm. In some embodiments, the light source may produce light at a wavelength of between about 835 nm-865 nm. In some embodiments, the light source may produce light at a wavelength of between about 935 nm-965 nm.

In some embodiments, the light source used may be compatible with a detectable molecule conjugated to the aptamer. In some embodiments, the aptamer is conjugated to a detection molecule. In some embodiments, the detection molecule may be a fluorophore which emits in a spectral range which corresponds to the output of the light source. In some embodiments, the aptamer may be conjugated to a fluorophore which emits at a wavelength of about 505 nm. In some embodiments, the light source produces light having a wavelength of about 505 nm.

In some embodiments, the method may comprise the use of a bandpass filter in combination with the light source. The bandpass filter may be configured to transmit light of a certain wavelength band and reject stray light outside the predetermined wavelength band. In some embodiments, the light source is configured to produce narrow bands of light having centre wavelengths of 365 nm, 415 nm, 450 nm, 505 nm, 530 nm, 545 nm, 620 nm, and 850 nm. In some embodiments, the light source is configured to produce narrow bands of light having a center wavelength of 505 nm, in addition to white light wavelengths. In some embodiments, the bandpass filter is a 590 nm bandpass filter.

In some embodiments, the method may further comprise visualizing the location with viewing goggles, glasses, or the like. In some embodiments, the viewing goggles are of a colour which corresponds to the colour of light produced by the light source and emitted by the detection molecule conjugated to the aptamer. In some embodiments, the goggles are orange and thus are suitable for use in combination with a light source which produces light having a wavelength of between about 485 nm-515 nm, e.g. 505 nm, and an aptamer which comprises a detection molecule that emits at a wavelength of approximately 505 nm.

In an aspect, the invention relates to the development of aptamers which bind to *Clostridium difficile* and methods of using the same. In an aspect, the invention relates to aptamers which specifically bind to a *C. difficile* spore. The aptamers may specifically bind to a *C. difficile* protein; e.g. a surface protein. The molecule that an aptamer binds to may be referred to as a target molecule. Further details of the target molecules are provided herein.

Unexpectedly, the present inventors have identified aptamers which are capable of identifying *C. difficile* spores.

In embodiments, the invention provides an aptamer capable of specifically binding to a *Clostridium difficile* protein.

In embodiments, the *Clostridium difficile* protein is a surface protein of *Clostridium difficile* spore. In embodiments, the *Clostridium difficile* protein is a spore coat surface protein or an exosporium layer protein.

In embodiments the *Clostridium difficile* protein selected from CdeC, CdeM, CotA, CotE and CotE Chitinase.

In embodiments the *Clostridium difficile* protein is a CdeC protein having an amino acid sequence as set forth in SEQ ID NO 18.

In embodiments the *Clostridium difficile* protein is a CdeM protein having an amino acid sequence as set forth in SEQ ID NO: 19.

In embodiments the *Clostridium difficile* protein is a CotA, protein having an amino acid sequence as set forth in SEQ ID NO: 15.

In embodiments the *Clostridium difficile* protein is a CotE, protein having an amino acid sequence as set forth in SEQ ID NO: 16.

In embodiments the *Clostridium difficile* protein is a CotE Chitinase protein having an amino acid sequence as set forth in SEQ ID NO: 17.

In embodiments the aptamer comprises or consists of:
a) a nucleic acid sequence selected from any one of the nucleic acid sequences as set forth in any of SEQ ID NOs: 1 to 14;
b) a nucleic acid sequence having at least 85%, for example 90%, 95%, 96%, 97%, 98%, or 99% identity with any one of the nucleic acid sequence the nucleic acid sequences as set forth in any of SEQ ID NOs: 1 to 14;
c) a nucleic acid sequence having at least about 30 consecutive nucleotides of any one the nucleic acid sequences as set forth in any of SEQ ID NOs: 1 to 14;
d) a nucleic acid sequence having at least about 30 consecutive nucleotides of a sequence having at least 85% identity with any one of SEQ ID NOs: 1 to 14;
e) a nucleic acid sequence having a fragment extending from position 28 to position 64 of SEQ ID NO: 5, also known as SEQ ID NO: 23; or
f) a nucleic acid sequence having a fragment extending from position 28 to position 64 of SEQ ID NO: 5, also known as SEQ ID NO: 23 having at least 85% identity with SEQ ID NO: 23.

In embodiments the aptamer is a single stranded DNA aptamer.

In embodiments, there is provided an aptamer that competes for binding to a *Clostridium difficile* protein with the aptamer as described herein.

In embodiments the aptamer comprises a detectable label.

In embodiments the detectable label is and/or comprises a moiety selected from a fluorophore, a nanoparticle, a quantum dot, an enzyme, a radioactive isotope, a pre-defined sequence portion, a biotin, a desthiobiotin, a thiol group, an amine group, an azide, an aminoallyl group, a digoxigenin, an antibody, a catalyst, a colloidal metallic particle, a colloidal non-metallic particle, an organic polymer, a latex particle, a nanofiber, a nanotube, a dendrimer, a protein, and a liposome. In some embodiments, the detectable label is a fluorophore, a quantum dot, a colloidal metallic particle, or a colloidal non-metallic particle. In some embodiments, the detectable label is attached to an aptamer described herein via a moiety selected from a thiol group, an amine group, an azide and an aminoallyl group and combinations thereof.

In an aspect of the present invention, there is provided a complex comprising an aptamer of any preceding claim and a detectable molecule.

In an aspect of the present invention, there is provided a composition comprising at least one aptamer, wherein at least one of the aptamers is as described herein wherein the composition optionally comprises at least one of water, salts, one or more buffer herein, a detergent, and BSA.

In an aspect of the present invention, there is provided a composition comprising at least one aptamer having a nucleic acid sequence as set forth in SEQ ID NO: 1, 2, 3, 4 5, 6, 7, 8, 9, 10, 11, 12, 13, 14, or 23 wherein the composition optionally comprises at least one of water, salts, one or more buffer herein, a detergent, and BSA.

In an aspect of the present invention, there is provided a biosensor or test strip comprising an aptamer as described herein.

In an aspect of the present invention, there is provided an apparatus for detecting the presence, absence or level of *Clostridium difficile* in a sample, the apparatus comprising:
  i. a support; and
  ii. an aptamer as described herein.

In embodiments, the apparatus is for detecting the presence, absence or level of *Clostridium difficile* spores in a sample.

In embodiments, the sample is selected from:
  a) a sample previously obtained from a subject suspected of having or diagnosed with a *Clostridium difficile* infection; and
  b) an object located in a hospital environment, for example bedding, furniture, building structures.

In embodiments, the support is a bead, a microtiter or other assay plate, a strip, a membrane, a film, a gel, a chip, a microparticle, a nanoparticle, a nanofiber, a nanotube, a micelle, a micropore, a nanopore or a biosensor surface.

In embodiments, the apparatus is suitable for surface plasmon resonance (SPR), biolayer interferometry (BLI), lateral flow assay and/or enzyme-linked oligonucleotide assay (ELONA).

In an aspect of the present invention, there is provided a use of an aptamer a complex, a biosensor or test strip, a composition or apparatus as described herein for detecting, enriching, separating and/or isolating *Clostridium difficile*. In certain embodiments, the use is for specifically detecting, enriching, separating and/or isolating *Clostridium difficile* spores.

In an aspect of the present invention, there is provided a method of detecting the presence, absence or amount of *Clostridium difficile* in a sample, the method comprising:
  i. interacting the sample with an aptamer, a complex, or a composition as described herein; and
  ii. detecting the presence, absence or amount of *Clostridium difficile*.

In some embodiments, the method is for detecting the presence, absence or amount of *Clostridium difficile* spores in a sample.

In some embodiments, the presence, absence or amount of *Clostridium difficile* is detected by photonic detection, electronic detection, acoustic detection, electrochemical detection, electro-optic detection, enzymatic detection, chemical detection, biochemical detection or physical detection.

In an aspect of the present invention, there is provided a kit for detecting and/or quantifying *Clostridium difficile* the kit comprising an aptamer as described herein.

EXAMPLES

In the following, the invention will be explained in more detail by means of non-limiting examples of specific embodiments. In the example experiments, standard reagents and buffers free from contamination are used.

Example 1—Aptamer Selection

Target Information

Aptamers were selected against several protein targets of *C. difficile*. The targets were as follows:
  1. CdeC, a protein which has a molecular weight (MW) of 46,000 Da. Stored in a buffer with the following composition:
     20 mM HEPES-Na, pH 7.9, 5% glycerol, 200 mM NaCl, 0.2 mM $CaCl_2$, 0.1% Triton X114
     Concentration: 0.75 mg $ml^{-1}$
  2. CdeM a protein having a MW of 25,000 Da. Storage Buffer: 20 mM HEPES-Na, pH 7.9, 5% glycerol, 200 mM NaCl, 0.2 mM $CaCl_2$, 0.1% Triton X114
     Concentration: 0.50 mg $ml^{-1}$
  3. CdeM a protein with a MW of 25,000 Da. Storage Buffer: 20 mM HEPES-Na, pH 7.9, 5% glycerol, 200 mM NaCl, 0.2 mM $CaCl_2$, 0.1% Triton X114
     Concentration: 0.50 mg $ml^{-1}$
  4. CotA-His6 a protein with a MW of 34,900 Da Ext. Co: 27695 in water
     Storage Buffer: 20 mM HEPES, 5% glycerol, 200 mM NaCl, 1 mM DTT Concentration: 4.17 mg $ml^{-1}$
  5. rCotE, N281-F712, Molecular Weight: 48,000 Da, Storage Buffer: 20 mM HEPES-Na, pH 7.9, 5% glycerol, 200 mM NaCl, 0.2 mM $CaCl_2$, 0.1% Triton X114
     Concentration: ~0.8 mg $ml^{-1}$
  6. SPG-HU58. Non-pathogenic spores. Storage buffer: Sterile $dH_2O$
     Concentration: $1 \times 10^7$ CFU pure spores in 0.5 mL sterile water Preparation for Aptamer Selection The protein targets were each analyzed using a Nanodrop to generate a series of UV spectra, to confirm concentration and aggregation state of the targets (data not shown). Analysis of the UV spectra for the supplied CdeC, CdeM and CotE show clear signs of aggregation or multimerization. CotA and CotEC Chitinase show slight signs of aggregation. It is considered that some proteins may multimerize.

In addition, the targets were subjected to a 'Buffer Screen' with a panel of selection buffers. Binding of the aptamer library to beads immobilized with each target or blank beads were compared (data not shown). The buffer for each target which promoted greater interaction between the aptamer library and the target was identified and selected for future use in the selection process.

Non-limiting, exemplary buffers may be broadly similar for all of the targets. In some embodiments, the buffer may be a Tris buffer. In some embodiments, the pH may be approximately 7.4 to 7.6. In some embodiments, the ionic strength may be approximately 100 mM. Non-limiting examples of salts included in the buffer are $MgCl_2$ and $CaCl_2$. In some embodiments, the buffer may comprise detergents, including but not limited to Tween. In some embodiments, the buffer may comprise bovine serum albumin (BSA) or other stabilizers known in the art.

The buffers are as follows:
CdeC—50 mM Tris pH 7.6, 2.5 mM MgCl$_2$, 2.5 mM CaCl$_2$, 85 mM KoAc, 0.01% Tween 20, 0.01% BSA.
CdeM—50 mM Tris pH 7.6, 2.5 mM MgCl$_2$, 2.5 mM CaCl$_2$, 85 mM NaCl, 0.01% Tween 20, 0.01% BSA.
CotA—50 mM Tris pH 7.4, 5 mM MgCl$_2$, 1 mM CaCl$_2$, 77.5 mM NaCl, 4.5 mM KCl, 0.01% Tween 20, 0.01% BSA.
CotE—50 mM Tris pH 7.6, 2.5 mM MgCl$_2$, 2.5 mM CaCl$_2$, 28 mM K$_2$SO$_4$, 0.01% Tween 20, 0.01% BSA
rCotE Chitinase—50 mM Tris pH 7.4, 5 mM MgCl$_2$, 1 mM CaCl$_2$, 77.5 mM NaCl, 4.5 mM KCl, 0.01% Tween 20, 0.01% BSA.

Polyclonal Aptamer Selection

The selection protocol was broadly as followed:

His-tagged target protein were each loaded on to Ni-NTA coated magnetic beads and incubated for 1 hour in PBS. Loaded beads were washed and quantified, and used in aptamer selection.

The aptamer library was incubated with respective targets for one hour with constant mixing at room temperature in a selection buffer as identified in the buffer screen and shown above.

Target protein and bound aptamers were eluted using imidazole. Recovered material was subsequently purified to remove imidazole and amplified to create the enriched library for the subsequent selection round.

The process was repeated using increasing stringency from one selection round to the next.

The buffer conditions identified in the upfront screens were used for the first two rounds of in vitro selection. Subsequent rounds were conducted using a variety of different selection 'pressures'. The population from the best performing condition in each selection round was taken forward to the subsequent selection round. The amount of aptamer recovered during selection is quantified and is shown in FIGS. 6-10.

FIGS. 6-10 show the aptamer library recovery from the target-loaded beads (blue, on left side of each data set) gradually increases with sequential rounds of selection. Any fall in recovery generally coincides with the introduction of an increase in stringency during that round of selection. The best target: negative ratio (recovery from target-loaded beads vs. recovery from blank beads) was obtained in round 7 (R7) for targets CotA, CdeC, CdeM and CotEC Chitinase, and in R10 for target CotE, respectively. Each of these aptamer populations was then taken forward to a biophysical assay to confirm enrichment of target binding species.

Biophysical Characterization

Biolayer Interferometry (BLI) was used to assess the binding of each aptamer population to their respective targets. The target proteins were immobilized on separate Biolayer Interferometry sensor probes. The loaded probes were then incubated with the naïve aptamer library or the respective aptamer populations to monitor and compare the interactions.

BLI was performed at room temperature using the same buffer as those used during the selection. BLI probes were loaded with target protein in 1×PBS for 180 seconds. Subsequently the naïve aptamer library or respective aptamer populations were incubated for 300 seconds. The aptamers were then dissociated for 300 seconds in selection buffer.

The results are presented below in FIGS. 11-15.

FIGS. 11-15 show that the refined aptamer populations that have undergone the aptamer selection process described herein generally have improved binding to their respective targets compared to the unselected naïve library (some better than others). The immobilized targets show little to no interaction with unrefined naïve aptamer population. Binding is seen between the immobilized targets and the respective refined aptamer populations. Rapid association of the respective aptamer pool is seen for immobilized CotA, CotE and CotEC Chitinase (signals at ~480-780 sec). Both aptamer pools for CdeC and CdeM showed slower association to their respective targets. The bound aptamer populations do not appear to show significant dissociation from their targets (signals at 780-1080 sec).

Spore Selection

The refined aptamer populations described above were taken into 'spore-based selection' using *Clostridium difficile* spores as 'positive target.' *Bacillus subtilis* spores were used as a 'negative target' (counter selection) to reduce non-specific binding to spore surfaces. Four subsequent rounds of spore-based selection (rounds S1-S4) were performed. The amount of aptamer recovered during these selection rounds is quantified and shown in FIGS. 16-20.

After 4 consecutive rounds of spore-based selection (S1-S4); the five aptamer populations, selected against CotA, CdeC, CdeM, and CotE, all showed enhanced binding to the *Clostridium difficile* spores ('positive') compared to *Bacillus subtilis* spores ('negative'). This indicated further refinement of each of the aptamer populations in the context of the spore 'coat'.

Selectivity Profiling

The refined aptamer populations isolated against recombinant CotA, CdeC, CdeM, CotE and CotEC Chitinase, and subsequently further refined by spore-based selection; were fluorescently labelled and incubated with either *Clostridium difficile* spores or *Bacillus subtilis* spores. Unbound material was removed by washing, before imaging the spores by epifluorescence microscopy. The results are shown in FIGS. 21-25.

FIGS. 21-24 demonstrate that four of the isolated aptamer populations appear to bind preferentially to the *Clostridium difficile* spores compared to the *Bacillus subtilis* spores. These aptamer populations included CotA, CdeC, CdeM and CotE, respectively.

Conclusion

The reported data shows the following:

Biolayer Interferometry shows that the refined aptamer populations selected against CotA, CdeC, CdeM, CotE and CotEC Chitinase proteins, interact with their respective immobilized target. Interactions were a result of selection process (not simply through non-specific binding) as the 'Naïve' population did not show such interaction.

Epifluorescence microscopy showed that four of the aptamer populations have preferential binding to *Clostridium difficile* spores compared to *Bacillus subtilis* spores. These aptamer populations were isolated against CotA, CdeC, CdeM and CotE and subsequently refined by spore-based selection using *C. difficile* spores ('positive') and *B. subtilis* spores ('negative').

Aptamer populations isolated for CotEC Chitinase showed binding to both *Clostridium difficile* and *Bacillus subtilis* spores after 3 rounds of spore-based selection. No binding was seen for *C. difficile* after the 4th spore-based selection round.

Example 2—Monoclonal Aptamer Isolation

The refined pools (characterized in FIGS. 21-25) were taken forwards for monoclonal isolation. All aptamers were purified (after elution) and resuspended and stored in water. Before use in selections or binding assays, aptamers were diluted in a final concentration 1× buffer. Individual aptamer clones were isolated and screened by BLI using aptamer concentrations of 0.5 µM, 1 µM, or 2 µM. Again, the target was immobilized onto a Biolayer Interferometry sensor probe and then incubated with each aptamer clone. The results are presented below (FIGS. 26-30). Results for the clones that did not meet specifications are excluded for clarity.

FIGS. 26-30 show that the selected monoclonal aptamers have improved binding to their respective targets compared to the unselected naïve library. The immobilized targets showed little to no interaction with unrefined naïve aptamer population. Binding was seen between the immobilized targets and the respective selected monoclonal aptamers.

Rapid association of the monoclonal aptamers was seen for immobilized CdeM, CdeC, CotE and CotEC Chitinase (signals at ~60-240 sec). The bound monoclonal aptamers did not appear to show significant dissociation from CotEC Chitinase, CotA and CdeC. There was a higher rate of dissociation of the monoclonal aptamer from CdeM and CotE for the specific monoclonal aptamer pools used in this example (signals at ~240-420 sec); however, rapid association for their respective immobilized target protein occurred as described herein.

Both selected monoclonal aptamers for CotA showed slower association to their respective target but very little dissociation of the bound aptamers.

The naïve library control for the CotE aptamers showed a slight association. This was considered to be an anomalous result that has no effect on the integrity of the data.

Conclusion

Biolayer Interferometry shows that the selected monoclonal aptamers selected against CotA, CdeC, CdeM, CotE and CotEC Chitinase proteins, interact with their respective immobilized target. Interactions are a result of selection process (not simply through non-specific binding) as the 'naïve' population shows no such interaction.

Example 3—Detection

The ability of the Biovector CotE H2 aptamer to visualise *Clostridium difficile* SH11 bacterial spores on stainless-steel and gown surfaces, in ambient light and dark conditions was assessed.

Materials and Methods

*Clostridium difficile* purified spore suspensions used in this study are listed in Table 6. *C. difficile* suspensions were provided by SporeGen® and stored at 4° C. upon arrival.

TABLE 6

Test organisms

| | Ribotype | Format | Description | In test concentration (CFUmL-1) |
|---|---|---|---|---|
| *C. difficile* | RT078 (SH11) | Wild type | Purified spore suspension | 1 × 107 ± 5 × 106 |

Test agents used throughout the study are described in Table 7. The CotE H2 aptamer and TbKst buffer were provided by Aptamer Group.

TABLE 7

Test agents

| Test agent name | Format | Description | In-test aptamer concentration (µM) |
|---|---|---|---|
| Negative control 1 | Solid surface | Stainless-steel or gown surface only | N/A |
| Negative control 2 | Liquid | *C. difficile* SH11 spores only | N/A |
| Negative control 3 | Liquid | Horse blood only | N/A |
| Positive control 4 | Liquid | CotE H2 aptamer in TbKst buffer | 10 |
| CotE H2 + SH11 | Liquid | CotE H2 aptamer in TbKst buffer incubated with *C. difficile* SH11 spores | 10 |

Equipment:
  UKAS calibrated pipettes—Sartorius,
  UK Eppendorf 5452
  Minispin Centrifuge—Eppendorf, DE
  Polilight® Flare+2 forensic lights (wavelength 505 nm)—Rofin,
  UK Stainless-steel table
  Hospital gown surface
  Canon EOS 2000D camera—590 nm wavelength filter, Midwest Optical Systems, Inc.

Media:
  Nuclease free water—provided by Aptamer Group
  TbKst buffer—provided by Aptamer Group. The buffer solution contains 50 mM Tris pH 7.6, 2.5 mM $MgCl_2$, 2.5 mM $CaCl_2$, 28 mM $K_2SO_4$, 0.01% Tween, 0.01% BSA.
  Clinell sporicidal wipes—GAMA healthcare,
  UK 70% isopropyl alcohol (IPA)—Fisher Scientific, UK-1% Virkon solution—Scientific Laboratory Supplies, UK Method Assessment of the ability of the Biovector CotE H2 aptamer to detect *Clostridium difficile* SH11 bacterial spores on stainless-steel and gown surfaces, in ambient light and dark conditions.

CotE H2 aptamer and *Clostridium difficile* SH11 binding procedure:

Prior to testing, the CotE H2 aptamer was folded in nuclease free water by heating to 95° C. for 5 minutes. The CotE H2 aptamer was immediately cooled to 2° C. on ice. An inoculum of *C. difficile* SH11 bacterial spores was prepared to 1×107 CFU mL-1 from stock solution in nuclease free water. Once folded, 20 µL of the *C. difficile* SH11 spore suspension was added to 20 µL of 20 µM of folded CotE H2 aptamer to obtain a final concentration of 10 µM. The aptamers comprise a FAM fluorophore incorporated at the 5' end via a linker.

The aptamer-spore suspension was mixed and vortexed for 5 seconds to obtain a homogenous suspension and incubated for 1 hour at room temperature. Following incubation, the aptamer-spore suspension was washed by centrifugation to remove unbound CotE H2 aptamer. One hundred microliters of TbKst buffer was added to the aptamer-spore suspension and centrifuged at 12,100×g (13,000 rpm) for 10 minutes. The supernatant liquid was discarded. The aptamer-spore pellet was resuspended in 100 µL of TbKst buffer and vortexed for 10 minutes to obtain a homogenous suspension. For negative control 4 (CotE H2 aptamer in TbKst buffer without spores), 10 μL of TbKst buffer was added to 10 μL of 20 μM of folded CotE 112 aptamer to obtain a final concentration of 10 μM.

Detection of Bacterial Spores from *Clostridium difficile* SH11 on Stainless-Steel and Gown Surfaces in Ambient Light and Dark Conditions A stainless-steel surface was cleaned sequentially with sporicidal wipes, 1% Virkon™ solution and 70% isopropyl alcohol (IPA). Following cleaning, the surface was rinsed with water. The surface was divided into five 10×10 cm samples labelled S1-S5. Sample S1 was untreated to act as a clean surface control for the stainless-steel surface (negative control 1). Five×5 μL aliquots of the negative control 2 (*C. difficile* SH11 spores only), negative control 3 (horse blood only), positive control 4 (CotE H2 aptamer at 10 μM in TbKst buffer) and the aptamer-spore suspension were pipetted onto samples S2, S3, S4 and S5 respectively. The surface was allowed to dry at room temperature for 1 hour. Following drying, the fluorescence of the aptamer-spore suspension was assessed in ambient light and dark conditions, with and without the Polilight® Flare+2 forensic light (505 nm). Images of the fluorescence were taken with a Canon EOS 2000D with and without a 590 nm bandpass filter. Autofluorescence of the negative controls was also assessed. The test was repeated on hospital gown surfaces.

Results

Assessment of the Ability of the CotE H2 Aptamer to Detect *Clostridium difficile* SH11 Bacterial Spores on Stainless-Steel and Gown Surfaces, in Ambient Light and Dark Conditions:

Stainless-Steel Surface:

Ambient Light, without Polilight® Flare+2 Forensic and without 590 nm Bandpass Filter No visible fluorescence was observed for all the test samples without the exposure to Polilight® Flare+2 forensic light (505 nm) and the 590 nm bandpass filter in ambient light conditions (FIG. 31A-FIG. 31E).

Figure 32A:
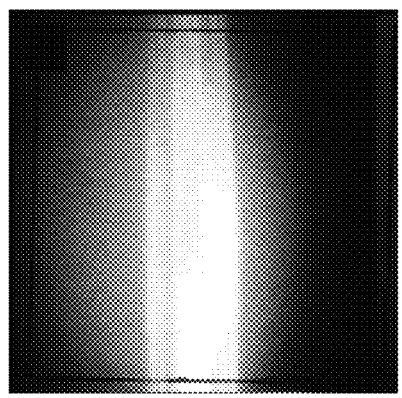
FIG. 32A-FIG. 32E show photographs of test samples on a stainless-steel surface under ambient light conditions with Polilight Flare+2 forensic light (505 nm) and without a 590 nm bandpass filter according to some embodiments of the present disclosure. For comparison.
Figure 32B:
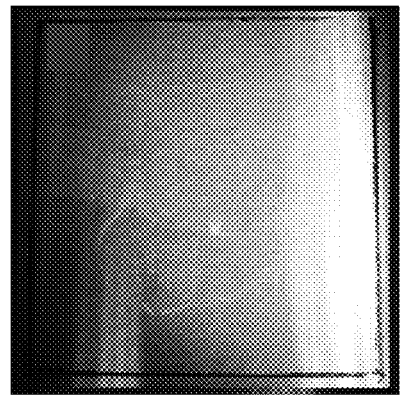
Figure 32C:
Figure 32D:
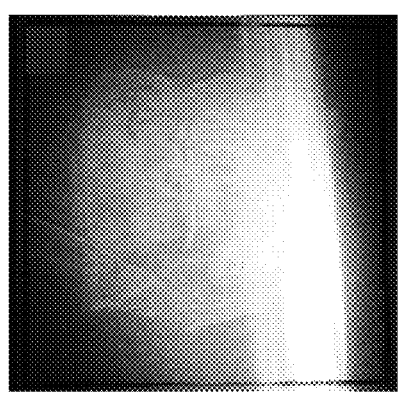
Figure 32E:
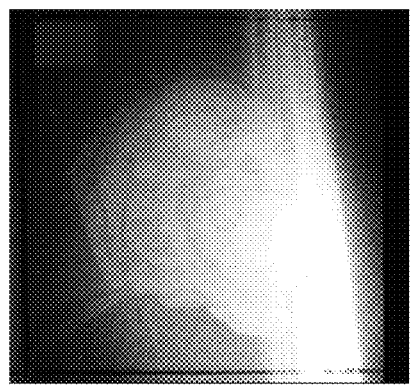

Ambient Light, with Polilight® Flare+2 Forensic and without 590 Nm Bandpass Filter Visible reflection of the Polilight® Flare+2 forensic light caused by the stainless-steel surface was observed for test sample when exposed to Polilight® Flare+2 forensic light (505 nm) without the 590 nm bandpass filter in ambient light conditions (FIG. 32A). Visible reflection of the test sample was also observed within the samples containing *C. difficile* SH11 spores (FIG. 32B), horse blood (FIG. 32C), CotE H2 aptamer at 10 μM (FIG. 32D), and the combination of CotE H2 aptamer 10 μM and *C. difficile* SH11 spores (FIG. 32E).

Ambient Light, with Polilight® Flare+2 Forensic and with 590 nm Bandpass Filter

Figure 33A:
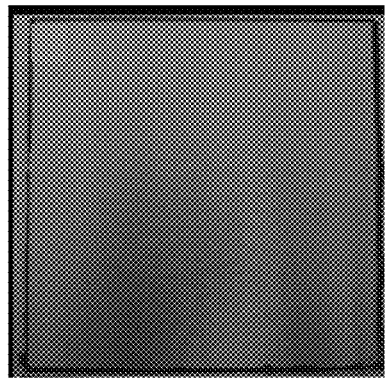
FIG. 33A-FIG. 33E show photographs of test samples on a stainless-steel surface under ambient light conditions with Polilight Flare+2 forensic light (505 nm) and with a 590 nm bandpass filter according to some embodiments of the present disclosure. For comparison.
Figure 33B:
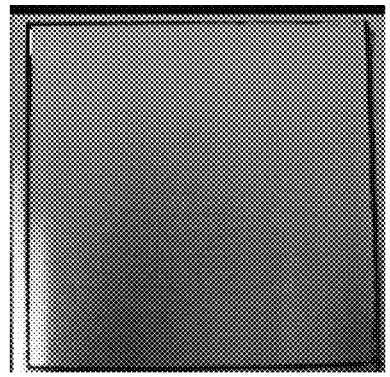
Figure 33C:
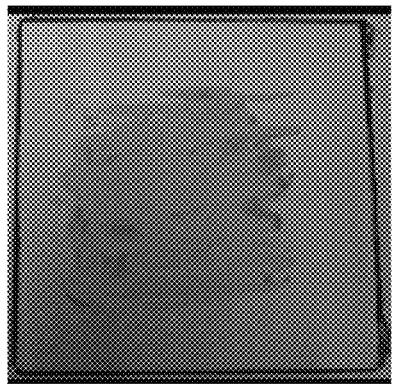
Figure 33D:
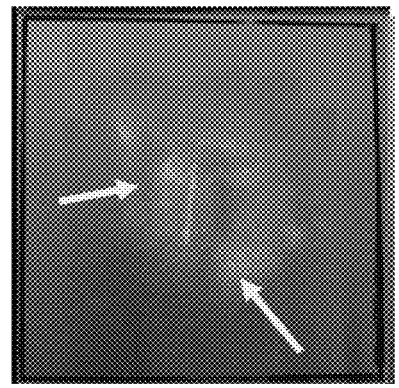
Figure 33E:
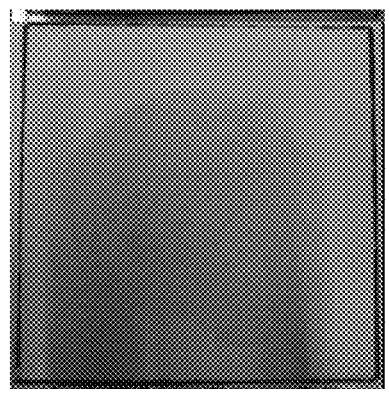

No visible reflection of the Polilight® Flare+2 forensic light caused by the stainless-steel surface was observed when exposed to Polilight® Flare+2 forensic light (505 nm) when using the 590 nm bandpass filter in ambient light conditions (FIG. 33A-FIG. 33E). No visible autofluorescence was observed on the samples containing the stainless-steel surface (FIG. 33A), *C. difficile* SH11 spores (FIG. 33B), or horse blood (FIG. 33C). Fluorescence was observed within the sample containing CotE H2 aptamer at 10 μM as illustrated by the bright light in FIG. 33D (solid arrows). No visible fluorescence was observed within the sample containing the combination of CotE H2 aptamer 10 μM and *C. difficile* SH11 spores (FIG. 33 E).

Figure 34A:
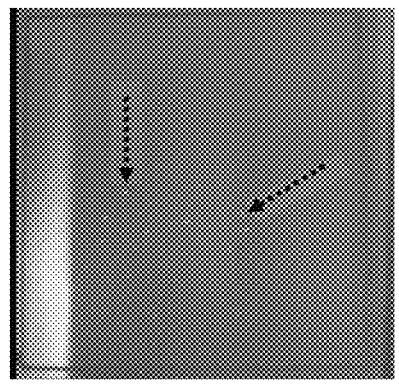
FIG. 34A-FIG. 34E show photographs of test samples on a stainless-steel surface under dark conditions, with exposure to Polilight Flare+2 forensic light (505 nm) and with a 590 nm bandpass filter according to some embodiments of the present disclosure. For comparison.
Figure 34B:
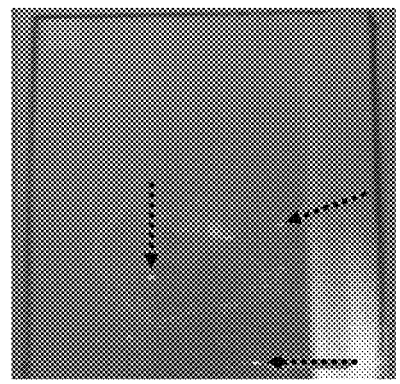
Figure 34C:
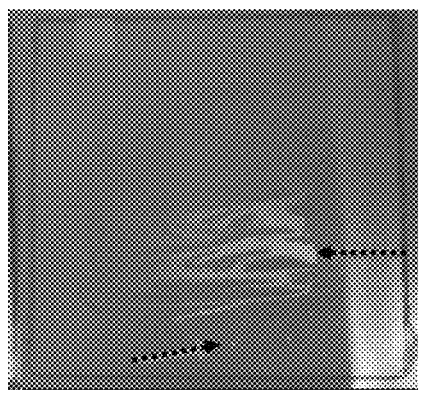
Figure 34D:
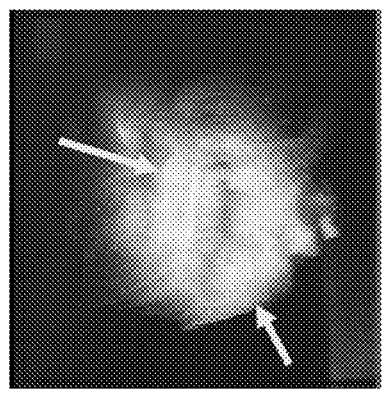
Figure 34E:
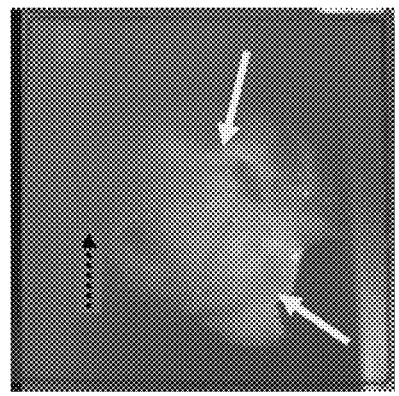

Dark Conditions, with Polilight® Flare+2 Forensic and with 590 Nm Bandpass Filter Some visible reflection of the Polilight® Flare+2 forensic light caused by the stainless-steel surface was observed for all the test samples when exposed to Polilight Flare+2 forensic light (505 nm) with the 590 nm bandpass filter in dark conditions (FIG. 34A-FIG. 34E). Minimal autofluorescence was observed within the samples containing the stainless-steel surface (FIG. 34A), *C. difficile* SH11 spores (FIG. 34B), or horse blood (FIG. 34C). Some autofluorescence was also observed from particles present on the surface (indicated by dashed arrows, FIGS. 34, A, B, C and E). Fluorescence was observed on the stainless-steel surface, within the sample containing CotE H2 aptamer at 10 μM as illustrated by the bright light in FIG. 34D (solid arrows). Fluorescence was also observed with the sample containing the combination of CotE H2 aptamer 10 μM and *C. difficile* SH11 spores (FIG. 34E; solid arrows).

Gown Surface

Ambient Light, without Polilight® Flare+2 Forensic and without 590 nm Bandpass Filter No fluorescence was observed for the gown surface test samples without the exposure to Polilight® Flare+2 forensic light (505 nm) and the 590 nm bandpass filter in ambient light conditions (FIG. 35A-FIG. 35E).

Figure 36A:
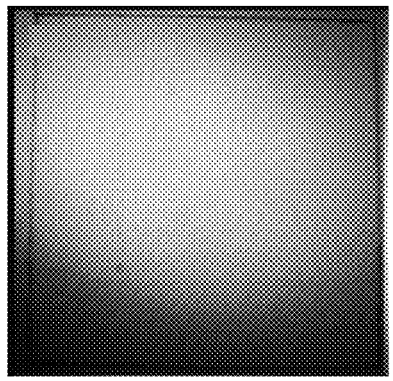
FIG. 36A-FIG. 36E show photographs of test samples on a gown surface under ambient light conditions with Polilight Flare+2 forensic light (505 nm) and without 590 nm bandpass filter according to some embodiments of the present disclosure. For comparison.
Figure 36B:
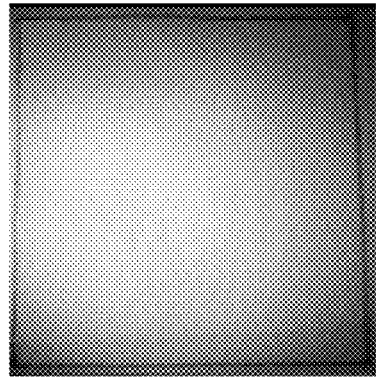
Figure 36C:
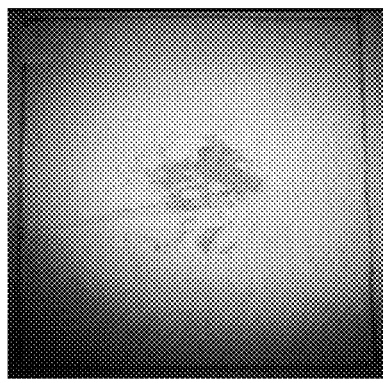
Figure 36D:
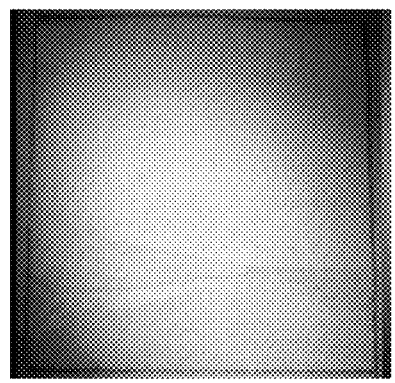
Figure 36E:
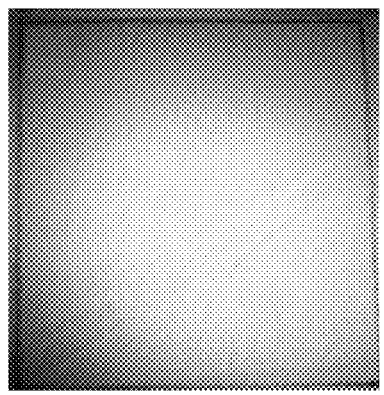

Ambient Light, with Polilight® Flare+2 Forensic and without 590 nm Bandpass Filter No visible fluorescence was observed for the test samples on the gown surface when exposed to Polilight® Flare+2 forensic light (505 nm) when observed without the 590 nm bandpass filter in ambient light conditions (FIG. 36A-FIG. 36E). Visible reflection of the Polilight® Flare+2 forensic light caused by the gown surface was observed for test samples when exposed to Polilight® Flare+2 forensic light (505 nm) without the 590 nm bandpass filter in ambient light conditions (FIG. 36A). Visible reflection of test samples was also observed within the samples containing *C. difficile* SH11 spores (FIG. 36B), horse blood (FIG. 36C), CotE H2 aptamer at 10 μM (FIG. 36D), and the combination of CotE H2 aptamer 10 μM and *C. difficile* SH11 spores (FIG. 36D).

Ambient Light, with Polilight® Flare+2 Forensic and with 590 nm Bandpass Filter

Figure 37A:
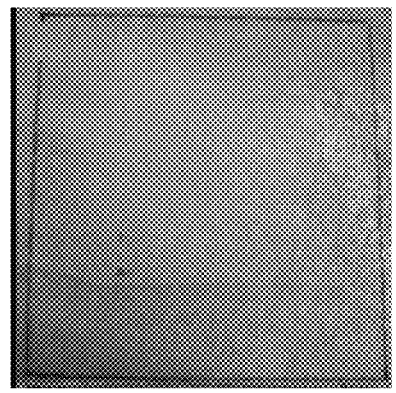
FIG. 37A-FIG. 37E show photographs of test samples on a gown surface under ambient light conditions with Polilight Flare+2 forensic light (505 nm) and with 590 nm bandpass filter according to some embodiments of the present disclosure. For comparison.
Figure 37B:
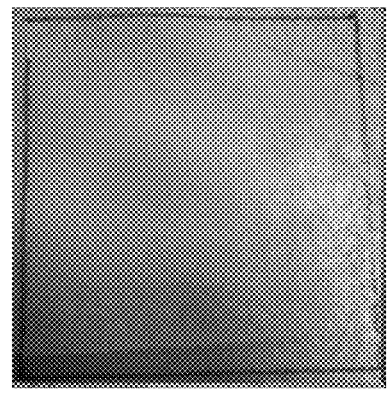
Figure 37C:
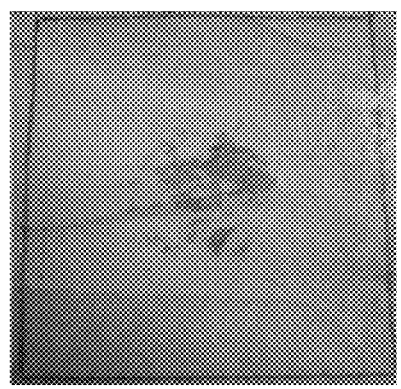
Figure 37D:
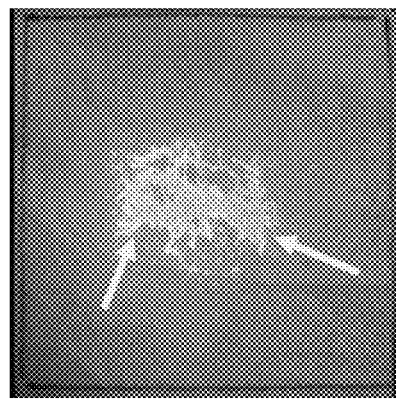
Figure 37E:
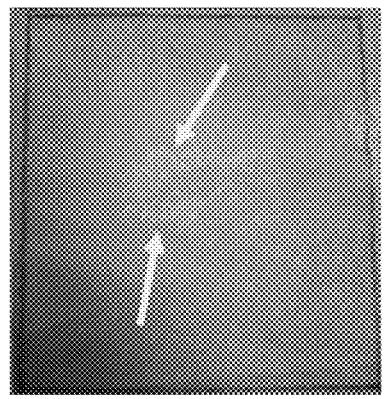

Bright green/yellow fluorescence was observed within the sample containing CotE H2 aptamer at 10 μM (FIG. 37D; solid arrows) and, visible fluorescence was observed within the sample containing the combination of CotE 112 aptamer 10 μM and *C. difficile* SH11 spores (FIG. 37E; solid arrows). No visible reflection of the Polilight® Flare+2 forensic light was observed on the gown surfaces when they were exposed to Polilight® Flare+2 forensic light (505 nm) and observed with the 590 nm bandpass filter in ambient light conditions (FIG. 37A-FIG. 37E).

Figure 38A:
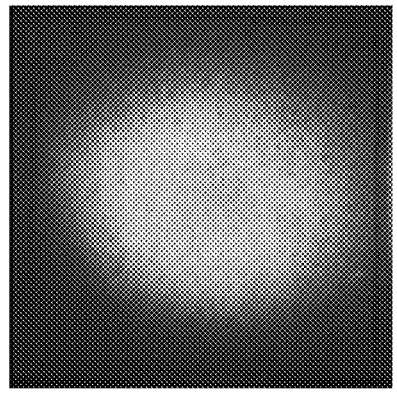
FIG. 38A-FIG. 38E show photographs of test samples on a stainless-steel surface under dark conditions with Polilight Flare+2 forensic light (505 nm) and with 590 nm bandpass filter according to some embodiments of the present disclosure. For comparison.
Figure 38B:
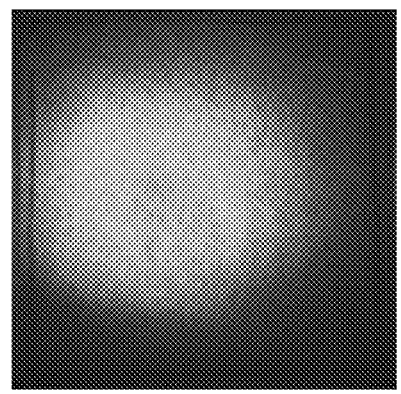
Figure 38C:
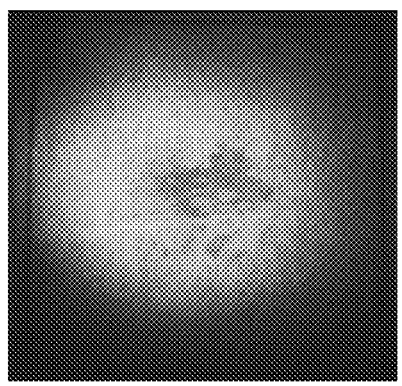
Figure 38D:
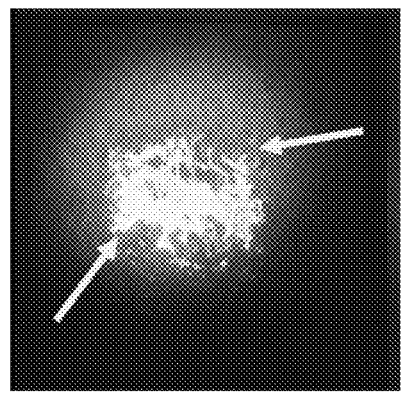
Figure 38E:
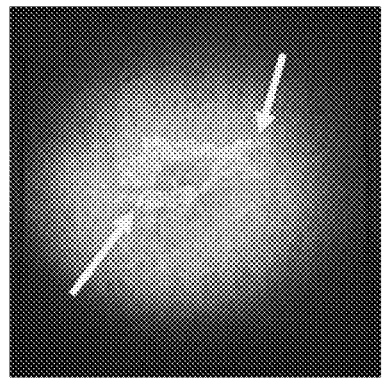

Dark Conditions, with Polilight® Flare+2 Forensic and with 590 nm Bandpass Filter Bright fluorescence was observed within the sample containing CotE H2 aptamer at 10 μM (FIG. 38D; solid arrows). Fluorescence was observed within the sample containing the combination of CotE H2 aptamer 10 μM and *C. difficile* SH11 spores (FIG. 38E; solid arrows). No autofluorescence was observed within the samples containing the gown surface, *C. difficile* SH11 spores or horse blood (FIGS. 38A-38C).

Discussion

*C. difficile* is an anaerobic spore-forming microorganism and is considered a leading cause of infections worldwide, with elevated rates of morbidity. A method of visual identification of *C. difficile* spore contamination in the health care environment would allow improved cleaning procedures.

The assessment of fluorescence for the stainless-steel showed that fluorescence was detected only under dark conditions. The assessment of fluorescence for the gown surface showed that fluorescence of the CotE H2 aptamer in combination with C. difficile SH11 spores was detected under both ambient light and dark conditions. The intensity of the fluorescence observed on the gown surface in response to the presence of the combination CotE H2 aptamer and C. difficile SH11 spores under ambient light conditions was lower than intensity of the fluorescence under dark conditions. No visible reflection or autofluorescence was detected on the gown surface controls, but a high amount of reflection was observed on stainless-steel samples.

Example 4—Minimal Binding Fragments

A fragment of the chitinase_D11 aptamer (SEQ ID NO: 5) was found to bind to C. difficile spores. The fragment extended from position 28 to position 64 of SEQ ID NO: 5. This sequence is also shown in SEQ ID NO: 23. Binding was identified using an ELISA-type assay in which a biotinylated fragment of SEQ ID NO: 23 was used in a similar manner to a primary antibody. A streptavidin-HRP conjugate was used as a secondary binding partner.

Several fragments of the C. diff-F1 aptamer (SEQ ID NO: 1) were found to bind to C. difficile spores. The sequence for the minimal fragment, C diff-F1-f10, is 5'-CCATACT-CAATGCTCTTACGATCCTCATCAACC-3', and is 33 bases long (SEQ ID NO: 24). The fragment comprises 23 contiguous nucleotides extending from position 12 to position 35 of SEQ ID NO: 1.

Several fragments of the C. diff-G1 aptamer (SEQ ID NO: 2) were found to bind to C. difficile spores. The sequence for the minimal fragment, C diff-G1-f6, is 5'-CCAGTGTA-GACTACTCAATGCTCTTACGATCCTCATCAACC-3', and is 41 bases long (SEQ ID NO: 25). The fragment comprises 21 contiguous nucleotides extending from position 1 to position 21 of Seq ID NO: 2.

Several fragments of the CotE-H2 aptamer (SEQ ID NO: 11) were found to bind to C. difficile spores. The sequence for the minimal fragment, CotE-H2-f4, is 5'-AGTGTAGAC-TACTCAATGCGGCTGGCCACAGGTCAACC-3', and is 40 bases long (SEQ ID NO: 26). The sequence comprises 24 contiguous nucleotides from the 5' end and 13 contiguous nucleotides from the 3' end of SEQ ID NO: 11 (with an internal truncation of 42 nucleotides from SEQ ID NO: 11) which were combined with an additional guanine bridge.

In a single point ELISA assay, the minimal fragments C diff-F1-f10, C diff-G1-f6, and CotE-H2-f4 each displayed preferential binding to spores from C. diff. over B. sub. (approximately two-fold).

Example 5—Aptamer Binding to Proteins

The binding affinity, as reported by the equilibrium dissociation constant ($K_D$), was determined for several aptamers and proteins (performed under contract by NeoVentures Biotechnology Inc. (London, Ontario, Canada)).

For CotE D2, CotE H2 and CotEC chitinase, aptamers were spotted on a gold surface at a concentration of 5 µM in PBS at a volume of approximately 10 nL in triplicate. Negative aptamers of the same length as the positive aptamers were spotted in the same manner, also in triplicate. Protein was then injected over the chip at a volume of 200 µL, with a flow rate of 50 µL/min in a Horiba (OpenPlex) surface plasmon resonance imaging (SPRi) instrument. Resonance due to binding was obtained by subtracting total resonance on the negative sequences from total resonance on the positive sequences. Disassociation values were computed with the following equation: $dx/dt \sim -kd*x$, wherein dx/dt is the derivative of resonance values as a function of time and x is the resonance value for any given time point. Association values were computed with the following equation: $dx/dt \sim ka*c*R\,max-(ka*c+kd)*x$, where x is the resonance due to binding at specific time points, c is the concentration of injectant, and R max is the maximum resonance observed.

For CotA C1, the protein was immobilized on a hydrogel chip with EDC-mediated conjugation between primary amines on the protein (side chains on residues) and carboxylic acid groups on the surface of the chip. A protein of similar size was immobilized in the same manner as a negative control. The variation in concentration for this data is in the amount of aptamer injected. For CdeC D1, the protein was received as aggregated, insoluble balls of protein. The binding assay was performed by incubating fluorescently labeled aptamers (FAM) with the protein, and then spinning the tubes down in a microcentrifuge to remove unbound. The pellet was resuspended in selection buffer and spun down again. Bound aptamers were eluted by adding 6 M urea, and spinning again, retaining the supernatant. The aptamers were cleaned up with PCR cleanup columns and the fluorescence was read on a Tecan Sapphire II fluorometer. Excitation was at 497 nm, and emission was at 515 nm. The amount of fluorescence measured in the eluant was divided by the total amount of fluorescence of all fractions.

For aptamer CotE H2 (SEQ ID NO: 11), the $K_D$ was determined to be 1.43E-07 (at 250 nM protein), 9.16E-08 (at 125 nM protein), and 8.47E-08 (at 62.5 nM protein), respectively. For aptamer CotE D2 (SEQ ID NO: 13), the $K_D$ was determined to be greater than 250 nM. For aptamer CotA C1 (SEQ ID NO: 10), the $K_D$ was determined to be 6.874E-09. For aptamer CotEC Chitinase D11 (SEQ ID NO: 5), the $K_D$ was determined to be 2.54E-07 (at 500 nM protein), 2.35E-07 (at 750 nM protein), and 2.75E-07 (at 1000 nM protein), respectively. For aptamer CdeC D1 (SEQ ID No 6), the $K_D$ was not determined due to protein aggregation.

The references cited throughout this application, are incorporated herein in their entireties for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed but is intended to cover all modifications which are within the spirit and scope of the invention as defined by the appended claims; the above description; and/or shown in the attached drawings.

What is claimed is:

1. An aptamer having a specific binding affinity for a surface protein of *Clostridium difficile* spore, wherein the aptamer comprises from position 22 to position 61 of the nucleotide sequence of SEQ ID NO: 14.

2. The aptamer of claim 1, wherein the surface protein is exosporium layer protein CdeM.

3. The aptamer of claim 2, wherein the surface protein is CdeM having an amino acid sequence as set forth in SEQ ID NO: 19.

4. The aptamer of claim 1, wherein the aptamer comprises a detectable label.

5. The aptamer of claim 4, wherein the detectable label comprises a fluorophore, a nanoparticle, a radioactive isotope, a biotin, a protein or a combination thereof.

6. An apparatus for detecting the presence, absence or level of *Clostridium difficile* spores in a sample, the apparatus comprising:
 a support; and
 at least one aptamer having a specific binding affinity for a surface protein of *Clostridium difficile* spore, wherein the at least one aptamer comprises from position 22 to position 61 of the nucleotide sequence of SEQ ID NO: 14.

7. The apparatus of claim 6, wherein the surface protein is exosporium layer protein CdeM.

8. A composition comprising at least one aptamer having a specific binding affinity for a surface protein of *Clostridium difficile* spore, wherein the at least one aptamer comprises from position 22 to position 61 of the nucleotide sequence of SEQ ID NO: 14.

9. The composition of claim 8, wherein the surface protein is exosporium layer protein CdeM.

10. The composition of claim 8, wherein at least one aptamer comprises a detectable label.

11. The aptamer of claim 4, wherein the aptamer is conjugated to a fluorophore.

12. The aptamer of claim 5, wherein the protein is an enzyme or an antibody.

13. The aptamer of claim 5, wherein the nanoparticle is a quantum dot, a colloidal metallic particle, a colloidal non-metallic particle, an organic polymer, a nanofiber, or a nanotube.

\* \* \* \* \*